(12) United States Patent
Sanders et al.

(10) Patent No.: US 10,689,710 B2
(45) Date of Patent: Jun. 23, 2020

(54) METHODS FOR SCREENING SOLID TUMORS FOR MUTATIONS

(71) Applicant: Quest Diagnostics Investments Incorporated, Wilmington, DE (US)

(72) Inventors: Heather Sanders, San Juan Capistrano, CA (US); Kevin Qu, San Juan Capistrano, CA (US); James Prentice, San Juan Capistrano, CA (US); Frederic Waldman, San Juan Capistrano, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 55 days.

(21) Appl. No.: 15/576,219

(22) PCT Filed: Oct. 28, 2015

(86) PCT No.: PCT/US2015/057733
§ 371 (c)(1),
(2) Date: Nov. 21, 2017

(87) PCT Pub. No.: WO2016/190897
PCT Pub. Date: Dec. 1, 2016

(65) Prior Publication Data
US 2018/0142304 A1       May 24, 2018

Related U.S. Application Data

(60) Provisional application No. 62/166,996, filed on May 27, 2015, provisional application No. 62/246,895, filed on Oct. 27, 2015.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 8,026,053 B2 * | 9/2011 | Samuels | C12Q 1/6886 435/6.14 |
| 2010/0203532 A1 * | 8/2010 | Makrigiorgos | C12Q 1/6858 435/6.12 |
| 2014/0031240 A1 | 1/2014 | Behlke et al. | |
| 2014/0220032 A1 * | 8/2014 | Jones | C12Q 1/485 424/158.1 |

FOREIGN PATENT DOCUMENTS

| | | |
|---|---|---|
| WO | WO 2012/092426 A1 | 7/2012 |
| WO | WO 2014/004726 A1 | 1/2014 |
| WO | WO 2014/144121 A2 | 9/2014 |
| WO | WO-2014/182521 A1 | 11/2014 |

OTHER PUBLICATIONS

The Cancer Genome Atlas Network (Nature. Oct. 2012. 490: 61-70).*
International Search Report issued in application No. PCT/US2015/057733 dated Mar. 31, 2016.
Supplementary European Search Report dated Dec. 4, 2018, in EP 15893532.0.

* cited by examiner

*Primary Examiner* — Carla J Myers
(74) *Attorney, Agent, or Firm* — Foley & Lardner LLP

(57) ABSTRACT

The present technology relates to methods for determining whether a patient diagnosed with breast cancer, colorectal cancer, melanoma or lung cancer will benefit from or is predicted to be responsive to treatment with an individual therapeutic agent or a specific combination of therapeutic agents. These methods are based on screening a patient's solid tumors and detecting alterations in target nucleic acid sequences corresponding to a specific set of cancer-related genes. Kits for use in practicing the methods are also provided.

14 Claims, 11 Drawing Sheets

Specification includes a Sequence Listing.

FIGURE 1

| | Melanoma | | | Lung Cancer | | | Breast Cancer | | | Colorectal Cancer | | |
|---|---|---|---|---|---|---|---|---|---|---|---|---|
| | Number (%) | Range | Median | Number (%) | Range | Median | Number (%) | Range | Median | Number (%) | Range | Median |
| Patient Age | | | | | | | | | | | | |
| All | 31 | 24-89 | 65.0 | 27 | 42-88 | 68.0 | 30 | 35-86 | 57.0 | 33 | 33-87 | 65.0 |
| Male | 22 (70.9) | 24-89 | 66.5 | 10 (37) | 61-88 | 68.0 | 1 (3.3) | 82-82 | 82.0 | 18 (54.6) | 44-87 | 68.0 |
| Female | 9 (29.1) | 46-83 | 58.0 | 17 (63) | 42-87 | 65.0 | 29 (96.7) | 35-86 | 57.0 | 15 (45.4) | 33-80 | 61.0 |
| Tissue source | | | | | | | | | | | | |
| Resection/tissue excision | 14 (45.2) | | | 11 (40.7) | | | 3 (10) | | | 28 (85) | | |
| Biopsy | 10 (32.3) | | | 10 (37) | | | 27 (90) | | | 2 (6) | | |
| Excised lymph node | 6 (19.4) | | | 5 (18.5) | | | 0 | | | 2 (6) | | |
| No tissue source information | 1 (3.2) | | | 1 (3.7) | | | 0 | | | 1 (3) | | |
| Stage | | | | | | | | | | | | |
| I | 0 | | | 2 (7.4) | | | 17 (56.7) | | | 2 (6.1) | | |
| II | 7 (22.6) | | | 6 (22.2) | | | 8 (26.7) | | | 5 (15.2) | | |
| III | 7 (22.6) | | | 3 (11.1) | | | 1 (3.3) | | | 14 (42.4) | | |
| IV | 11 (35.5) | | | 4 (14.8) | | | 0 | | | 9 (27.3) | | |
| No stage information | 6 (19.4) | | | 12 (44.4) | | | 4 (13.3) | | | 3 (9.1) | | |
| Grade | | | | | | | | | | | | |
| Well differentiated | 0 | | | 4 (14.8) | | | 3 (10) | | | 7 (21.2) | | |
| Moderately differentiated | 0 | | | 3 (11.1) | | | 9 (30) | | | 13 (39.4) | | |
| Poorly differentiated | 5 (16.2) | | | 10 (37) | | | 12 (40) | | | 7 (21.2) | | |
| No grade information | 26 (83.9) | | | 10 (37) | | | 6 (20) | | | 6 (18.2) | | |

FIGURE 2

| Sample Name | Known Variant | Reads | Variant Frequency | | | | | |
|---|---|---|---|---|---|---|---|---|
| | | | ,ect | In | Intra-2 | Intra-3 | Mean | SD |
| *6% EGFR L858R Horizon Standard* | | | | | | | | |
| | EGFR L858R | Frequency | 6% | 4.6% | 4.6% | 4.3% | 4.5% | 0.2% |
| | | Total Cov | | 2286 | 2453 | 2093 | 2277 | 180 |
| | | F/R Ref | | 1215/964 | 1433/906 | 1121/880 | 1256/917 | 160/42 |
| | | F/R Var | | 71/34 | 81/31 | 72/18 | 75/28 | 5/8 |
| *7% AKT1 E17K* | | | | | | | | |
| | AKT1 E17K | Frequency | 7% | 11.9% | 13.8% | 12.0% | 12.6% | 1.1% |
| | | Total Cov | | 1549 | 1171 | 2330 | 1683 | 591 |
| | | F/R Ref | | 770/595 | 652/356 | 1410/640 | 944/530 | 407/152 |
| | | F/R Var | | 28/155 | 34/127 | 48/230 | 36/171 | 10/53 |
| | EGFR E746_A750del | Frequency | 43% | 31.0% | 31.0% | 32.0% | 31.3% | 0.6% |
| | | Total Cov | | 3946 | 3699 | 3925 | 3857 | 137 |
| | | F/R Ref | | 1245/1470 | 1196/1354 | 1195/1468 | 1212/1430 | 28/66 |
| | | F/R Var | | 601/628 | 545/602 | 641/619 | 595/617 | 48/13 |
| *10% EGFR delE746_A750* | | | | | | | | |
| | EGFR E746_A750del | Frequency | 10% | 6.2% | 6.4% | 5.9% | 6.2% | 0.3% |
| | | Total Cov | | 3972 | 3970 | 3970 | 3971 | 1 |
| | | F/R Ref | | 1969/1757 | 1907/1807 | 2035/1699 | 1970/1754 | 64/54 |
| | | F/R Var | | 128/116 | 126/128 | 121/113 | 125/119 | 3/8 |
| | EGFR L858R | Frequency | 4.80% | 4.0% | 4.1% | 3.4% | 3.8% | 0.4% |
| | | Total Cov | | 1967 | 1690 | 1575 | 1744 | 202 |
| | | F/R Ref | | 1141/746 | 1021/599 | 857/663 | 1006/669 | 142/73 |
| | | F/R Var | | 55/23 | 46/23 | 27/27 | 42/24 | 14/2 |
| *STv1-14-1414\** | | | | | | | | |
| | BRAF G466Y | Frequency | | 40.17 | 40.1 | 41.57 | 40.61 | 0.83 |
| | | Total Cov | | 5368 | 6688 | 2806 | 4954 | 1973 |
| | | F/R Ref | | 2057/1152 | 2587/1417 | 1107/530 | 1917/1033 | 749/455 |
| | | F/R Var | | 1259/899 | 1474/1209 | 690/477 | 1141/861 | 405/367 |
| | TP53 R175H | Frequency | | 40.46 | 40.27 | 41.25 | 40.66 | 0.52 |
| | | Total Cov | | 4877 | 7343 | 3883 | 5367 | 1781 |
| | | F/R Ref | | 1751/1149 | 2794/1590 | 1360/919 | 1968/1219 | 741/340 |
| | | F/R Var | | 1131/844 | 1792/1165 | 947/655 | 1290/888 | 444/257 |
| | DDR2 L34P | Frequency | | 16.7 | 12.06 | 13.64 | 14.13 | 2.36 |
| | | Total Cov | | 2348 | 2833 | 3253 | 2811 | 452 |
| | | F/R Ref | | 564/1392 | 1309/1181 | 1403/1406 | 1092/1326 | 459/126 |
| | | F/R Var | | 264/127 | 220/121 | 291/152 | 258/133 | 35/16 |
| *STv1-14-1326\** | | | | | | | | |
| | TP53 A159_M160insRA | Frequency | | 24.63 | 28.38 | 23.18 | 25.40 | 2.68 |
| | | Total Cov | | 3958 | 3964 | 3964 | 3962 | 3 |
| | | F/R Ref | | 2373/1201 | 1954/875 | 1962/1074 | 2096/1050 | 239/164 |
| | | F/R Var | | 695/340 | 794/339 | 560/366 | 683/348 | 117/15 |
| *STv1-14-1454\** | | | | | | | | |
| | EGFR E865G | Frequency | | 4.59 | 4.52 | 4.73 | 4.61 | 0.11 |
| | | Total Cov | | 7392 | 8372 | 4924 | 6896 | 1776 |
| | | F/R Ref | | 3343/3709 | 3637/4356 | 2467/2223 | 3149/3429 | 608/1093 |
| | | F/R Var | | 242/96 | 213/164 | 87/145 | 180/135 | 82/35 |
| | EGFR E866V | Frequency | | 5.39 | 6.06 | 6.22 | 5.89 | 0.44 |
| | | Total Cov | | 9289 | 11165 | 7084 | 9179 | 2042 |
| | | F/R Ref | | 3881/4906 | 4176/6310 | 3037/3605 | 3698/4940 | 591/1352 |
| | | F/R Var | | 378/122 | 520/157 | 374/66 | 424/115 | 83/45 |
| | Notch Q2406del | Frequency | | 39.2 | 44.47 | 35.63 | 39.77 | 4.45 |
| | | Total Cov | | 3832 | 4000 | 3347 | 3726 | 339 |
| | | F/R Ref | | 2271/58 | 790/1430 | 752/1401 | 1271/963 | 866/783 |
| | | F/R Var | | 518/983 | 1633/145 | 1052/140 | 1067/422 | 557/485 |
| | TP53 R248W | Frequency | | 61.23 | 62.27 | 63.5 | 62.33 | 1.14 |
| | | F/R Ref | | 1045/432 | 1503/963 | 694/529 | 1080/641 | 405/282 |
| | | F/R Var | | 1663/672 | 2244/1829 | 1091/1037 | 1666/1179 | 576/591 |

*Clinical specimens

FIGURE 3

| Sample Name | Known Variant | | Expected | Variant Frequency .1 | .2 | .3 | Mean | SD |
|---|---|---|---|---|---|---|---|---|
| *6% EGFR L858R Horizon Standard* | | | | | | | | |
| | EGFR L858R | Frequency | 6% | 4.2% | 4.6% | 5.4% | 4.7% | 0.6% |
| | | Total Cov | | 4714 | 2453 | 1547 | 2905 | 1631 |
| | | F/R Ref | | 2340/2174 | 1433/906 | 900/563 | 1558/1214 | 727/848 |
| | | F/R Var | | 129/69 | 81/31 | 55/27 | 88/42 | 37/22 |
| *7% AKT1 E17K* | | | | | | | | |
| | AKT1 E17K | Frequency | 7% | 11.9% | 10.6% | 11.9% | 11.5% | 0.8% |
| | | Total Cov | | 2733 | 2585 | 1549 | 2289 | 645 |
| | | F/R Ref | | 1704/710 | 1801/508 | 770/595 | 1425/604 | 569/101 |
| | | F/R Var | | 31/286 | 53/221 | 28/155 | 37/221 | 13/65 |
| | EGFR E746_A750del | Frequency | 43% | 31.7% | 28.2% | 31.0% | 30.3% | 1.9% |
| | | Total Cov | | 3985 | 3942 | 3946 | 3958 | 24 |
| | | F/R Ref | | 1244/1477 | 1146/1680 | 1245/1470 | 1212/1542 | 57/119 |
| | | F/R Var | | 574/688 | 517/597 | 601/628 | 564/638 | 42/46 |
| *10% EGFR delE746_A750* | | | | | | | | |
| | EGFR E746_A750del | Frequency | 10% | 6.5% | 7.4% | 6.4% | 6.8% | 0.6% |
| | | Total Cov | | 3996 | 3976 | 3970 | 3981 | 14 |
| | | F/R Ref | | 1776/1961 | 1796/1883 | 1907/1807 | 1826/1884 | 70/76 |
| | | F/R Var | | 127/130 | 140/155 | 126/128 | 131/138 | 8/14 |
| | EGFR L858R | Frequency | 4.80% | 2.9% | 2.1% | 4.1% | 3.0% | 1.0% |
| | | Total Cov | | 4390 | 2483 | 1690 | 2854 | 1388 |
| | | F/R Ref | | 2455/1806 | 1283/1146 | 1021/599 | 1586/1184 | 763/604 |
| | | F/R Var | | 79/48 | 49/3 | 46/23 | 58/25 | 18/22 |

FIGURE 6D
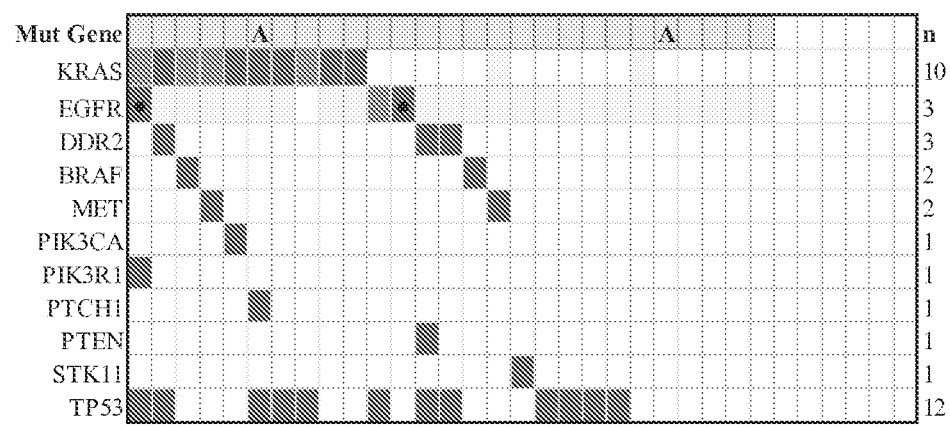
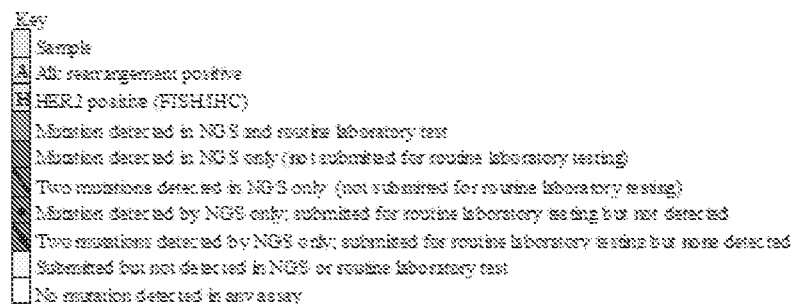

FIGURE 7

| Laboratory Result | % Cases (n) | OncoVantage Gene |
|---|---|---|
| *HER2 results available* | *n=28* | |
|     HER2 negative | 78.6% (22/28) | |
|         *Triple Negative* | *8.7% (2/23)* | |
|             50% (1/2) | | PIK3CA |
|             50% (1/2) | | Other |
|         *HER2-/ER+/PR+* | *65.2% (15/23)* | |
|             33.3% (5/15) | | PIK3CA |
|             13.3% (2/15) | | PIK3CA and ERBB2 |
|             6.7% (1/15) | | PIK3R1 |
|             6.7% (1/15) | | PTEN |
|             13.3% (2/15) | | No mutations |
|             20% (3/15) | | Other |
|         *HER2-/ER+/PR-* | *17.9% (5/28)* | |
|             20% (1/5) | | PIK3CA and BRAF$^{E501K}$ |
|             80% (4/5) | | Other |
|     HER2 positive | 21.4% (6/28) | |
|         *Triple positive* | *7.1% (2/28)* | |
|             50% (1/2) | | Other |
|             50% (1/2) | | No mutations |
|         *HER2+/ER+/PR-* | *10.7% (3/28)* | |
|             33.3% (1/3) | | Other |
|             66.7% (2/3) | | No mutations |
|         *HER2+/ER-/PR-* | *3.6% (1/28)* | |
|             100% (1/1) | | PIK3CA |
| HER2 results not available | n=2 | |
|     ER-/PR- (HER2 N/A) | 50% (1/2) | |
|         100% (1/1) | | ERBB4 and BRAF$^{V600E}$ |
|     ER+/PR+ | 50% (1/2) | |
|         100% (1/1) | | PIK3CA |
| Total with ERBB, PI3K pathway, and/or PTEN mutations = 50% (15/30) | | |

Genes with co-occurring mutations not listed are: TP53, NOTCH1, SMO, MAP2K1, PTCH1, and MET.

SEQUENCE LISTING

```
<160> NUMBER OF SEQ ID NOS: 464

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cctagtagaa tgtttactac caa                                              23

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgcttcttg agtaacactt                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
catgttcatg ctgtgtatgt                                                  20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcttctttac aaacgttcag aa                                               22

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
tctatgttcg aacaggtatc t                                              21

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
actgctaaac actaatataa cctttg                                         26

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttgaaatgtg ttttataatt tagactagt                                      29

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccatgaggta ctggcc                                                    16

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttggtgttac tggatcaaat c                                              21

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgctgaacca gtcaaact                                                  18

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 11
tattatttta ttttacagag taacagacta g                                    31

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttagcactt acctgtgact                                                 20

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggaatgcca gaactaca                                                   18

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtggaagatc caatccattt t                                               21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggaatgaatg gctgaattat g                                               21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcggtataat caggagtttt                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
```
agttggcctg aatcactata                                              20

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gatgttacta ttgtgacgat ctc                                          23

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtaagtgtta ctcaagaagc                                              20

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ataggatatt gtatcatacc aatttct                                      27

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tccacagcta caccatatat                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agcatcagca tttgacttta                                              20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tacacagaca ctctagtatc tg                                              22

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaaggtttga ctgccataaa                                                 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atgacaaaga acagctcaaa                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gagatcagcc aaattcagtt                                                 20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gatgtgttac aaggcttatc ta                                              22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcctcttgct cagttttatc                                                 20

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gaggctttgg agtatttca                                                  19

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctgctgagag ttattaacag t                                              21

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcttttggag tcctattgt                                                 19

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cacaaactag agtcacacac                                                20

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gggttttggg ctgatatta                                                 19

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccacagaact gaaggttaat                                                20

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttatccattg aatttatttt aatctttcta g                                   31

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gggatgtgcg ggtatatt                                                18

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtcttgcagt aagagattgt                                              20

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tctttgctgt accgct                                                  16

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtttcttttg cctgca                                                  16

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tggataaggt ctggtttaat g                                            21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gctacaattc aggatgagtt a                                            21

-continued

```
<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tcttctgcta tcaccatctt t                                              21

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccatcatgat gagaagacat                                                20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ttgctggaga tacatacact                                                20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtggtcacta aaccttaaga                                                20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggcttacctt agtgtaagag                                                20

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tttcatcgag atgggaaata tg                                             22

<210> SEQ ID NO 48
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acctgttggt atttggatac t                                              21

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agaagataat attgaagctg tagg                                           24

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agaactctta tttttaatc tgattttca                                       29

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggacagctat tgaagcattt a                                              21

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cacaagaaca agggaaacac                                                20

<210> SEQ ID NO 53
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gcaggcagct gagtatc                                                   17

<210> SEQ ID NO 54
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tcatcctgaa ttgtagcaat ca                                              22

<210> SEQ ID NO 55
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cagcttctgc catctct                                                    17

<210> SEQ ID NO 56
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
agcagccgca gaaat                                                      15

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57 gtggctttt gtttgtttg                                                   19

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cactctaaca agcagataac t                                               21

<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tacttgttaa ttaaaaattc aagagtttt                                       29

<210> SEQ ID NO 60
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 60
cttagccatt ggtcaagatc                                              20

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
acaatcatgt tgcagca                                                 17

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aaaaacatca aaaataact tacctttt                                      28

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
agaggcgcta tgtgtatta                                               19

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
catggaagga tgagaatttc a                                            21

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ggaagacaag ttcatgtact                                              20

<210> SEQ ID NO 66
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 66
ctgtccttat tttggatatt tctc                                          24

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
attaattaaa tatgtcattt catttctttt tc                                 32

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gctatcgatt tcttgatcac a                                             21

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tgagtcatat ttgtgggttt tc                                            22

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tgatcaggtt cattgtcact aa                                            22

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tttgattgct gcatatttca g                                             21

<210> SEQ ID NO 72
<211> LENGTH: 23
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 72
tcaaagcatt cttaccttac tac                                          23

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ttttaaactt ttcttttagt tgtgc                                        25

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
actcgataat ctggatgact                                              20

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
caatttagtg aaataactat aatggaac                                     28

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
agtgccactg gtctataat                                               19

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cctgtgaaat aatactggta tgt                                          23

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 78
ctactttgat atcaccacac ac                                                      22

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tagagcgtgc agataatga                                                           19

<210> SEQ ID NO 80
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tcaacaaccc ccacaaa                                                             17

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctttctctag gtgaagctgt a                                                   21

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ggttcattct ctggatcaga                                                   20

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ctgaggtgga agagacag                                                     18

<210> SEQ ID NO 84
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 84
actggttctc actcacc                                                    17

<210> SEQ ID NO 85
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gccagcaaag cagtag                                                     16

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tggaaaaata gcctcaattc t                                               21

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
caccacatta catacttacc at                                              22

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ctctggaaaa gagtaattca ca                                              22

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cgtatttata gctgatttga tgg                                             23

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 90
ggacttcacc tgacagat                                                    18

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ctttggtttc tcttggtcta g                                                21

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gagtttctgc agattgactt                                                  20

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gtgtttcctt tgcagatg                                                    18

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
tcacatgcct ctttctcta                                                   19

<210> SEQ ID NO 95
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cctggctctg actcac                                                      16

<210> SEQ ID NO 96
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
tttccctgcc aagtgat 17

<210> SEQ ID NO 97
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
tgcagcggtg ttgt 14

<210> SEQ ID NO 98
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tctcggctca aggac 15

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ttcctcagtt acaccaatct 20

<210> SEQ ID NO 100
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gcctttgggg ttacttt 17

<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gctgctggag aagagata 18

<210> SEQ ID NO 102
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
aggtggctgg ttatgtc					17

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ggagataagt gatggagatg t					21

<210> SEQ ID NO 104
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ggatcggcct cttcat					16

<210> SEQ ID NO 105
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
cccaaccaag ctctctt					17

<210> SEQ ID NO 106
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
actgacgtgc ctctc					15

<210> SEQ ID NO 107
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gcagggtctt ctctgtt					17

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ccaacagagg gaaactaata g					21

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ctgatgggga gaatgtga                                                 18

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
catttgacca tgaccatgta                                               20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cccatgaata ccagtgacta                                               20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ctgttactta cgtggacatt                                               20

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ctcattcatc gccacatag                                                19

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gacttacctt gcaatgtttg                                               20

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
actggcctgt ctcaatat                                              18

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
agtggaagta tgcccatata                                            20

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
tacagaagag gagtgtcata t                                          21

<210> SEQ ID NO 118
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
tgcccactgt gttact                                                16

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
agttgtgggt acctttagat t                                          21

<210> SEQ ID NO 120
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
ggcggtggtg gt                                                    12

```
<210> SEQ ID NO 121
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gccaggcctc aacg                                                     14

<210> SEQ ID NO 122
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gtgaccgagg acaac                                                    15

<210> SEQ ID NO 123
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ctgaccgacg ttgac                                                    15

<210> SEQ ID NO 124
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
cctgggattg cagattg                                                  17

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gtttcatgga ctcagttact                                               20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126 ccagacccttt gctttagatt                                              20

<210> SEQ ID NO 127
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
aaagacttgg tgttgttgat                                                 20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gcccatcata tttcttcaga                                                 20

<210> SEQ ID NO 129
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
cgtgccaccc agaatat                                                    17

<210> SEQ ID NO 130
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ggcctacctg gtcg                                                       14

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ttccagcact ctgacatat                                                  19

<210> SEQ ID NO 132
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
tgcttttagg gcccac                                                     16

<210> SEQ ID NO 133
<211> LENGTH: 22
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ccaacctaat agtgtattca ca                                            22

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
attattgact ctgttgtgct                                               20

<210> SEQ ID NO 135
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ccccagtcct catgtac                                                  17

<210> SEQ ID NO 136
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gctggaggag ctagag                                                   16

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ccttctcttc cccaatctac                                               20

<210> SEQ ID NO 138
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
aggagccagg catttt                                                   16

<210> SEQ ID NO 139
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 139
ctttccccac aatcatactg                                                  20

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gctggtgttg tctcaatat                                                   19

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
tacgatgcaa gagtacaca                                                   19

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ccaccactgg atttctca                                                    18

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
cttattggct ttggtcttca                                                  20

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
tcagcatcat tgtaaattat tctattt                                          27

<210> SEQ ID NO 145
<211> LENGTH: 15
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 145
acgagctgga ccact                                                    15

<210> SEQ ID NO 146
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
tcggctctcc actca                                                    15

<210> SEQ ID NO 147
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
gggccacact tactct                                                   16

<210> SEQ ID NO 148
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ccgggtctca ctca                                                     14

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cgtagtaggg gaagatcatc                                               20

<210> SEQ ID NO 150
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ggacactcgc agtagaa                                                  17

<210> SEQ ID NO 151
<211> LENGTH: 22
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 151
ataatgctcc tagtacctgt ag                                              22

<210> SEQ ID NO 152
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
cttgcacaaa tgctgaaag                                                  19

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
catttataga aaccgaggta tga                                             23

<210> SEQ ID NO 154
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gtctgcagga caattcat                                                   18

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
tccacaaagc cccttataat                                                 20

<210> SEQ ID NO 156
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
cttgtttcag gcatgtagt                                                  19

<210> SEQ ID NO 157
<211> LENGTH: 14
<212> TYPE: DNA
<213> ORGANISM: Artificial Sequence
<220> FEATURE:
<223> OTHER INFORMATION: Description of Artificial Sequence: Synthetic
```

```
                                      primer

<400> SEQUENCE: 157
cccacgccgt ctta                                                          14

<210> SEQ ID NO 158
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
agcggtggtg tagtac                                                        16

<210> SEQ ID NO 159
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
aagtgcctta gcagaga                                                       17

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
agacatcaga aagcatgatc                                                    20

<210> SEQ ID NO 161
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
ccatgaggca gagcata                                                       17

<210> SEQ ID NO 162
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
ggccatggcc tgac                                                          14

<210> SEQ ID NO 163
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 163
tatggtcatg gaagggg                                           17

<210> SEQ ID NO 164
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ccgctgagcc act                                               13

<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
gcgtcatcat ctttgtcat                                         19

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
catccctgac tgtgagat                                          18

<210> SEQ ID NO 167
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
ggtggcatgg acaga                                             15

<210> SEQ ID NO 168
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gtgggctaca agaactac                                          18

<210> SEQ ID NO 169
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 169
gggtatggac acgttcat                                                    18

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
cctcgaaatg aagctacaac                                                  20

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
aagtggagaa tgtcagtct                                                   19

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gaaactttcc acttgataag ag                                               22

<210> SEQ ID NO 173
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ttacctcgct tagtgct                                                     17

<210> SEQ ID NO 174
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
cccagagacc ccagt                                                       15

<210> SEQ ID NO 175
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
```
agccctgtcg tctct                                                    15

<210> SEQ ID NO 176
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gccaggcatt gaagtc                                                   16

<210> SEQ ID NO 177
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
gagctgctgg tgca                                                     14

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
tccaatggat ccactcac                                                 18

<210> SEQ ID NO 179
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gcatttcctt tcttcccag                                                19

<210> SEQ ID NO 180
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
ttggttacat ccctctctg                                                19

<210> SEQ ID NO 181
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
tgttgcagct gaccac                                              16

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
tgttttcctt tacttactac acc                                      23

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
tttggcttga cttgactttt                                          20

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
tgaaatgaca cttggagtaa c                                        21

<210> SEQ ID NO 185
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
gtatccacat cctcttcct                                           19

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
tggtcagtac aagcacatac                                          20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
atgggctttc ttgatgtaac                                          20

<210> SEQ ID NO 188
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ggttccgcca agagat                                                    16

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
ggccaatttc ccattctaat a                                              21

<210> SEQ ID NO 190
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
tgacaaaccg agcact                                                    16

<210> SEQ ID NO 191
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
cttcatcccc cagtaagtc                                                 19

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
ttctgggagt tttcgtatca                                                20

<210> SEQ ID NO 193
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
tccacagcca catcttt                                                   17

<210> SEQ ID NO 194
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 194
ctgacagtgc gtacatc                                                    17

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 195
tcattccaaa gtcagctatc t                                               21

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 196
aggtccacat ccattcatc                                                  19

<210> SEQ ID NO 197
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 197
cataggcatg ggtgagt                                                    17

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 198
ccttcagtcc ggttttattt g                                               21

<210> SEQ ID NO 199
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 199
cagaaagcgg tgacttact                                                  19

```
<210> SEQ ID NO 200
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
gctaatggcc cgttctc                                                  17

<210> SEQ ID NO 201
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
cccaccagac catgaga                                                  17

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
agccaatatt gtctttgtgt                                               20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ctccttctgc atggtattct                                               20

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
cattagcatc aggattatga ct                                            22

<210> SEQ ID NO 205
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ccagagccca gacctg                                                   16

<210> SEQ ID NO 206
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
ggagttacta tatgggaact gat                                           23

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
aactctgagt cttgtttcta ca                                            22

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
cctgcatgaa tttcaatgac                                               20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
gttatgcaga caccattcat                                               20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
aattgcattc acacgttaac                                               20

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
ccttgactaa atctaccatg ttt                                           23

<210> SEQ ID NO 212
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
ccagtgtctg agaacattag t                                              21

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
agacagcaca gaattgatac                                                20

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
tcagtgtatt catcgagatt tag                                            23

<210> SEQ ID NO 215
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
tgtctgcaag gtttacagt                                                 19

<210> SEQ ID NO 216
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
gctgtgcgtc actgta                                                    16

<210> SEQ ID NO 217
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
cgcaggcggc aga                                                       13

<210> SEQ ID NO 218
<211> LENGTH: 14
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 218
ggaaggcggt gttg                                                         14

<210> SEQ ID NO 219
<211> LENGTH: 14
<212> TYPE: DNA
<213> ORGANISM: Artificial Sequence
<220> FEATURE:
<223> OTHER INFORMATION: Description of Artificial Sequence: Synthetic primer

<400> SEQUENCE: 219
gcctgctgtg gccc                                                         14

<210> SEQ ID NO 220
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 220
agggcgacga gaaac                                                        15

<210> SEQ ID NO 221
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 221
tcctctagct atcttaatga ct                                                22

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 222
gcttactgga agttgacttt                                                   20

<210> SEQ ID NO 223
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 223
ggaagcaggt ggtcatt                                                      17

<210> SEQ ID NO 224
<211> LENGTH: 18
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 224
tggcttctcc tctacaga                                                   18

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
ggatgctgca gaagctataa                                                 20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
gttcaagctg aagaagatgt                                                 20

<210> SEQ ID NO 227
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
gctcagttcc tggacaaa                                                   18

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
cctttgaatg cagaagattc tt                                              22

<210> SEQ ID NO 229
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
agcagagaat gggtactc                                                   18

<210> SEQ ID NO 230
<211> LENGTH: 18
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 230
gttgtctttg gcaaggat                                                   18

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
gcactgtaat aatccagact g                                               21

<210> SEQ ID NO 232
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
gtgggagacc ttgaaca                                                    17

<210> SEQ ID NO 233
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
gccatggagt cgatgag                                                    17

<210> SEQ ID NO 234
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
gcctgacaaa tccagagta                                                  19

<210> SEQ ID NO 235
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tgatgaaccg gtcctttac                                                  19

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 236
cgacgacaat cttaaactgt a                                              21

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
acaacccact gaggtatatg                                                20

<210> SEQ ID NO 238
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
tgtatggtag gaccaccag                                                 19

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
aaacagattc ctccttgtca                                                20

<210> SEQ ID NO 240
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
gcacctgttt tgttgtgta                                                 19

<210> SEQ ID NO 241
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
cccacccgtg accg                                                      14

<210> SEQ ID NO 242
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
caggtgcagc cacaaa                                                    16

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 243
tctacctgga gattgacaac                                                20

<210> SEQ ID NO 244
<211> LENGTH: 16
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 244
caagcacccc atcaag                                                    16

<210> SEQ ID NO 245
<211> LENGTH: 13
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 245
ccggcacgct ggt                                                       13

<210> SEQ ID NO 246
<211> LENGTH: 15
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 246
ccacggtggc tacaa                                                     15

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 247
acctgtttgt tggacatact                                                20

<210> SEQ ID NO 248
<211> LENGTH: 19
<212> TYPE: DNA
<213> ORGANISM: Artificial Sequence
<220> FEATURE:
<223> OTHER INFORMATION: Description of Artificial Sequence: Synthetic
     primer

```
<400> SEQUENCE: 248
aagactcgga tgatgtacc                                                19

<210> SEQ ID NO 249
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
ggttacccca tggaactta                                                19

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
caggaagcta tccctattct                                               20

<210> SEQ ID NO 251
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
gttaccccaa cggctac                                                  17

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
tgcagatggc atcattaatc                                               20

<210> SEQ ID NO 253
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
cacccagaaa gcagacta                                                 18

<210> SEQ ID NO 254
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
```
cgacacacac gacaatac                                                    18

<210> SEQ ID NO 255
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
gtcacagcct tcttcatg                                                    18

<210> SEQ ID NO 256
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
cgcatggcct cttct                                                       15

<210> SEQ ID NO 257
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
gcaccgagac gatgaa                                                      16

<210> SEQ ID NO 258
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
gcacctggct cctct                                                       15

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
ccccatacaa tttgatgaca                                                  20

<210> SEQ ID NO 260
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260

```
tccgccgcac ttac                                                         14
```

<210> SEQ ID NO 261
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261

```
gtgagcaggt ggaagtag                                                     18
```

<210> SEQ ID NO 262
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262

```
ccagatgagc agcgt                                                        15
```

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263

```
tcttcctcct cttcttcttc                                                   20
```

<210> SEQ ID NO 264
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264

```
cagcaagtgc ccagta                                                       16
```

<210> SEQ ID NO 265
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265

```
ccgagtccag cacctc                                                       16
```

<210> SEQ ID NO 266
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266

```
aggctcccac ctttca                                                       16
```

<210> SEQ ID NO 267
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
acagaccctc tcactcat                                                   18

<210> SEQ ID NO 268
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
ccaagggtgc agttatg                                                    17

<210> SEQ ID NO 269
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
tgcctcttgc ttctctt                                                    17

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
cctcactgat tgctcttagg                                                 20

<210> SEQ ID NO 271
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
gcagctgtgg gttgat                                                     16

<210> SEQ ID NO 272
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ggcccctgtc atcttc                                                     16

<210> SEQ ID NO 273
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 273
gtcctctgac tgctcttt                                                 18

<210> SEQ ID NO 274
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 274
gctggatccc cactttt                                                  17

<210> SEQ ID NO 275
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 275
tcacgttggt ccacatc                                                  17

<210> SEQ ID NO 276
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 276
acaggatgac aggaagag                                                 18

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 277
acgatttccc ttggagatat                                               20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 278
agacaactgt tcaaactgat                                               20

```
<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
gaccccaagc tttagtaaat                                                  20

<210> SEQ ID NO 280
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
acaccctcca ttttatcac                                                   19

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
cacgaatgtg tggttaactc                                                  20

<210> SEQ ID NO 282
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
tttccttccc ccttgtc                                                     17

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
ttgtattctc tgccttctct                                                  20

<210> SEQ ID NO 284
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
aataaccgct cctcatca                                                    18

<210> SEQ ID NO 285
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
ctgagactag atgactttg tc                                              22

<210> SEQ ID NO 286
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
ctttacttaa atagggcaag ttc                                            23

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
ttcctttatt tttgttccca aag                                            23

<210> SEQ ID NO 288
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
caacgccaca accac                                                     15

<210> SEQ ID NO 289
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
gtaccagatg gatgtgaac                                                 19

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
agagacatgc atgaacattt                                                20

<210> SEQ ID NO 291
<211> LENGTH: 19
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
cttgtctctg tgttcttgt                                                   19

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
agttaacgtc ttccttctct                                                  20

<210> SEQ ID NO 293
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
gcatctgcct cacct                                                       15

<210> SEQ ID NO 294
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
agccaggaac gtactg                                                      16

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
aagggattgt gattgttcat                                                  20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
cctgatctcc ttagacaact                                                  20

<210> SEQ ID NO 297
<211> LENGTH: 17
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 297
ataccctctc agcgtac                                                      17

<210> SEQ ID NO 298
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
ggggatgagc tacctg                                                       16

<210> SEQ ID NO 299
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
ttggccagca agaatg                                                       16

<210> SEQ ID NO 300
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
cagtgcaagg tttacaca                                                     18

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
gaaaggagag caggataata a                                                 21

<210> SEQ ID NO 302
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
cactgatatt taaatgcctt agag                                              24

<210> SEQ ID NO 303
<211> LENGTH: 18
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 303
cagcagcttg gtttcttc                                                    18

<210> SEQ ID NO 304
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
tgcaacgtgt gtagaca                                                     17

<210> SEQ ID NO 305
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
tcccaaccat gacaaga                                                     17

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
gctacttgca atgatataca c                                                21

<210> SEQ ID NO 307
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
cacccaatga agaatgtaat tg                                               22

<210> SEQ ID NO 308
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
agcccagcca tttctaa                                                     17

<210> SEQ ID NO 309
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 309
ctggctgctg aagtct                                                    16

<210> SEQ ID NO 310
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
cactgtggag gcatttg                                                   17

<210> SEQ ID NO 311
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
cagtggctca agcac                                                     15

<210> SEQ ID NO 312
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
gaggagcccg tgtc                                                      14

<210> SEQ ID NO 313
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
ctgcagctgg tcctt                                                     15

<210> SEQ ID NO 314
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
gcaggagctg acagta                                                    16

<210> SEQ ID NO 315
<211> LENGTH: 17
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 315
cggtagttgc ccttctc                                                    17

<210> SEQ ID NO 316
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
cgctgtgtcc tttcag                                                     16

<210> SEQ ID NO 317
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
gacattttca aagcagtgta tc                                              22

<210> SEQ ID NO 318
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
ccagtccctc tggaataa                                                   18

<210> SEQ ID NO 319
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
ctctatagtg gggtcgtat                                                  19

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
acattattgc caacatgact                                                 20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
catactcaac acgattctgt                                                  20

<210> SEQ ID NO 322
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
ggcacggttg aatgtaa                                                     17

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
ccacatttct cttccattgt a                                                21

<210> SEQ ID NO 324
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
agacaataat tattaaaagg tgatctatt                                        29

<210> SEQ ID NO 325
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
ttagcgagtg cccatt                                                      16

<210> SEQ ID NO 326
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
tgtcccactt gattcagt                                                    18

<210> SEQ ID NO 327
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 327
cgtgagtacc cattctct                                                 18

<210> SEQ ID NO 328
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
ccaaagacaa cttcattaga ct                                            22

<210> SEQ ID NO 329
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
gtatttattt cagtgttact tacctg                                        26

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
ggatcatatt cgtccacaaa                                               20

<210> SEQ ID NO 331
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
ctttctccag ctaattcatc t                                             21

<210> SEQ ID NO 332
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
ctgcagccag aaagact                                                  17

<210> SEQ ID NO 333
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
```
tcctctcgtt tccttacat                                             19

<210> SEQ ID NO 334
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
caaagcaagc cagattct                                              18

<210> SEQ ID NO 335
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
gcactgggtc aaagtct                                               17

<210> SEQ ID NO 336
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
cagtgctaac caagttctt                                             19

<210> SEQ ID NO 337
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
cgctcctggg aatct                                                 15

<210> SEQ ID NO 338
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
cagtcaaggt tgctgatt                                              18

<210> SEQ ID NO 339
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339

```
ggcgtcagga actg                                               14

<210> SEQ ID NO 340
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
cggcctcgat cttgta                                             16

<210> SEQ ID NO 341
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
cagctcctcc tcgc                                               14

<210> SEQ ID NO 342
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
ggtgggatca tattcatcta c                                       21

<210> SEQ ID NO 343
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
gtctgaactg aagataatga ct                                      22

<210> SEQ ID NO 344
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
tgtccaccgt gatctg                                             16

<210> SEQ ID NO 345
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
tcgtctggga actatactc                                          19
```

```
<210> SEQ ID NO 346
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
tgtactgctc ccagaaga                                                 18

<210> SEQ ID NO 347
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
tgcaccagga gtttgta                                                  17

<210> SEQ ID NO 348
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
gagggtgtcc tgtgt                                                    15

<210> SEQ ID NO 349
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
gccacagcag tctgaaa                                                  17

<210> SEQ ID NO 350
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
aggttcgctg cttttaatc                                                19

<210> SEQ ID NO 351
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
cccgggggat taaagc                                                   16
```

<210> SEQ ID NO 352
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 352
ggtcagctac tcctcttc                                                 18

<210> SEQ ID NO 353
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 353
cccctccttc ctagaga                                                  17

<210> SEQ ID NO 354
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 354
gtgctgcatt tcagagaa                                                 18

<210> SEQ ID NO 355
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 355
gtgcagaaca tcaagttca                                                19

<210> SEQ ID NO 356
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 356
tggctttgtg ctcattac                                                 18

<210> SEQ ID NO 357
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 357
ctgctctcag gttgact                                                  17

<210> SEQ ID NO 358
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
gagctgggga ctctt                                                          15

<210> SEQ ID NO 359
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
caggagtcat gactctgtt                                                      19

<210> SEQ ID NO 360
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
tggcctttga cctcaat                                                        17

<210> SEQ ID NO 361
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
gcccgcaggt actt                                                           14

<210> SEQ ID NO 362
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
atcctccggc tgaag                                                          15

<210> SEQ ID NO 363
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
ctggagtgag ccctg                                                          15

<210> SEQ ID NO 364

-continued

```
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
gcagtgctag gaaagag                                                  17

<210> SEQ ID NO 365
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
tgcagggtgg caa                                                      13

<210> SEQ ID NO 366
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
cgtcatgtgc tgtgac                                                   16

<210> SEQ ID NO 367
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
gtgtttctgt catccaaata c                                             21

<210> SEQ ID NO 368
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
tgccctggta ggttttc                                                  17

<210> SEQ ID NO 369
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369 caaggggac tgtagat                                                   17

<210> SEQ ID NO 370
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
ggtctgacgg gtagagt                                                      17

<210> SEQ ID NO 371
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
tctgtctccc cacagag                                                      17

<210> SEQ ID NO 372
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
tgaagtgtgc tctgaaca                                                     18

<210> SEQ ID NO 373
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
atgcttgctc tgatagga                                                     18

<210> SEQ ID NO 374
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
acacaagact cagaatagat aca                                               23

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
atgtctcttc ttcctacctg                                                   20

<210> SEQ ID NO 376
<211> LENGTH: 17
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 376
gccacacgtg gtattca                                                     17

<210> SEQ ID NO 377
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
tgagctccct acctgatt                                                    18

<210> SEQ ID NO 378
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
caccttctcc agcattttc                                                   19

<210> SEQ ID NO 379
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
catcatcctc acctgactc                                                   19

<210> SEQ ID NO 380
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
ttcaaaatgt agaccacaga c                                                21

<210> SEQ ID NO 381
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
cggaagaact ctccagtatt c                                                21

<210> SEQ ID NO 382
<211> LENGTH: 19
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 382
ccttgttgaa ggagcagaa                                                  19

<210> SEQ ID NO 383
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
ccagagcccg actcg                                                      15

<210> SEQ ID NO 384
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
tctccaagat gggatactc                                                  19

<210> SEQ ID NO 385
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
ggcgtctgcg tacttc                                                     16

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
cagggacctt accttataca                                                 20

<210> SEQ ID NO 387
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
cccccacaca gcaaa                                                      15

<210> SEQ ID NO 388
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 388
gtatctccct tccctgatta c                                              21

<210> SEQ ID NO 389
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
tggtccctgg tgtca                                                     15

<210> SEQ ID NO 390
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
aggcgttctc ctttctc                                                   17

<210> SEQ ID NO 391
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
gcagtgagtg ggtacctc                                                  18

<210> SEQ ID NO 392
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
ccggacatgg tctaagag                                                  18

<210> SEQ ID NO 393
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
ccatctgcat ggtactct                                                  18

<210> SEQ ID NO 394
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 394
gtgctctcat tttaaagatg g                                              21

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
gcttgtttgc tgaatgttaa c                                              21

<210> SEQ ID NO 396
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
gtgtgcagaa caatgtga                                                  18

<210> SEQ ID NO 397
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
ggacttcaag aacttggatt a                                              21

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
actatgggac ttgaaaacgg                                                20

<210> SEQ ID NO 399
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
acaggccagt gtttacat                                                  18

<210> SEQ ID NO 400
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 400
aacatcatca ttagtggatc tac                                           23

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
tgtgatcaca tgcttacagt                                               20

<210> SEQ ID NO 402
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
gagaaattgc ttgctttaga tg                                            22

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
gtgtcagaga tggagatgat                                               20

<210> SEQ ID NO 404
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
agcgcctgga agaga                                                    15

<210> SEQ ID NO 405
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
ggcatgaggt cactgac                                                  17

<210> SEQ ID NO 406
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 406
gctccaaccc ctagac                                                     16

<210> SEQ ID NO 407
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
acaccaggtc cttgaag                                                    17

<210> SEQ ID NO 408
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
gggatgccac tcacag                                                     16

<210> SEQ ID NO 409
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
ggaagctggc aatctcta                                                   18

<210> SEQ ID NO 410
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
cccgttctac gagaagaata a                                               21

<210> SEQ ID NO 411
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
gcccacctcg ttgt                                                       14

<210> SEQ ID NO 412
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
```

```
ccctaagttt gtaagtagtg c                                              21
```

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413

```
agaagcaaag cgttctttac                                                20
```

<210> SEQ ID NO 414
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414

```
agaccctgta ggaggac                                                   17
```

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415

```
tggcaccata cgaaatattc                                                20
```

<210> SEQ ID NO 416
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416

```
ccggatcagt gcataaca                                                  18
```

<210> SEQ ID NO 417
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417

```
atcatgactg atatggtaga ca                                             22
```

<210> SEQ ID NO 418
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
tctggagaga gaacaaataa atg                    23

<210> SEQ ID NO 419
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
actcagcctg tttctgg                           17

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
cctgacagac aataaaaggc                        20

<210> SEQ ID NO 421
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
gcttgatagg taggtactca                        20

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
catgcaaatt ttgctgaagt                        20

<210> SEQ ID NO 423
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
ccttccttga tcatcttgta ga                     22

<210> SEQ ID NO 424
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
agttaaggac tctgaagatg t                      21

<210> SEQ ID NO 425
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 425
gtgtgacatg ttctaatata gtca                                          24

<210> SEQ ID NO 426
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 426
gctccatgca gatactga                                                 18

<210> SEQ ID NO 427
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 427
cctggcaccc aaacat                                                   16

<210> SEQ ID NO 428
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 428
gcttcccaaa cacttagac                                                19

<210> SEQ ID NO 429
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 429
aagcagtgct catgattg                                                 18

<210> SEQ ID NO 430
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 430
ttgggcttac acttcgg                                                  17

<210> SEQ ID NO 431
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 431
aaccacaaaa gtatactcca tg                                          22

<210> SEQ ID NO 432
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 432
ggatggctgg cttaca                                                 16

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 433
catctgactt ggtggtaaac                                             20

<210> SEQ ID NO 434
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 434
cggagcttcc tgagtg                                                 16

<210> SEQ ID NO 435
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 435
gcccctctct gattgtc                                                17

<210> SEQ ID NO 436
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 436
ggtggtggtg ctgatg                                                 16

```
<210> SEQ ID NO 437
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 437
cgccaattaa ccctgatta                                                  19

<210> SEQ ID NO 438
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
ggatttaagc ctgattgaac a                                               21

<210> SEQ ID NO 439
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
accagtgagg gaagtga                                                    17

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 440
ggtaaatgga caagaacact                                                 20

<210> SEQ ID NO 441
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
gcccagttcc ctttctac                                                   18

<210> SEQ ID NO 442
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442
tctggctgcg agttataat                                                  19

<210> SEQ ID NO 443
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 443
cagctttgcc catgaaac                                                18

<210> SEQ ID NO 444
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 444
ccaggcagcg gtagta                                                  16

<210> SEQ ID NO 445
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445
gctactggcc ggaaag                                                  16

<210> SEQ ID NO 446
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 446
tcagatgtgc tgttgagac                                               19

<210> SEQ ID NO 447
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
aggatggcct ctgtct                                                  16

<210> SEQ ID NO 448
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
gagcaacacc cacactta                                                18

<210> SEQ ID NO 449
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
cagctggcct taccat                                                       16

<210> SEQ ID NO 450
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 450
gtagctgtgc atgtcct                                                      17

<210> SEQ ID NO 451
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451
ggaggtgggt gtctttat                                                     18

<210> SEQ ID NO 452
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 452
gtcgtgggac acagtg                                                       16

<210> SEQ ID NO 453
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453
ggtgcgggag tgaatag                                                      17

<210> SEQ ID NO 454
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454
ggagggtgca gtgttg                                                       16

<210> SEQ ID NO 455
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 455
ctccagaagc ttgaactct                                                  19

<210> SEQ ID NO 456
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
ctagcacgtg cctacc                                                     16

<210> SEQ ID NO 457
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
cctgagtgta gatgatgtca                                                 20

<210> SEQ ID NO 458
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
actcaggtac tgtgtatata ctt                                             23

<210> SEQ ID NO 459
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
gaagagaatc tccgcaag                                                   18

<210> SEQ ID NO 460
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
gcactggcct catcttg                                                    17

<210> SEQ ID NO 461
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 461
gccctgactt tcaactct                                                   18

<210> SEQ ID NO 462
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462
agcgctgctc agatag                                                     16

<210> SEQ ID NO 463
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
acccaggtcc agatgaa                                                    17

<210> SEQ ID NO 464
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464
actgactttc tgctcttgt                                                  19
```

METHODS FOR SCREENING SOLID TUMORS FOR MUTATIONS

CROSS-REFERENCE TO RELATED APPLICATIONS

This application is a National Stage Application of PCT/US2015/057733, filed Oct. 28, 2015 which claims the benefit of and priority to U.S. Application No. 62/166,996, filed May 27, 2015, and to U.S. Application No. 62/246,895, filed Oct. 27, 2015, the contents of which are incorporated herein by reference in their entireties.

SEQUENCE LISTING

The instant application contains a Sequence Listing which has been submitted in ASCII format via EFS-WEB and is hereby incorporated by reference in its entirety. Said ASCII copy, created on Nov. 8, 2017, is named 034827-0437 SL.txt and is 104 KB.

TECHNICAL FIELD

The present technology relates to methods for determining whether a patient diagnosed with breast cancer, colorectal cancer, melanoma or lung cancer will benefit from or is predicted to be responsive to treatment with a therapeutic agent alone or in a specific combination with other therapeutic agents. These methods are based on screening a patient's solid tumors and detecting alterations in target nucleic acid sequences corresponding to a specific set of cancer-related genes. Kits for use in practicing the methods are also provided.

BACKGROUND

The following description of the background of the present technology is provided simply as an aid in understanding the present technology and is not admitted to describe or constitute prior art to the present technology.

The development of companion diagnostics has the potential to improve patient outcomes, and eliminate the need for insurers to pay for expensive yet ineffective therapies. As the number of genes implicated in cancer continues to grow, it is becoming evident that a careful characterization of the genetic alterations that define an individual patient's tumors will often be useful in determining optimal therapeutic strategies. For example, Foundation Medicine® offers a large-scale solid tumor screening panel that interrogates the entire coding sequence of over 300 cancer-related genes and 28 gene rearrangements using DNA or RNA bait libraries (e.g., FoundationOne®). Such assays require a tumor DNA input of at least 50 ng. However, the amount of DNA available for such comprehensive studies is often limited and of poor quality because the tumor DNA is isolated from formalin fixed paraffin-embedded (FFPE) tissues. The FFPE process frequently degrades DNA into small fragments and has the potential to damage the DNA base pairs themselves.

TruSight™ Tumor (Illumina, Inc.) is an example of an existing PCR-based NGS tumor screening panel that interrogates a narrower set of cancer-related genes (174 amplicons within 26 genes) and requires a minimum DNA input of 30 ng. However, this method requires an evaluation of the quality of genomic DNA extracted from the FFPE tumor sample via quantitative PCR prior to generating an amplicon-based library because neither tissue area nor DNA yield are adequate predictors of library performance. See TruSight™ Tumor Data Sheet (Illumina, Inc.); Generating Sequencing Libraries from FFPE Samples, White Paper (Illumina, Inc.).

Detecting actionable genetic alterations in FFPE tissues is further complicated by the fact that cells within a tumor sample can exhibit a high degree of molecular variation between tumors (inter-tumor heterogeneity) and within the individual tumor itself (intra-tumor heterogeneity). Tumor heterogeneity has been observed in leukemias, melanomas, breast, prostate, colon, lung, and gynecological carcinomas. Accordingly, the small fraction of cells in a biopsy may not be representative of the entire tumor mass, which could lead to false negative calls for a given genetic alteration.

Intra-tumor heterogeneity may also explain, at least in part, why some patients who initially respond well to a cancer drug eventually relapse, often with new tumors that no longer respond to the therapy. The higher the diversity of cells within a tumor, the greater the risk that an occasional cell might be able to adapt to the type of stress a drug imposes. Acquired resistance to cancer drugs may develop through a variety of mechanisms (Chong C. & Janne P., *Nat. Med.* 19: 1389-1400 (2013); Katayama et al., *Sci. Transl. Med.* 4(120): 120ra17 (2012)). For example, resistant cells can develop a compensatory signaling pathway, or "bypass track," that reestablishes activation of key downstream proliferation and survival signals despite inhibition of the original oncogene (Niederst & Engelman, Sci. Signal. 6: re6 (2013)). Thus, the heterogeneity of cancer cells introduces significant challenges in designing effective treatment strategies, especially when a specific gene mutation is not detected in the biopsy.

Thus, there is a substantial need for more robust and sensitive methods that effectively detect the presence of genetic alterations in highly heterogeneous tumors samples, particularly in FFPE tissues. Such methods would aid in predicting the responsiveness of individual patients to a particular drug regimen and the identification of optimal therapeutic strategies at the outset.

SUMMARY OF THE PRESENT TECHNOLOGY

The methods and compositions disclosed herein relate to the detection of mutations that are predictive of the responsiveness of a subject diagnosed with breast cancer, colorectal cancer, melanoma, or lung cancer to a particular therapeutic regimen. In another aspect, the methods and compositions of the present technology are useful in selecting or designing an optimal therapeutic regimen for a subject diagnosed with breast cancer, colorectal cancer, melanoma, or lung cancer. It is contemplated that the methods disclosed herein allow for rapid and sensitive detection of mutations in the target nucleic acid sequences of AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN. In some embodiments, the therapeutic regimen comprises one or more of anti-HER-2 therapies, PI3K/AKT/mTor pathway inhibitors, receptor tyrosine kinase inhibitors (TKIs), Notch pathway inhibitors, BRAF inhibitors, SMO antagonists, ALK MET inhibitors, ERBB2 antagonists, FGFR3 antagonists, and RAF/MEK/ERK inhibitors.

In one aspect, the present disclosure provides a method for detecting at least one mutation in a plurality of cancer-related genes in a subject comprising (a) extracting genomic DNA from a formalin fixed paraffin-embedded tumor sample obtained from the subject; (b) generating a library comprising amplicons corresponding to each of the plurality of cancer-related genes, said plurality of cancer-related genes comprising AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN, wherein (i) generating said library occurs without the use of a bait set comprising nucleic acid sequences that are complementary to at least one of the plurality of amplicons; and (ii) the quality of the genomic DNA extracted from the formalin fixed paraffin-embedded tumor sample is not assessed using quantitative PCR prior to generating the library; (c) ligating an adapter sequence to the ends of the plurality of amplicons; and (d) detecting at least one mutation in at least one of the plurality of amplicons using high throughput massive parallel sequencing.

In some embodiments of the method, the plurality of amplicons is generated by at least two primer pairs disclosed in Table 1, Table 2, or a combination thereof.

In some embodiments of the method, the at least one mutation detected is a mutation in EGFR, KRAS, BRAF, NRAS, ERBB2 or PIK3CA. In one embodiment, the at least one mutation detected is selected from the group consisting of BRAF V600E, BRAF V600K, BRAF K483Q, BRAF G466V, BRAF G464V, BRAF E501V, BRAF E501K, EGFR ΔE746_A750, EGFR R680Q, EGFR G598E, KRAS A146T, KRAS R68M, KRAS L19F, KRAS G12V, KRAS G12D, KRAS G12C, KRAS G13D, KRAS G13C, KRAS G12A, KRAS G12S, KRAS Q22K, NRAS Q61K, NRAS Q61R, NRAS G12R, NRAS G12D, PIK3CA C420R, PIK3CA G106R, PIK3CA R38H, PIK3CA E453K, PIK3CA H1044R, PIK3CA N1044K, PIK3CA E545K, PIK3CA Q546H, PIK3CA H1047R, PIK3CA H1043L, PIK3CA M1043V, PIK3CA E542K, PIK3CA E542Q, PIK3CA T1053A, PIK3CA 1121V, PIK3CA H1047L, ERBB2 L755S, ERBB2 S310Y, ERBB2 D769Y, ERBB2 S255R, DDR2 H92Y, DDR2 R31L, DDR2 L34P, DDR2 P381R and DDR2 K392N.

In some embodiments of the method, the library comprising amplicons corresponding to each of the plurality of cancer-related genes is generated using no more than 10 ng of extracted genomic DNA from the formalin fixed paraffin-embedded tumor sample.

In some embodiments of the method, the library comprising amplicons corresponding to each of the plurality of cancer-related genes is generated using 11-25 ng of extracted genomic DNA from the formalin fixed paraffin-embedded tumor sample.

In certain embodiments, the high throughput massive parallel sequencing is performed using pyrosequencing, reversible dye-terminator sequencing, SOLiD sequencing, Ion semiconductor sequencing, Helioscope single molecule sequencing, sequencing by synthesis, sequencing by ligation, or SMRT™ sequencing.

In some embodiments of the method, the adapter sequence is a P5 adapter, P7 adapter, P1 adapter, A adapter, or Ion Xpress™ barcode adapter.

Additionally or alternatively, in some embodiments, the plurality of amplicons further comprises a unique index sequence.

In some embodiments, the formalin fixed paraffin-embedded tumor sample is a heterogeneous tumor. In certain embodiments, 5% of the cells of the heterogeneous tumor harbor at least one mutation in at least one of the plurality of amplicons.

In some embodiments of the method, the subject has been diagnosed with breast cancer, melanoma, colorectal cancer or lung cancer.

In another aspect, the present disclosure provides a method for selecting a subject for treatment with a PI3K/AKT/mTor pathway inhibitor and at least one additional agent comprising (a) extracting genomic DNA from a formalin fixed paraffin-embedded specimen obtained from the subject; (b) generating a library comprising amplicons corresponding to each of a plurality of cancer-related genes, said plurality of cancer-related genes comprising AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN, wherein (i) generating said library occurs without the use of a bait set comprising nucleic acid sequences that are complementary to at least one of the plurality of amplicons, and (ii) the quality of the genomic DNA extracted from the formalin fixed paraffin-embedded specimen is not assessed using quantitative PCR prior to generating the library; (c) detecting at least one mutation in at least one of the plurality of amplicons; and (d) selecting the subject for treatment with a PI3K/AKT/mTor pathway inhibitor and at least one additional agent, if a mutation in at least one of the amplicons corresponding to PIK3CA, PIK3R1 and PTEN, and a mutation in at least one of the amplicons corresponding to NOTCH1, ERBB2, BRAF, PTCH1, SMO, EGFR, KRAS, DDR2, MAP2K1, FGFR3, NRAS, MET, and FBXW7 are detected.

In some embodiments of the method, the amplicons corresponding to PIK3CA are generated by a pair of primers selected from the group consisting of 5' CCTAGTAGAAT-GTTTACTACCAA 3' (SEQ ID NO.: 1) and 5' CTGCTTCT-TGAGTAACACTT 3' (SEQ ID NO.: 2); 5' CATGTTCAT-GCTGTGTATGT 3' (SEQ ID NO.: 3) and 5' GCTTCTTTACAAACGTTCAGAA 3' (SEQ ID NO.: 4); 5' TCTATGTTCGAACAGGTATCT 3' (SEQ ID NO.: 5) and 5' ACTGCTAAACACTAATATAACCTTTG 3' (SEQ ID NO.: 6); 5' TTGAAATGTGTTTTATAATTTAGACTAGT 3' (SEQ ID NO.: 7) and 5' CCATGAGGTACTGGCC 3' (SEQ ID NO.: 8); 5' TTGGTGTTACTGGATCAAATC 3' (SEQ ID NO.: 9) and 5' TGCTGAACCAGTCAAACT 3' (SEQ ID NO.: 10); 5' TATTATTTTATTTTACAGAGTAACA-GACTAG 3' (SEQ ID NO.: 11) and 5' TTTAGCACTTAC-CTGTGACT 3' (SEQ ID NO.: 12); 5' TGGAATGCCA-GAACTACA 3' (SEQ ID NO.: 13) and 5' GTGGAAGATCCAATCCATTTT 3' (SEQ ID NO.: 14); 5' GGAATGAATGGCTGAATTATG 3' (SEQ ID NO.: 15) and 5' GCGGTATAATCAGGAGTTTT 3' (SEQ ID NO.: 16); 5' AGTTGGCCTGAATCACTATA 3' (SEQ ID NO.: 17) and 5' GATGTTACTATTGTGACGATCTC 3' (SEQ ID NO.: 18); 5' GTAAGTGTTACTCAAGAAGC 3' (SEQ ID NO.: 19) and 5' ATAGGATATTGTATCATACCAATTTCT 3' (SEQ ID NO.: 20); 5' TCCACAGCTACACCATATAT 3' (SEQ ID NO.: 21) and 5' AGCATCAGCATTTGACTTTA 3' (SEQ ID NO.: 22); 5' TACACAGACACTCTAGTATCTG 3' (SEQ ID NO.: 23) and 5' GAAGGTTTGACTGCCATAAA 3' (SEQ ID NO.: 24); 5' ATGACAAAGAACAGCTCAAA 3' (SEQ ID NO.: 25) and 5' GAGATCAGCCAAATTCAGTT 3' (SEQ ID NO.: 26); 5' GATGTGTTACAAGGCTTATCTA 3' (SEQ ID NO.: 27) and 5' GCCTCTTGCTCAGTTTTATC 3' (SEQ ID NO.: 28); 5' GAGGCTTTGGAGTATTTCA 3' (SEQ ID NO.: 29) and 5' CTGCTGAGAGTTATTAACAGT 3' (SEQ ID NO.: 30); and 5' GCTTTTGGAGTCCTATTGT 3' (SEQ ID NO.: 31) and 5' CACAAACTAGAGTCACA-CAC 3' (SEQ ID NO.: 32).

In some embodiments of the method, the amplicons corresponding to PIK3R1 are generated by a pair of primers selected from the group consisting of 5' GGGTTTTGGGCT-GATATTA 3' (SEQ ID NO.: 33) and 5' CCACAGAACT-GAAGGTTAAT 3' (SEQ ID NO.: 34); 5' TTATCCATT-GAATTTATTTTAATCTTTCTAG 3' (SEQ ID NO.: 35) and 5' GGGATGTGCGGGTATATT 3' (SEQ ID NO.: 36); 5' GTCTTGCAGTAAGAGATTGT 3' (SEQ ID NO.: 37) and 5' TCTTTGCTGTACCGCT 3' (SEQ ID NO.: 38); 5' GTTTCTTTTGCCTGCA 3' (SEQ ID NO.: 39) and 5' TGGATAAGGTCTGGTTTAATG 3' (SEQ ID NO.: 40); 5' GCTACAATTCAGGATGAGTTA 3' (SEQ ID NO.: 41) and 5' TCTTCTGCTATCACCATCTTT 3' (SEQ ID NO.: 42); 5' CCATCATGATGAGAAGACAT 3' (SEQ ID NO.: 43) and 5' TTGCTGGAGATACATACACT 3' (SEQ ID NO.: 44); 5' GTGGTCACTAAACCTTAAGA 3' (SEQ ID NO.: 45) and 5' GGCTTACCTTAGTGTAAGAG 3' (SEQ ID NO.: 46); 5' TTTCATCGAGATGGGAAATATG 3' (SEQ ID NO.: 47) and 5' ACCTGTTGGTATTTGGATACT 3' (SEQ ID NO.: 48); 5' AGAAGATAATATTGAAGCTGTAGG 3' (SEQ ID NO.: 49) and 5' AGAACTCTTATTTTTTAATCT-GATTTTCA 3' (SEQ ID NO.: 50); 5' GGACAGCTATT-GAAGCATTTA 3' (SEQ ID NO.: 51) and 5' CACAAGAACAAGGGAAACAC 3' (SEQ ID NO.: 52); 5' GCAGGCAGCTGAGTATC 3' (SEQ ID NO.: 53) and 5' TCATCCTGAATTGTAGCAATCA 3' (SEQ ID NO.: 54).

In some embodiments of the method, the amplicons corresponding to PTEN are generated by a pair of primers selected from the group consisting of 5' CAGCTTCTGC-CATCTCT 3' (SEQ ID NO.: 55) and 5' AGCAGCCGCA-GAAAT 3' (SEQ ID NO.: 56); 5' GTGGCTTTTTGTTT-GTTTG 3' (SEQ ID NO.: 57) and 5' CACTCTAACAAGCAGATAACT 3' (SEQ ID NO.: 58); 5' TACTTGTTAATTAAAAATTCAAGAGTTTT 3' (SEQ ID NO.: 59) and 5' CTTAGCCATTGGTCAAGATC 3' (SEQ ID NO.: 60); 5' ACAATCATGTTGCAGCA 3' (SEQ ID NO.: 61) and 5' AAAAACATCAAAAAATAACTTACCTTTT 3' (SEQ ID NO.: 62); 5' AGAGGCGCTATGTGTATTA 3' (SEQ ID NO.: 63) and 5' CATGGAAGGAT-GAGAATTTCA 3' (SEQ ID NO.: 64); 5' GGAAGA-CAAGTTCATGTACT 3' (SEQ ID NO.: 65) and 5' CTGTC-CTTATTTTGGATATTTCTC 3' (SEQ ID NO.: 66); 5' ATTAATTAAATATGTCATTTCATTTCTTTTTC 3' (SEQ ID NO.: 67) and 5' GCTATCGATTTCTTGATCACA 3' (SEQ ID NO.: 68); 5' TGAGTCATATTTGTGGGTTTTC 3' (SEQ ID NO.: 69) and 5' TGATCAGGTTCATTGT-CACTAA 3' (SEQ ID NO.: 70); 5' TTTGATTGCTGCAT-ATTTCAG 3' (SEQ ID NO.: 71) and 5' TCAAAGCATTCT-TACCTTACTAC 3' (SEQ ID NO.: 72); 5' TTTTAAACTTTTCTTTTAGTTGTGC 3' (SEQ ID NO.: 73) and 5' ACTCGATAATCTGGATGACT 3' (SEQ ID NO.: 74); 5' CAATTTAGTGAAATAACTATAATGGAAC 3' (SEQ ID NO.: 75) and 5' AGTGCCACTGGTCTATAAT 3' (SEQ ID NO.: 76); 5' CCTGTGAAATAATACTGGTATGT 3' (SEQ ID NO.: 77) and 5' CTACTTTGATATCACCACA-CAC 3' (SEQ ID NO.: 78); 5' TAGAGCGTGCAGA-TAATGA 3' (SEQ ID NO.: 79) and 5' TCAACAAC-CCCCACAAA 3' (SEQ ID NO.: 80); and 5' CTTTCTCTAGGTGAAGCTGTA 3' (SEQ ID NO.: 81) and 5' GGTTCATTCTCTGGATCAGA 3' (SEQ ID NO.: 82).

In some embodiments of the method, the formalin fixed paraffin-embedded specimen is a heterogeneous tumor. In certain embodiments, 5%-10% of the cells of the heterogeneous tumor harbor at least one mutation in at least one of the plurality of amplicons. In other embodiments, at least 10% of the cells of the heterogeneous tumor harbor at least one mutation in at least one of the plurality of amplicons.

In some embodiments of the method, the PI3K/AKT/mTor pathway inhibitor is selected from the group consisting of BKM120, BEZ235, Pictilisib (GDC-0941), LY294002, CAL-101 (Idelalisib), GNE-317, PI-3065, HS-173, PI-103, NU7441, GSK2636771, VS-5584, CZC24832, Duvelisib, TG100-115, A66, YM201636, CAY10505, GSK1059615, PF-04691502, PIK-75, PIK-93, AS-605240, BGT226, AZD6482, Voxtalisib, Alpelisib, CUDC-907, IC-87114, Omipalisib, TG100713, Gedatolisib, CH5132799, PKI-402, BAY 80-6946, TGX-221, XL147, PIK-90, PIK-293, PIK-294, 3-Methyladenine, Quercetin, Wortmannin, ZSTK474, AS-252424, AS-604850, everolimus, and Apitolisib.

In one particular embodiment, the subject is diagnosed as having HER-2 negative breast cancer. In some embodiments of the method, the at least one additional agent is selected from the group consisting of Notch pathway inhibitors, BRAF inhibitors, SMO antagonists, MET inhibitors, and ERBB2 antagonists. In certain embodiments, the Notch pathway inhibitors are selected from the group consisting of FLI-06, LY411575, Dibenzazepine, RO4929097, Compound E, Z-Leu-Leu-Nle-CHO, SAHM1, TR4 and Semagacestat. In some embodiments, the SMO antagonists are selected from the group consisting of Purmorphamine, Taladegib (LY2940680), Cyclopamine, Vismodegib (GDC-0449), LDE225, Glasdegib (PF-04449913), PF-5274857, TAK-441, SANT-1, BMS-833923, GANT61 and IPI-926.

In some embodiments, the ERBB2 antagonists are selected from the group consisting of Lapatinib, Canertinib, CP-724,714, AZD8931, AEE788, Tyrphostin AG 879, Mubritinib, and Pertuzumab. In certain embodiments, the BRAF inhibitors are selected from the group consisting of GDC-0879, SB590885, Encorafenib, RAF265, TAK-632, PLX4720, CEP-32496, AZ628, Sorafenib Tosylate, Sorafenib, Vemurafenib (Zelboraf) and Dabrafenib (GSK2118436).

In some embodiments of the method, the subject is diagnosed as having colorectal cancer. In a further embodiment, the at least one additional agent is selected from the group consisting of Notch pathway inhibitors, FGFR3 antagonists, and RAF/MEK/ERK inhibitors. In certain embodiments, the RAF/MEK/ERK inhibitors are selected from the group consisting of Vemurafenib (Zelboraf) and Dabrafenib (GSK2118436), Encorafenib, TAK-632, PLX4720, MLN2480, Cobimetinib (GDC-0973), MEK 162, RO5126766, GDC-0623, VTXIIe, Selumetinib (AZD6244), PD0325901, Trametinib (GSK1120212), U0126-EtOH, PD184352 (CI-1040), Refametinib, PD98059, BIX02189, Binimetinib, Pimasertib (AS-703026), SL327, BIX02188, AZD8330, TAK-733, PD318088, SCH772984, and FR 180204.

In some embodiments, the Notch pathway inhibitors are selected from the group consisting of FLI-06, LY411575, Dibenzazepine, RO4929097, Compound E, Z-Leu-Leu-Nle-CHO, SAHM1, TR4 and Semagacestat. In certain embodiments, the FGFR3 antagonists are selected from the group consisting of BGJ398 (NVP-BGJ398), AZD4547, LY2874455, Dovitinib Dilactic acid, Dovitinib, Dovitinib Lactate, CH5183284, and Nintedanib.

In one particular embodiment, a mutation in at least one of the amplicons corresponding to BRAF, MAP2K1 and NRAS and a mutation in at least one of the amplicons corresponding to FGFR3 and SMO are detected. In a further embodiment, the subject is diagnosed as having melanoma.

In some embodiments, the at least one additional agent is RAF/MEK/ERK inhibitors, FGFR3 antagonists, SMO antagonists or a combination thereof.

In one aspect, the present disclosure provides a method for predicting the likelihood of lack of responsiveness to treatment with an anti-HER-2 therapy in a HER-2 positive subject diagnosed as having breast cancer comprising: (a) extracting genomic DNA from a formalin fixed paraffin-embedded specimen obtained from the HER-2 positive subject; (b) generating a library comprising amplicons corresponding to each of a plurality of cancer-related genes, said plurality of cancer-related genes comprising AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STKl1, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN, wherein (i) generating said library proceeds independently of using a bait set comprising nucleic acid sequences that are complementary to at least one of the plurality of amplicons, and (ii) the quality of the genomic DNA extracted from the formalin fixed paraffin-embedded specimen is not assessed using quantitative PCR prior to generating the library; (c) detecting at least one mutation in at least one of the plurality of amplicons; and (d) identifying the HER-2 positive subject as having a likelihood of lack of responsiveness to treatment with an anti-HER-2 therapy, when a mutation in at least one of the amplicons corresponding to PIK3CA, PIK3R1 and PTEN is detected. In some embodiments of the method, the anti-HER-2 therapy is trastuzumab or lapatinib.

In some embodiments of the method, the amplicons corresponding to PIK3CA are generated by a pair of primers selected from the group consisting of 5' CCTAGTAGAAT-GTTTACTACCAA 3' (SEQ ID NO.: 1) and 5' CTGCTTCT-TGAGTAACACTT 3' (SEQ ID NO.: 2); 5' CATGTTCAT-GCTGTGTATGT 3' (SEQ ID NO.: 3) and 5' GCTTCTTTACAAACGTTCAGAA 3' (SEQ ID NO.: 4); 5' TCTATGTTCGAACAGGTATCT 3' (SEQ ID NO.: 5) and 5' ACTGCTAAACACTAATATAACCTTTG 3' (SEQ ID NO.: 6); 5' TTGAAATGTGTTTTATAATTTAGACTAGT 3' (SEQ ID NO.: 7) and 5' CCATGAGGTACTGGCC 3' (SEQ ID NO.: 8); 5' TTGGTGTTACTGGATCAAATC 3' (SEQ ID NO.: 9) and 5' TGCTGAACCAGTCAAACT 3' (SEQ ID NO.: 10); 5' TATTATTTTATTTTACAGAGTAACA-GACTAG 3' (SEQ ID NO.: 11) and 5' TTTAGCACTTAC-CTGTGACT 3' (SEQ ID NO.: 12); 5' TGGAATGCCA-GAACTACA 3' (SEQ ID NO.: 13) and 5' GTGGAAGATCCAATCCATTTT 3' (SEQ ID NO.: 14); 5' GGAATGAATGGCTGAATTATG 3' (SEQ ID NO.: 15) and 5' GCGGTATAATCAGGAGTTTT 3' (SEQ ID NO.: 16); 5' AGTTGGCCTGAATCACTATA 3' (SEQ ID NO.: 17) and 5' GATGTTACTATTGTGACGATCTC 3' (SEQ ID NO.: 18); 5' GTAAGTGTTACTCAAGAAGC 3' (SEQ ID NO.: 19) and 5' ATAGGATATTGTATCATACCAATTTCT 3' (SEQ ID NO.: 20); 5' TCCACAGCTACACCATATAT 3' (SEQ ID NO.: 21) and 5' AGCATCAGCATTTGACTTTA 3' (SEQ ID NO.: 22); 5' TACACAGACACTCTAGTATCTG 3' (SEQ ID NO.: 23) and 5' GAAGGTTTGACTGCCATAAA 3' (SEQ ID NO.: 24); 5' ATGACAAAGAACAGCTCAAA 3' (SEQ ID NO.: 25) and 5' GAGATCAGCCAAATTCAGTT 3' (SEQ ID NO.: 26); 5' GATGTGTTACAAGGCTTATCTA 3' (SEQ ID NO.: 27) and 5' GCCTCTTGCTCAGTTTTATC 3' (SEQ ID NO.: 28); 5' GAGGCTTTGGAGTATTTCA 3' (SEQ ID NO.: 29) and 5' CTGCTGAGAGTTATTAACAGT 3' (SEQ ID NO.: 30); and 5' GCTTTTGGAGTCCTATTGT 3' (SEQ ID NO.: 31) and 5' CACAAACTAGAGTCACA-CAC 3' (SEQ ID NO.: 32).

In certain embodiments, the HER-2 positive subject is treated with trastuzumab emtansine, when a mutation in at least one of the amplicons corresponding to PIK3CA, PIK3R1 and PTEN is detected.

In some embodiments, the HER-2 positive status of the subject is assayed by immunohistochemistry (IHC) or fluorescent in situ hybridization (FISH).

In another aspect, the present disclosure provides a method for selecting a subject for treatment with a EGFR tyrosine kinase inhibitor and at least one additional agent comprising: (a) extracting genomic DNA from a formalin fixed paraffin-embedded specimen obtained from the subject; (b) generating a library comprising amplicons corresponding to each of a plurality of cancer-related genes, said plurality of cancer-related genes comprising AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN, wherein (i) generating said library proceeds independently of using a bait set comprising nucleic acid sequences that are complementary to at least one of the plurality of amplicons, and (ii) the quality of the genomic DNA extracted from the formalin fixed paraffin-embedded specimen is not assessed using quantitative PCR prior to generating the library; (c) detecting at least one mutation in at least one of the plurality of amplicons; and (d) selecting the subject for treatment with a EGFR tyrosine kinase inhibitor and at least one additional agent, if a mutation in at least one of the amplicons corresponding to EGFR, and a mutation in at least one of the amplicons corresponding to KRAS, PIK3R1 and BRAF are detected.

In some embodiments of the method, the formalin fixed paraffin-embedded specimen is a heterogeneous tumor. In some embodiments, 5%-10% of the cells of the heterogeneous tumor harbor at least one mutation in at least one of the plurality of amplicons. In other embodiments, at least 10% of the cells of the heterogeneous tumor harbor at least one mutation in at least one of the plurality of amplicons.

In certain embodiments, the EGFR tyrosine kinase inhibitor is gefitinib or erlotinib.

In one aspect, the present disclosure provides a method for predicting the likelihood of responsiveness to treatment with vemurafenib in a subject diagnosed as having melanoma comprising: (a) extracting genomic DNA from a formalin fixed paraffin-embedded specimen obtained from the subject; (b) generating a library comprising amplicons corresponding to each of a plurality of cancer-related genes, said plurality of cancer-related genes comprising AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STKl1, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN, wherein (i) generating said library proceeds independently of using a bait set comprising nucleic acid sequences that are complementary to at least one of the plurality of amplicons, and (ii) the quality of the genomic DNA extracted from the formalin fixed paraffin-embedded specimen is not assessed using quantitative PCR prior to generating the library; (c) detecting at least one mutation in at least one of the plurality of amplicons; and (d) identifying the subject as having at least one of a high likelihood of responsiveness to treatment with vemurafenib when a mutation in at least one of the amplicons corresponding to BRAF is detected, and a low likelihood of responsiveness to treatment with vemurafenib when a mutation in at least one of the amplicons corresponding to NRAS is detected.

In one aspect, the present disclosure provides a method for predicting the likelihood of responsiveness to treatment with anti-EGFR therapy in a subject diagnosed as having colorectal cancer comprising: (a) extracting genomic DNA from a formalin fixed paraffin-embedded specimen obtained from the subject; (b) generating a library comprising amplicons corresponding to each of a plurality of cancer-related genes, said plurality of cancer-related genes comprising AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STKl1, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN, wherein (i) generating said library proceeds independently of using a bait set comprising nucleic acid sequences that are complementary to at least one of the plurality of amplicons, and (ii) the quality of the genomic DNA extracted from the formalin fixed paraffin-embedded specimen is not assessed using quantitative PCR prior to generating the library; (c) detecting at least one mutation in at least one of the plurality of amplicons; and (d) identifying the subject as having a low likelihood of responsiveness to treatment with anti-EGFR therapy when a mutation in at least one of the amplicons corresponding to KRAS, BRAF, NRAS, PIK3CA, and PTEN is detected.

BRIEF DESCRIPTION OF THE DRAWINGS

FIG. 1 shows the clinical characteristics of the 121 patients that provided the tumor samples that were analyzed in the present study.

FIG. 2 shows the results of the inter-assay precision experiments with FFPE specimens harboring variants BRAF G466Y, TP53 R175H, DDR2 L34P, EGFR E865G, EGFR E866V, TP53 R248W, Notch Q2406A, and TP53 A159 M160insRA.

FIG. 3 shows the results of the intra-assay precision experiments with cell lines harboring variants EGFR ΔE746_A750, EGFR L858R, and AKT1 E17K.

FIG. 7 shows the molecular profile of 28 breast cancer tumor samples that were initially screened for ER, PR and HER-2 expression.

DETAILED DESCRIPTION

Figure 4:
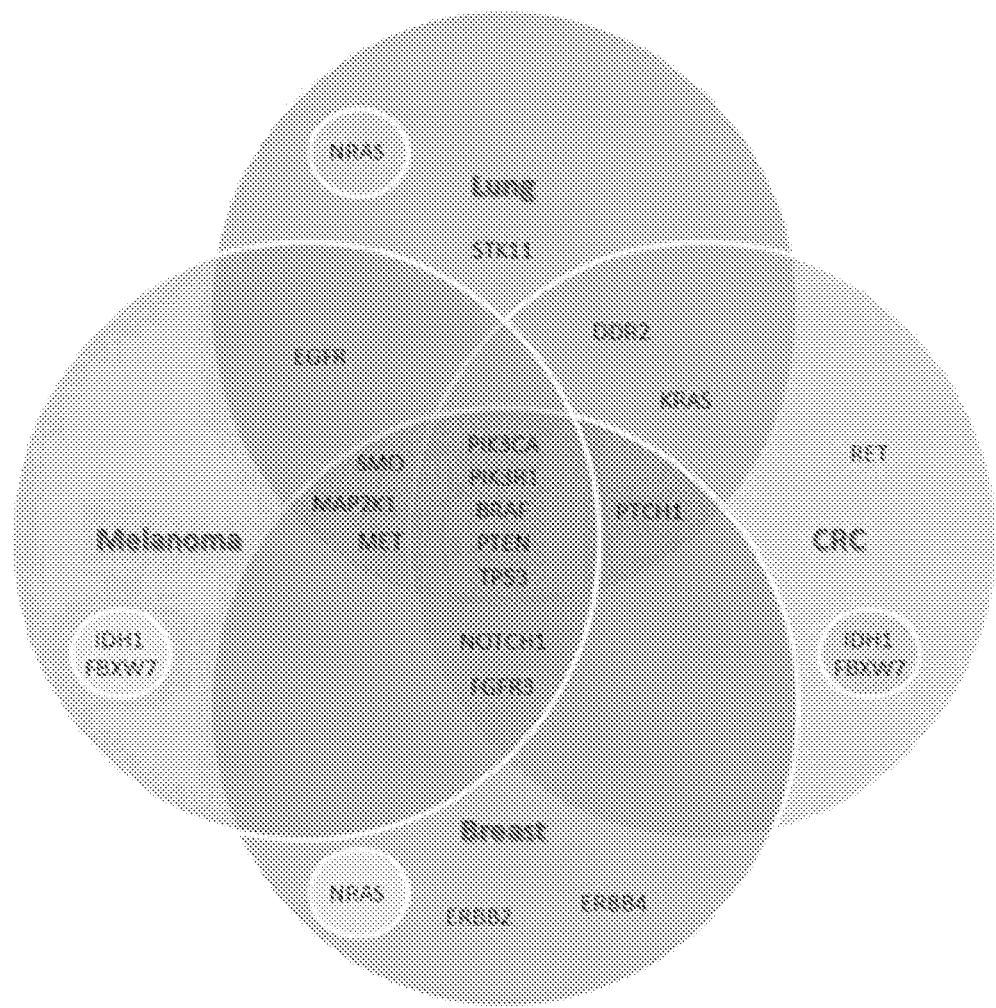
FIG. 4 is a Venn diagram that summarizes the mutated genes detected by the solid tumor screening assay of the present technology according to tumor type: lung cancer, colorectal cancer, melanoma, and breast cancer. Genes that were mutated in several tumor types are depicted in their respective regions of overlap where possible.

The present disclosure provides methods for determining whether a patient diagnosed with breast cancer, colorectal cancer, melanoma or lung cancer will benefit from or is predicted to be responsive to treatment with an individual therapeutic agent or a specific combination of therapeutic agents. These methods are based on screening a patient's solid tumors and detecting alterations in target nucleic acid sequences corresponding to a specific set of cancer-related genes using a highly sensitive Next-Generation Sequencing (NGS) PCR-based assay. Kits for use in practicing the methods are also provided.

Molecular profiling of tumors is becoming increasingly important in the management of advanced cancer. NGS is widely used in cancer research and has become an attractive diagnostic technology in clinical laboratories because of its ability to detect multiple variants in a single assay.

FFPE specimens are integral to the diagnosis of virtually every suspected cancer case, and the estimated millions of archived samples can provide a wealth of molecular information about disease progression and treatment. While FFPE techniques are the standard for protecting tissues for downstream molecular analysis and ease of archiving, storage of tissues in formaldehyde solution results in extensive crosslinking of proteins to other proteins and to nucleic acids and in nucleic acid fragmentation. FFPE techniques can result in the partial denaturation of the DNA and may cause damage to the DNA base pairs themselves, thereby compromising the accuracy of NGS assays. Moreover, the amount of tumor tissue available for biopsy is often limited. These challenges are further exacerbated by the extent of molecular heterogeneity observed in tumor samples, which makes the detection of actionable genetic alterations in FFPE tissues extremely difficult.

Thus, the limited amount of high-quality DNA obtained from FFPE tumor samples disincentivizes the use of large-scale solid tumor screening panels which require large quantities of input DNA (e.g., 50 ng for FoundationOne® panel that interrogates the entire coding sequence of over 300 cancer-related genes and 28 gene rearrangements, Foundation Medicine®). Moreover, analysis of cancer-related genes that are commonly associated with hematologic variants (e.g., ABL1) are less likely to provide guidance on targeted treatment strategies for genetically heterogeneous solid tumors. Accordingly, there is a need for more focused solid tumor screening panels that provide accurate and clinically relevant information on heterogeneous solid tumors but are economical in terms of their use of input DNA from FFPE samples.

One objective of the present technology was to develop a highly sensitive solid tumor profiling panel that can simultaneously detect a broad range of mutations in specifically targeted exons or gene regions of a preselected set of cancer-related genes that are currently, or are likely to become, therapeutically actionable in solid tumors. In some embodiments, the solid tumors manifest in patients diagnosed as having melanoma, lung cancer, colorectal cancer, breast cancer, thyroid cancer, gastrointestinal stromal tumors, etc.

The present disclosure provides methods for detecting actionable genetic mutations in a specific set of cancer-related genes in solid tumors (derived from FFPE tissues) that are missed by traditional Sanger sequencing methods. In one aspect, the methods of the present technology are useful in detecting genetic alterations in a specific set of cancer-related genes in highly heterogeneous tumors samples. Further, the methods disclosed herein are less labor intensive, require less DNA input from FFPE specimens, and provide additional insights into how different signaling pathways are impacted within a particular tumor sample (e.g., a heterogeneous tumor) compared to other existing NGS PCR-based tumor screening assays. In particular, the methods of the present technology screen for mutations in specific target regions within 34 preselected cancer-related genes, which in turn provide a general overview of the molecular profile of a FFPE tumor sample (e.g., a heterogeneous tumor), without prior assessment of the quality of the genomic DNA extracted from the FFPE tumor sample.

The methods disclosed herein are useful in (a) predicting the responsiveness of a subject diagnosed with breast cancer, colorectal cancer, melanoma or lung cancer to a particular therapeutic agent, and (b) selecting optimal treatment strategies for the subject in light of the nature of the individual subject's tumor. Accordingly, DNA degradation/partial DNA denaturation during the FFPE process and tumor heterogeneity do not appear to influence the sensitivity of the solid tumor screening assay of the present technology.

Definitions

As used herein, the term "about" in reference to a number is generally taken to include numbers that fall within a range of 1%-5% in either direction (greater than or less than) of the number unless otherwise stated or otherwise evident from the context.

As used herein, the terms "amplify" or "amplification" with respect to nucleic acid sequences, refer to methods that increase the representation of a population of nucleic acid sequences in a sample. Nucleic acid amplification methods, such as PCR, isothermal methods, rolling circle methods, etc., are well known to the skilled artisan. Copies of a particular nucleic acid sequence generated in vitro in an amplification reaction are called "amplicons" or "amplification products".

As used herein, the term "actionable genetic alterations" refers to mutations that are associated with (1) treatment with an FDA approved drug, (2) a guideline supported drug treatment, (3) a guideline indication of sensitivity or resistance to a particular treatment, (4) ongoing clinical trials, (5) clinical data supporting an indication of resistance or sensitivity to drug treatment, (6) pre-clinical data showing strong evidence of resistance or sensitivity to a targeted treatment, or (6) a prognostic implication that may guide a physician's treatment decisions.

The term "adapter" refers to a short, chemically synthesized, nucleic acid sequence which can be used to ligate to the end of a nucleic acid sequence in order to facilitate attachment to another molecule. The adapter can be single-stranded or double-stranded. An adapter can incorporate a short (typically less than 50 base pairs) sequence useful for PCR amplification or sequencing.

As used herein, an "alteration" of a gene or gene product (e.g., a marker gene or gene product) refers to the presence of a mutation or mutations within the gene or gene product, e.g., a mutation, which affects the quantity or activity of the gene or gene product, as compared to the normal or wild-type gene. The genetic alteration can result in changes in the quantity, structure, and/or activity of the gene or gene product in a cancer tissue or cancer cell, as compared to its quantity, structure, and/or activity, in a normal or healthy tissue or cell (e.g., a control). For example, an alteration which is associated with cancer, or predictive of responsiveness to anti-cancer therapeutics, can have an altered nucleotide sequence (e.g., a mutation), amino acid sequence, chromosomal translocation, intra-chromosomal inversion, copy number, expression level, protein level, protein activity, in a cancer tissue or cancer cell, as compared to a normal, healthy tissue or cell. Exemplary mutations include, but are not limited to, point mutations (e.g., silent, missense, or nonsense), deletions, insertions, inversions, linking mutations, duplications, translocations, inter- and intra-chromosomal rearrangements. Mutations can be present in the coding or non-coding region of the gene. In certain embodiments, the alterations are associated with a phenotype, e.g., a cancerous phenotype (e.g., one or more of cancer risk, cancer progression, cancer treatment or resistance to cancer treatment). In one embodiment, the alteration is associated with one or more of: a genetic risk factor for cancer, a positive treatment response predictor, a negative treatment response predictor, a positive prognostic factor, a negative prognostic factor, or a diagnostic factor.

"Bait", as used herein, is a type of hybrid capture reagent that retrieves target nucleic acid sequences for sequencing. A bait can be a nucleic acid molecule, e.g., a DNA or RNA molecule, which can hybridize to (e.g., be complementary to), and thereby allow capture of a target nucleic acid. In one embodiment, a bait is an RNA molecule (e.g., a naturally-occurring or modified RNA molecule); a DNA molecule (e.g., a naturally-occurring or modified DNA molecule), or a combination thereof. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

As used herein, "bait set" refers to one or a plurality of bait molecules.

The terms "cancer" or "tumor" are used interchangeably and refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell. As used herein, the term "cancer" includes premalignant, as well as malignant cancers.

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be an RNA sequence complementary to the DNA sequence or its complement sequence, and can also be a cDNA.

As used herein, a "control" is an alternative sample used in an experiment for comparison purpose. A control can be "positive" or "negative." A "control nucleic acid sample" or "reference nucleic acid sample" as used herein, refers to nucleic acid molecules from a control or reference sample. In certain embodiments, the reference or control nucleic acid sample is a wild type or a non-mutated DNA or RNA sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

"Detecting" as used herein refers to determining the presence of a mutation or alteration in a nucleic acid of interest in a sample. Detection does not require the method to provide 100% sensitivity.

"Gene" as used herein refers to a DNA sequence that comprises regulatory and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained. Although a sequence of the nucleic acids may be shown in the form of DNA, a person of ordinary skill in the art recognizes that the corresponding RNA sequence will have a similar sequence with the thymine being replaced by uracil, i.e., "T" is replaced with "U."

The term "heterogeneous tumor" as used herein refers to a tumor that comprises subpopulations of cells with distinct molecular variations (e.g., subclones with varying genotypes). In some embodiments, the heterogeneous tumor cells may also exhibit distinct phenotypic profiles including differences in cellular morphology, gene expression, metabolism, motility, proliferation, and metastatic potential. In some embodiments, the degree of heterogeneity within a tumor may depend on the tissue in which the tumor manifests.

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Hybridizations are typically and preferably conducted with probe-length nucleic acid molecules, preferably 15-100 nucleotides in length, more preferably 18-50 nucleotides in length. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point (Tm) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, the terms "individual", "patient", or "subject" are used interchangeably and refer to an individual organism, a vertebrate, a mammal, or a human. In a preferred embodiment, the individual, patient or subject is a human.

As used herein, the term "library" refers to a collection of nucleic acid sequences, e.g., a collection of nucleic acids derived from whole genomic, subgenomic fragments, cDNA, cDNA fragments, RNA, RNA fragments, or a combination thereof. In one embodiment, a portion or all of the library nucleic acid sequences comprises an adapter sequence. The adapter sequence can be located at one or both ends. The adapter sequence can be useful, e.g., for a sequencing method (e.g., an NGS method), for amplification, for reverse transcription, or for cloning into a vector.

The library can comprise a collection of nucleic acid sequences, e.g., a target nucleic acid sequence (e.g., a tumor nucleic acid sequence), a reference nucleic acid sequence, or a combination thereof). In some embodiments, the nucleic acid sequences of the library can be derived from a single subject. In other embodiments, a library can comprise nucleic acid sequences from more than one subject (e.g., 2, 3, 4, 5, 6, 7, 8, 9, 10, 20, 30 or more subjects). In some embodiments, two or more libraries from different subjects can be combined to form a library having nucleic acid sequences from more than one subject. In one embodiment, the subject is human having, or at risk of having, a cancer or tumor.

A "library nucleic acid sequence" refers to a nucleic acid molecule, e.g., a DNA, RNA, or a combination thereof, that is a member of a library. Typically, a library nucleic acid sequence is a DNA molecule, e.g., genomic DNA or cDNA. In some embodiments, a library nucleic acid sequence is fragmented, e.g., sheared or enzymatically prepared, genomic DNA. In certain embodiments, the library nucleic acid sequences comprise sequence from a subject and sequence not derived from the subject, e.g., adapter sequence, a primer sequence, or other sequences that allow for identification, e.g., "barcode" sequences.

The term "multiplex PCR" as used herein refers to amplification of two or more PCR products or amplicons which are each primed using a distinct primer pair.

"Next-generation sequencing or NGS" as used herein, refers to any sequencing method that determines the nucleotide sequence of either individual nucleic acid molecules (e.g., in single molecule sequencing) or clonally expanded proxies for individual nucleic acid molecules in a high throughput parallel fashion (e.g., greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. Nature Biotechnology Reviews 11:31-46 (2010).

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. Oligonucleotides of the method which function as primers or probes are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. The oligonucleotide may be generated in any manner, including, for example, chemical synthesis, DNA replication, restriction endonuclease digestion of plasmids or phage DNA, reverse transcription, PCR, or a combination thereof. The oligonucleotide may be modified e.g., by addition of a methyl group, a biotin or digoxigenin moiety, a fluorescent tag or by using radioactive nucleotides.

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. The term primer as used herein includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of dsDNA. A "reverse primer" anneals to the sense-strand of dsDNA.

As used herein, "primer pair" refers to a forward and reverse primer pair (i.e., a left and right primer pair) that can be used together to amplify a given region of a nucleic acid of interest.

As used herein, a "sample" refers to a substance that is being assayed for the presence of a mutation in a nucleic acid of interest. Processing methods to release or otherwise make available a nucleic acid for detection are well known in the art and may include steps of nucleic acid manipulation. A biological sample may be a body fluid or a tissue sample. In some cases, a biological sample may consist of or comprise blood, plasma, sera, urine, feces, epidermal sample, vaginal sample, skin sample, cheek swab, sperm, amniotic fluid, cultured cells, bone marrow sample, tumor biopsies, aspirate and/or chorionic villi, cultured cells, and the like. Fresh, fixed or frozen tissues may also be used. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. Whole blood samples of about 0.5 to 5 ml collected with EDTA, ACD or heparin as anti-coagulant are suitable.

The term "sensitivity," as used herein in reference to the methods of the present technology, is a measure of the ability of a method to detect a preselected sequence variant in a heterogeneous population of sequences. A method has a sensitivity of S % for variants of F % if, given a sample in which the preselected sequence variant is present as at least F % of the sequences in the sample, the method can detect the preselected sequence at a preselected confidence of C %, S % of the time. By way of example, a method has a sensitivity of 90% for variants of 5% if, given a sample in which the preselected variant sequence is present as at least 5% of the sequences in the sample, the method can detect the preselected sequence at a preselected confidence of 99%, 9 out of 10 times (F=5%; C=99%; S=90%).

The term "specific" as used herein in reference to an oligonucleotide primer means that the nucleotide sequence of the primer has at least 12 bases of sequence identity with a portion of the nucleic acid to be amplified when the oligonucleotide and the nucleic acid are aligned. An oligonucleotide primer that is specific for a nucleic acid is one that, under the stringent hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

As used herein, a "solid tumor" is an abnormal mass of tissue that usually does not contain cysts or liquid areas. Solid tumors may be benign, or malignant (cancer). Examples of solid tumors are sarcomas, carcinomas, and lymphomas. A solid tumor is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient. The tumor does not need to have measurable dimensions.

Specific criteria for the staging of cancer are dependent on the specific cancer type based on tumor size, histological characteristics, tumor markers, and other criteria known by those of skill in the art. Generally, cancer stages can be described as follows:

Stage 0. Carcinoma in situ

Stage I, Stage II, and Stage III. Higher numbers indicate more extensive disease: Larger tumor size and/or spread of the cancer beyond the organ in which it first developed to nearby lymph nodes and/or tissues or organs adjacent to the location of the primary tumor Stage IV. The cancer has spread to distant tissues or organs "Specificity," as used herein, is a measure of the ability of a method to distinguish a truly occurring preselected sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or members of a gene family. A method has a specificity of X % if, when applied to a sample set of $N_{Total}$ sequences, in which $X_{True}$ sequences are truly variant and $X_{Not\ true}$ are not truly variant, the method selects at least X % of the not truly variant as not variant. E.g., a method has a specificity of 90% if, when applied to a sample set of 1,000 sequences, in which 500 sequences are truly variant and 500 are not truly variant, the method selects 90% of the 500 not truly variant sequences as not variant. Exemplary specificities include 90, 95, 98, and 99%.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

As used herein, the terms "target sequence" and "target nucleic acid sequence" refer to a specific nucleic acid sequence to be detected and/or quantified in the sample to be analyzed.

As used herein, the terms "treat," "treating" or "treatment" refer, to an action to obtain a beneficial or desired clinical result including, but not limited to, alleviation or amelioration of one or more signs or symptoms of a disease or condition (e.g., regression, partial or complete), diminishing the extent of disease, stability (i.e., not worsening, achieving stable disease) state of disease, amelioration or palliation of the disease state, diminishing rate of or time to progression, and remission (whether partial or total).

Impact of Tumor Profiling on Targeted Drug Therapies

Cancer has become the focus for drug development over the past decade, with the number of new cancer drugs in development tripling from 2001 to 2010. Siegel et al., *CA Cancer J Clin.* 64:9-29 (2014). The modest survival rates and high degree of adverse effects from standard chemotherapy and radiation treatment have led to focus new drug developments on treatments that target specific signaling molecules or whole regulatory pathways. The efficacy of many targeted drugs can be influenced by molecular biomarkers, which are now commonly used as an aid in selecting patients for treatment.

Furthermore, mutational heterogeneity of solid tumors has broadened the scope of cell signaling pathways that are targeted by new therapeutics. Hanahan & Weinberg, *Cell* 144:646-74 (2011); Fisher et al., *British J. Cancer* 108:479-485 (2013); Burrella & Swantona, *Molecular Oncology* 8:1095-1111 (2014). Identifying pathway alterations could steer a clinician towards or away from drugs targeting the affected pathways. Furthermore, without wishing to be bound by theory, an overlap in affected regulatory pathways among cancers may indicate that approved biomarkers and drug treatments for one tumor type may have potential clinical applications in other tumor types. One example of successfully applying a single targeted treatment across multiple tumor types and biomarker indications is the use of the tyrosine kinase inhibitor imatinib (imatinib mesylate). Imatinib was originally developed to target c-abl in chronic myeloid leukemias (CMLs) harboring the Philadelphia chromosome (BCR/ABL1), but its indications have since been expanded to include the treatment of certain GIST tumors harboring KIT or PDGFRA mutations as well as advanced or metastatic melanomas harboring KIT mutations. Peng et al., Clinical Pharmacokinetics 44:879-894 (2005); Guo et al., *JCO* 29:2904-2909 (2011). Accordingly, there might be a potential benefit to prospectively profiling tumors for targets that might not, at the moment, be clinically actionable for a given tumor type.

Mutations in "downstream" signaling proteins can also cause drug resistance, lending additional utility to mutation profiling. Kelloff & Sigman, *Nat Rev Drug Discov.* 11:201-214 (2012). Profiling tumors that exhibit acquired resistance has led to the identification of mechanisms of resistance. For example, a melanoma patient with acquired resistance to the BRAF inhibitor vemurafenib was found to harbor a point mutation in MEK1 C121S. Wagle et al., Cancer Discovery 4:61-68 (2014); Narita et al., *Mol Cancer Ther.* 13:823-832 (2014). MEK1 encodes a kinase downstream of BRAF, and the C121S mutation was believed to account for vemurafenib resistance in the aforementioned case. Although no alternative drug was available at the time, a novel MEK1 inhibitor in preclinical development was recently reported to be active against vemurafenib-resistant melanoma harboring the MEK1 C121S mutation. Wagle et al., *J Clin Oncol.* 29:3085-3096 (2011). Cases such as this highlight the potential utility of identifying mutations in a broad range of cancer-associated genes in patients exhibiting acquired resistance, even those not yet linked to the therapeutic response.

Treatment-naïve patients also frequently have concurrent mutations in multiple genes that may have implications for prognosis or treatment decisions. For example, concurrent KRAS and PIK3CA mutations are commonly found in colorectal and lung cancers, and the combinatorial status may have prognostic or treatment predictive value. Roock et al., *Lancet Oncology* 12:594-603 (2011); Chaft et al., *Mol Cancer Ther.* 11; 485 (2012); Jänne P A et al., *Lancet Oncol.* 14:38-47 (2013). Concurrent PIK3CA mutations in EGFR-positive lung cancers were described to be associated with resistance to EGFR tyrosine kinase inhibitors (TKIs). Ludovini et al., *J. Thoracic Oncology* 6:707-715 (2011). Moreover, a recent study demonstrated that 20% of ALK rearrangement-positive lung cancers harbored co-occurring mutations in EGFR or MET, which may be an important factor in the decision to treat with crizotinib. Boland et al., *J. Thoracic Oncology* 8:574-581 (2013). Thus, prospectively profiling tumors would aid in the selection of optimal therapeutic regimens, thereby improving the likelihood of a positive patient outcome.

NGS Platforms

In some embodiments, high throughput, massively parallel sequencing employs sequencing-by-synthesis with reversible dye terminators. In other embodiments, sequencing is performed via sequencing-by-ligation. In yet other embodiments, sequencing is single molecule sequencing. Examples of Next Generation Sequencing techniques include, but are not limited to pyrosequencing, Reversible dye-terminator sequencing, SOLiD sequencing, Ion semiconductor sequencing, Helioscope single molecule sequencing etc.

The Ion Torrent™ (Life Technologies, Carlsbad, Calif.) amplicon sequencing system employs a flow-based approach that detects pH changes caused by the release of hydrogen ions during incorporation of unmodified nucleotides in DNA replication. For use with this system, a sequencing library is initially produced by generating DNA fragments flanked by sequencing adapters. In some embodiments, these fragments can be clonally amplified on particles by emulsion PCR. The particles with the amplified template are then placed in a silicon semiconductor sequencing chip. During replication, the chip is flooded with one nucleotide after another, and if a nucleotide complements the DNA molecule in a particular microwell of the chip, then it will be incorporated. A proton is naturally released when a nucleotide is incorporated by the polymerase in the DNA molecule, resulting in a detectable local change of pH. The pH of the solution then changes in that well and is detected by the ion sensor. If homopolymer repeats are present in the template sequence, multiple nucleotides will be incorporated in a single cycle. This leads to a corresponding number of released hydrogens and a proportionally higher electronic signal.

The 454TM GS FLX™ sequencing system (Roche, Germany), employs a light-based detection methodology in a large-scale parallel pyrosequencing system. Pyrosequencing uses DNA polymerization, adding one nucleotide species at a time and detecting and quantifying the number of nucleotides added to a given location through the light emitted by the release of attached pyrophosphates. For use with the 454™ system, adapter-ligated DNA fragments are fixed to small DNA-capture beads in a water-in-oil emulsion and amplified by PCR (emulsion PCR). Each DNA-bound bead is placed into a well on a picotiter plate and sequencing reagents are delivered across the wells of the plate. The four DNA nucleotides are added sequentially in a fixed order across the picotiter plate device during a sequencing run. During the nucleotide flow, millions of copies of DNA bound to each of the beads are sequenced in parallel. When a nucleotide complementary to the template strand is added to a well, the nucleotide is incorporated onto the existing DNA strand, generating a light signal that is recorded by a CCD camera in the instrument.

Sequencing technology based on reversible dye-terminators: DNA molecules are first attached to primers on a slide and amplified so that local clonal colonies are formed. Four types of reversible terminator bases (RT-bases) are added, and non-incorporated nucleotides are washed away. Unlike pyrosequencing, the DNA can only be extended one nucleotide at a time. A camera takes images of the fluorescently labeled nucleotides, then the dye along with the terminal 3' blocker is chemically removed from the DNA, allowing the next cycle.

Helicos's single-molecule sequencing uses DNA fragments with added polyA tail adapters, which are attached to the flow cell surface. At each cycle, DNA polymerase and a single species of fluorescently labeled nucleotide are added, resulting in template-dependent extension of the surface-immobilized primer-template duplexes. The reads are performed by the Helioscope sequencer. After acquisition of images tiling the full array, chemical cleavage and release of the fluorescent label permits the subsequent cycle of extension and imaging.

Sequencing by synthesis (SBS), like the "old style" dye-termination electrophoretic sequencing, relies on incorporation of nucleotides by a DNA polymerase to determine the base sequence. A DNA library with affixed adapters is denatured into single strands and grafted to a flow cell, followed by bridge amplification to form a high-density array of spots onto a glass chip. Reversible terminator methods use reversible versions of dye-terminators, adding one nucleotide at a time, detecting fluorescence at each position by repeated removal of the blocking group to allow polymerization of another nucleotide. The signal of nucleotide incorporation can vary with fluorescently labeled nucleotides, phosphate-driven light reactions and hydrogen ion sensing having all been used. Examples of SBS platforms include Illumina GA and HiSeq 2000. The MiSeq® personal sequencing system (Illumina, Inc.) also employs sequencing by synthesis with reversible terminator chemistry.

In contrast to the sequencing by synthesis method, the sequencing by ligation method uses a DNA ligase to determine the target sequence. This sequencing method relies on enzymatic ligation of oligonucleotides that are adjacent through local complementarity on a template DNA strand. This technology employs a partition of all possible oligonucleotides of a fixed length, labeled according to the sequenced position. Oligonucleotides are annealed and ligated and the preferential ligation by DNA ligase for matching sequences results in a dinucleotide encoded color space signal at that position (through the release of a fluorescently labeled probe that corresponds to a known nucleotide at a known position along the oligo). This method is primarily used by Life Technologies' SOLiD™ sequencers. Before sequencing, the DNA is amplified by emulsion PCR. The resulting beads, each containing only copies of the same DNA molecule, are deposited on a solid planar substrate.

SMRT™ sequencing is based on the sequencing by synthesis approach. The DNA is synthesized in zero-mode wave-guides (ZMWs)-small well-like containers with the capturing tools located at the bottom of the well. The sequencing is performed with use of unmodified polymerase (attached to the ZMW bottom) and fluorescently labeled nucleotides flowing freely in the solution. The wells are constructed in a way that only the fluorescence occurring at the bottom of the well is detected. The fluorescent label is detached from the nucleotide at its incorporation into the DNA strand, leaving an unmodified DNA strand.

Solid Tumor Screening Methods of the Present Technology

Disclosed herein are methods and assays that are based, at least in part, on a preselected set of genes that are associated with a cancerous phenotype (e.g., one or more of cancer risk, cancer progression, cancer treatment response or resistance to cancer treatment). Such preselected genes enable the application of sequencing methods, particularly methods that rely on massively parallel sequencing of a large number of diverse genes, e.g., from tumor or control samples.

In one embodiment, the methods featured in the present technology are used in a multiplex, multi-gene assay format, e.g., assays that incorporate multiple signals from a large number of diverse genetic alterations in a large number of genes.

The methods of the present technology are based on the principle that assaying cell populations within a tumor sample, e.g., a heterogeneous solid tumor, for the presence of one or more alterations in a preselected set of cancer-related genes is useful in determining whether a patient will benefit from or will respond to treatment with an individual therapeutic agent or a specific combination of therapeutic agents. In some embodiments of the method, the preselected set of cancer-related genes corresponds to AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN. In some embodiments of the method, the presence of one or more alterations in the preselected set of cancer-related genes is detected by assaying a plurality of amplicons corresponding to the preselected set of cancer-related genes.

The advantages of the methods of the present technology over other comparable PCR-based NGS screening panels for solid tumors are two-fold. First, no preliminary assessment of the quality of the genomic DNA extracted from FFPE tissues is required in order to generate highly uniform amplicon-based libraries. Second, the minimal DNA input required for the screening assays disclosed herein is about three times lower than other comparable solid tumor screening panels. For example, the minimal input DNA for the methods disclosed herein is 10 ng for generating 231 amplicons corresponding to 34 genes, whereas the TruSight™

Tumor protocol requires at least 30 ng for generating 174 amplicons corresponding to 26 genes.

The present disclosure provides methods for detecting at least one mutation in a plurality of cancer-related genes in a subject comprising (a) extracting genomic DNA from a FFPE tumor sample obtained from the subject; (b) generating a library comprising amplicons corresponding to each of the plurality of cancer-related genes, said plurality of cancer-related genes comprising AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN, wherein (i) generating said library occurs without the use of a bait set comprising nucleic acid sequences that are complementary to at least one of the plurality of amplicons; and (ii) the quality of the genomic DNA extracted from the FFPE tumor sample is not assessed using quantitative PCR prior to generating the library; (c) ligating an adapter sequence to the ends of the plurality of amplicons; and (d) detecting at least one mutation in at least one of the plurality of amplicons using high throughput massive parallel sequencing.

In some embodiments of the method, the subject has been diagnosed as having, is suspected of having, or is at risk of having breast cancer, melanoma, colorectal cancer or lung cancer.

In some embodiments of the method, the at least one mutation detected is a mutation in EGFR, KRAS, BRAF, NRAS, ERBB2 or PIK3CA. In one embodiment, the at least one mutation detected is selected from the group consisting of BRAF V600E, BRAF V600K, BRAF K483Q, BRAF G466V, BRAF G464V, BRAF E501V, BRAF E501K, EGFR ΔE746_A750, EGFR R680Q, EGFR G598E, KRAS A146T, KRAS R68M, KRAS L19F, KRAS G12V, KRAS G12D, KRAS G12C, KRAS G13D, KRAS G13C, KRAS G12A, KRAS G12S, KRAS Q22K, NRAS Q61K, NRAS Q61R, NRAS G12R, NRAS G12D, PIK3CA C420R, PIK3CA G106R, PIK3CA R38H, PIK3CA E453K, PIK3CA H1044R, PIK3CA N1044K, PIK3CA E545K, PIK3CA Q546H, PIK3CA H1047R, PIK3CA H1043L, PIK3CA M1043V, PIK3CA E542K, PIK3CA E542Q, PIK3CA T1053A, PIK3CA I121V, PIK3CA H1047L, ERBB2 L755S, ERBB2 S310Y, ERBB2 D769Y, ERBB2 S255R, DDR2 H92Y, DDR2 R31L, DDR2 L34P, DDR2 P381R and DDR2 K392N.

In some embodiments of the method, the library comprising amplicons corresponding to each of the plurality of cancer-related genes disclosed herein is generated using no more than 10 ng of extracted genomic DNA from the FFPE tumor sample. In some embodiments of the method, the library comprising amplicons corresponding to each of the plurality of cancer-related genes disclosed herein is generated using 11-25 ng of extracted genomic DNA from the FFPE tumor sample. In some embodiments of the method, the library comprising amplicons corresponding to each of the plurality of cancer-related genes disclosed herein is generated using at least 25 ng of extracted genomic DNA from the FFPE tumor sample.

In some embodiments of the method, the plurality of amplicons are generated by at least two, at least three, at least four, at least five, at least ten, at least twenty, at least thirty, at least forty, at least fifty, or at least one hundred or more pairs of primers disclosed in Table 1. Table 1: Primer Pair Mix Pool 1 Forward Primer Sequence SEQ ID Reverse Primer Sequence SEQ ID

TABLE 1

| Primer Pair Mix Pool 1 | | | |
|---|---|---|---|
| Forward Primer Sequence | SEQ ID NO: | Reverse Primer Sequence | SEQ ID NO: |
| CTGAGGTGGAAGAGACAG | 83 | GCATTTCCTTTCTTCCCAG | 179 |
| ACTGGTTCTCACTCACC | 84 | TTGGTTACATCCCTCTCTG | 180 |
| GCCAGCAAAGCAGTAG | 85 | TGTTGCAGCTGACCAC | 181 |
| TGGAAAAATAGCCTCAATTCT | 86 | TGTTTTCCTTTACTTACTACACC | 182 |
| CACCACATTACATACTTACCAT | 87 | TTTGGCTTGACTTGACTTTT | 183 |
| CTCTGGAAAAGAGTAATTCACA | 88 | TGAAATGACACTTGGAGTAAC | 184 |
| CGTATTTATAGCTGATTTGATGG | 89 | GTATCCACATCCTCTTCCT | 185 |
| GGACTTCACCTGACAGAT | 90 | TGGTCAGTACAAGCACATAC | 186 |
| CTTTGGTTTCTCTTGGTCTAG | 91 | ATGGGCTTTCTTGATGTAAC | 187 |
| GAGTTTCTGCAGATTGACTT | 92 | GGTTCCGCCAAGAGAT | 188 |
| GTGTTTCCTTTGCAGATG | 93 | GGCCAATTTCCCATTCTAATA | 189 |
| TCACATGCCTCTTTCTCTA | 94 | TGACAAACCGAGCACT | 190 |
| CCTGGCTCTGACTCAC | 95 | CTTCATCCCCCAGTAAGTC | 191 |
| TTTCCCTGCCAAGTGAT | 96 | TTCTGGGAGTTTTCGTATCA | 192 |
| TGCAGCGGTGTTGT | 97 | TCCACAGCCACATCTTT | 193 |
| TCTCGGCTCAAGGAC | 98 | CTGACAGTGCGTACATC | 194 |
| TTCCTCAGTTACACCAATCT | 99 | TCATTCCAAAGTCAGCTATCT | 195 |

TABLE 1-continued

Primer Pair Mix Pool 1

| Forward Primer Sequence | SEQ ID NO: | Reverse Primer Sequence | SEQ ID NO: |
|---|---|---|---|
| GCCTTTGGGGTTACTTT | 100 | AGGTCCACATCCATTCATC | 196 |
| GCTGCTGGAGAAGAGATA | 101 | CATAGGCATGGGTGAGT | 197 |
| AGGTGGCTGGTTATGTC | 102 | CCTTCAGTCCGGTTTTATTTG | 198 |
| GGAGATAAGTGATGGAGATGT | 103 | CAGAAAGCGGTGACTTACT | 199 |
| GGATCGGCCTCTTCAT | 104 | GCTAATGGCCCGTTCTC | 200 |
| CCCAACCAAGCTCTCTT | 105 | CCCACCAGACCATGAGA | 201 |
| ACTGACGTGCCTCTC | 106 | AGCCAATATTGTCTTTGTGT | 202 |
| GCAGGGTCTTCTCTGTT | 107 | CTCCTTCTGCATGGTATTCT | 203 |
| CCAACAGAGGGAAACTAATAG | 108 | CATTAGCATCAGGATTATGACT | 204 |
| CTGATGGGGAGAATGTGA | 109 | CCAGAGCCCAGACCTG | 205 |
| CATTTGACCATGACCATGTA | 110 | GGAGTTACTATATGGGAACTGAT | 206 |
| CCCATGAATACCAGTGACTA | 111 | AACTCTGAGTCTTGTTTCTACA | 207 |
| CTGTTACTTACGTGGACATT | 112 | CCTGCATGAATTTCAATGAC | 208 |
| CTCATTCATCGCCACATAG | 113 | GTTATGCAGACACCATTCAT | 209 |
| GACTTACCTTGCAATGTTTG | 114 | AATTGCATTCACACGTTAAC | 210 |
| ACTGGCCTGTCTCAATAT | 115 | CCTTGACTAAATCTACCATGTTT | 211 |
| AGTGGAAGTATGCCCATATA | 116 | CCAGTGTCTGAGAACATTAGT | 212 |
| TACAGAAGAGGAGTGTCATAT | 117 | AGACAGCACAGAATTGATAC | 213 |
| TGCCCACTGTGTTACT | 118 | TCAGTGTATTCATCGAGATTTAG | 214 |
| AGTTGTGGGTACCTTTAGATT | 119 | TGTCTGCAAGGTTTACAGT | 215 |
| GGCGGTGGTGGT | 120 | GCTGTGCGTCACTGTA | 216 |
| GCCAGGCCTCAACG | 121 | CGCAGGCGGCAGA | 217 |
| GTGACCGAGGACAAC | 122 | GGAAGGCGGTGTTG | 218 |
| CTGACCGACGTTGAC | 123 | GCCTGCTGTGGCCC | 219 |
| CCTGGGATTGCAGATTG | 124 | AGGGCGACGAGAAAC | 220 |
| GTTTCATGGACTCAGTTACT | 125 | TCCTCTAGCTATCTTAATGACT | 221 |
| CCAGACCTTTGCTTTAGATT | 126 | GCTTACTGGAAGTTGACTTT | 222 |
| AAAGACTTGGTGTTGTTGAT | 127 | GGAAGCAGGTGGTCATT | 223 |
| GCCCATCATATTTCTTCAGA | 128 | TGGCTTCTCCTCTACAGA | 224 |
| CGTGCCACCCAGAATAT | 129 | GGATGCTGCAGAAGCTATAA | 225 |
| GGCCTACCTGGTCG | 130 | GTTCAAGCTGAAGAAGATGT | 226 |
| TTCCAGCACTCTGACATAT | 131 | GCTCAGTTCCTGGACAAA | 227 |
| TGCTTTTAGGGCCCAC | 132 | CCTTTGAATGCAGAAGATTCTT | 228 |
| CCAACCTAATAGTGTATTCACA | 133 | AGCAGAGAATGGGTACTC | 229 |
| ATTATTGACTCTGTTGTGCT | 134 | GTTGTCTTTGGCAAGGAT | 230 |
| CCCCAGTCCTCATGTAC | 135 | GCACTGTAATAATCCAGACTG | 231 |
| GCTGGAGGAGCTAGAG | 136 | GTGGGAGACCTTGAACA | 232 |
| CCTTCTCTTCCCCAATCTAC | 137 | GCCATGGAGTCGATGAG | 233 |

TABLE 1-continued

Primer Pair Mix Pool 1

| Forward Primer Sequence | SEQ ID NO: | Reverse Primer Sequence | SEQ ID NO: |
|---|---|---|---|
| AGGAGCCAGGCATTTT | 138 | GCCTGACAAATCCAGAGTA | 234 |
| CTTTCCCCACAATCATACTG | 139 | TGATGAACCGGTCCTTTAC | 235 |
| GCTGGTGTTGTCTCAATAT | 140 | CGACGACAATCTTAAACTGTA | 236 |
| TACGATGCAAGAGTACACA | 141 | ACAACCCACTGAGGTATATG | 237 |
| CCACCACTGGATTTCTCA | 142 | TGTATGGTAGGACCACCAG | 238 |
| CTTATTGGCTTTGGTCTTCA | 143 | AAACAGATTCCTCCTTGTCA | 239 |
| TCAGCATCATTGTAAATTATTCTATT T | 144 | GCACCTGTTTTGTTGTGTA | 240 |
| ACGAGCTGGACCACT | 145 | CCCACCCGTGACCG | 241 |
| TCGGCTCTCCACTCA | 146 | CAGGTGCAGCCACAAA | 242 |
| GGGCCACACTTACTCT | 147 | TCTACCTGGAGATTGACAAC | 243 |
| CCGGGTCTCACTCA | 148 | CAAGCACCCCATCAAG | 244 |
| CGTAGTAGGGGAAGATCATC | 149 | CCGGCACGCTGGT | 245 |
| GGACACTCGCAGTAGAA | 150 | CCACGGTGGCTACAA | 246 |
| ATAATGCTCCTAGTACCTGTAG | 151 | ACCTGTTTGTTGGACATACT | 247 |
| CTTGCACAAATGCTGAAAG | 152 | AAGACTCGGATGATGTACC | 248 |
| CATTTATAGAAACCGAGGTATGA | 153 | GGTTACCCCATGGAACTTA | 249 |
| GTCTGCAGGACAATTCAT | 154 | CAGGAAGCTATCCCTATTCT | 250 |
| CCTAGTAGAATGTTACTACCAA | 1 | CTGCTTCTTGAGTAACACTT | 2 |
| CATGTTCATGCTGTGTATGT | 3 | GCTTCTTTACAAACGTTCAGAA | 4 |
| TCTATGTTCGAACAGGTATCT | 5 | ACTGCTAAACACTAATATAACCTTTG | 6 |
| TTGAAATGTGTTTTATAATTTAGACTAGT | 7 | CCATGAGGTACTGGCC | 8 |
| TTGGTGTTACTGGATCAAATC | 9 | TGCTGAACCAGTCAAACT | 10 |
| TATTATTTTATTTTACAGAGTAACAGACTAG | 11 | TTTAGCACTTACCTGTGACT | 12 |
| TGGAATGCCAGAACTACA | 13 | GTGGAAGATCCAATCCATTTT | 14 |
| GGAATGAATGGCTGAATTATG | 15 | GCGGTATAATCAGGAGTTTT | 16 |
| AGTTGGCCTGAATCACTATA | 17 | GATGTTACTATTGTGACGATCTC | 18 |
| GTGGTCACTAAACCTTAAGA | 45 | GGCTTACCTTAGTGTAAGAG | 46 |
| TTTCATCGAGATGGGAAATATG | 47 | ACCTGTTGGTATTTGGATACT | 48 |
| AGAAGATAATATTGAAGCTGTAGG | 49 | AGAACTCTTATTTTTAATCTGATTTTCA | 50 |
| GGACAGCTATTGAAGCATTTA | 51 | CACAAGAACAAGGGAAACAC | 52 |
| GCAGGCAGCTGAGTATC | 53 | TCATCCTGAATTGTAGCAATCA | 54 |
| TCCACAAAGCCCCTTATAAT | 155 | GTTACCCCAACGGCTAC | 251 |
| CTTGTTTCAGGCATGTAGT | 156 | TGCAGATGGCATCATTAATC | 252 |
| CCCACGCCGTCTTA | 157 | CACCCAGAAAGCAGACTA | 253 |
| AGCGGTGGTGTAGTAC | 158 | CGACACACACGACAATAC | 254 |
| AAGTGCCTTAGCAGAGA | 159 | GTCACAGCCTTCTTCATG | 255 |
| AGACATCAGAAAGCATGATC | 160 | CGCATGGCCTCTTC | 256 |
| TTTGATTGCTGCATATTTCAG | 71 | TCAAAGCATTCTTACCTTACTAC | 72 |

TABLE 1-continued

Primer Pair Mix Pool 1

| Forward Primer Sequence | SEQ ID NO: | Reverse Primer Sequence | SEQ ID NO: |
| --- | --- | --- | --- |
| TTTTAAACTTTTCTTTTAGTTGTGC | 73 | ACTCGATAATCTGGATGACT | 74 |
| CAATTTAGTGAAATAACTATAATGGAAC | 75 | AGTGCCACTGGTCTATAAT | 76 |
| CCTGTGAAATAATACTGGTATGT | 77 | CTACTTTGATATCACCACACAC | 78 |
| TAGAGCGTGCAGATAATGA | 79 | TCAACAACCCCCACAAA | 80 |
| CTTTCTCTAGGTGAAGCTGTA | 81 | GGTTCATTCTCTGGATCAGA | 82 |
| CCATGAGGCAGAGCATA | 161 | GCACCGAGACGATGAA | 257 |
| GGCCATGGCCTGAC | 162 | GCACCTGGCTCCTCT | 258 |
| TATGGTCATGGAAGGGG | 163 | CCCCATACAATTTGATGACA | 259 |
| CCGCTGAGCCACT | 164 | TCCGCCGCACTTAC | 260 |
| GCGTCATCATCTTTGTCAT | 165 | GTGAGCAGGTGGAAGTAG | 261 |
| CATCCCTGACTGTGAGAT | 166 | CCAGATGAGCAGCGT | 262 |
| GGTGGCATGGACAGA | 167 | TCTTCCTCCTCTTCTTCTTC | 263 |
| GTGGGCTACAAGAACTAC | 168 | CAGCAAGTGCCCAGTA | 264 |
| GGGTATGGACACGTTCAT | 169 | CCGAGTCCAGCACCTC | 265 |
| CCTCGAAATGAAGCTACAAC | 170 | AGGCTCCCACCTTTCA | 266 |
| AAGTGGAGAATGTCAGTCT | 171 | ACAGACCCTCTCACTCAT | 267 |
| GAAACTTTCCACTTGATAAGAG | 172 | CCAAGGGTGCAGTTATG | 268 |
| TTACCTCGCTTAGTGCT | 173 | TGCCTCTTGCTTCTCTT | 269 |
| CCCAGAGACCCCAGT | 174 | CCTCACTGATTGCTCTTAGG | 270 |
| AGCCCTGTCGTCTCT | 175 | GCAGCTGTGGGTTGAT | 271 |
| GCCAGGCATTGAAGTC | 176 | GGCCCCTGTCATCTTC | 272 |
| GAGCTGCTGGTGCA | 177 | GTCCTCTGACTGCTCTTT | 273 |
| TCCAATGGATCCACTCAC | 178 | GCTGGATCCCCACTTTT | 274 |

In some embodiments of the method, the plurality of amplicons are generated by at least two, at least three, at least four, at least five, at least ten, at least twenty, at least thirty, at least forty, at least fifty, or at least one hundred or more pairs of primers disclosed in Table 2.

TABLE 2

Primer Pair Mix Pool 2

| Forward Primer Sequence | SEQ ID NO: | Reverse Primer Sequence | SEQ ID NO: |
| --- | --- | --- | --- |
| TCACGTTGGTCCACATC | 275 | GGTCTGACGGGTAGAGT | 370 |
| ACAGGATGACAGGAAGAG | 276 | TCTGTCTCCCCACAGAG | 371 |
| ACGATTTCCCTTGGAGATAT | 277 | TGAAGTGTGCTCTGAACA | 372 |
| AGACAACTGTTCAAACTGAT | 278 | ATGCTTGCTCTGATAGGA | 373 |
| GACCCCAAGCTTTAGTAAAT | 279 | ACACAAGACTCAGAATAGATACA | 374 |
| ACACCCTCCATTTTATCAC | 280 | ATGTCTCTTCTTCCTACCTG | 375 |
| CACGAATGTGTGGTTAACTC | 281 | GCCACACGTGGTATTCA | 376 |
| TTTCCTTCCCCCTTGTC | 282 | TGAGCTCCCTACCTGATT | 377 |

TABLE 2-continued

Primer Pair Mix Pool 2

| Forward Primer Sequence | SEQ ID NO: | Reverse Primer Sequence | SEQ ID NO: |
|---|---|---|---|
| TTGTATTCTCTGCCTTCTCT | 283 | CACCTTCTCCAGCATTTTC | 378 |
| AATAACCGCTCCTCATCA | 284 | CATCATCCTCACCTGACTC | 379 |
| CTGAGACTAGATGACTTTGTC | 285 | TTCAAAATGTAGACCACAGAC | 380 |
| CTTTACTTAAATAGGGCAAGTTC | 286 | CGGAAGAACTCTCCAGTATTC | 381 |
| TTCCTTTATTTTTGTTCCCAAAG | 287 | CCTTGTTGAAGGAGCAGAA | 382 |
| CAACGCCACAACCAC | 288 | CCAGAGCCCGACTCG | 383 |
| GTACCAGATGGATGTGAAC | 289 | TCTCCAAGATGGGATACTC | 384 |
| AGAGACATGCATGAACATTT | 290 | GGCGTCTGCGTACTTC | 385 |
| CTTGTCTCTGTGTTCTTGT | 291 | CAGGGACCTTACCTTATACA | 386 |
| AGTTAACGTCTTCCTTCTCT | 292 | CCCCCACACAGCAAA | 387 |
| GCATCTGCCTCACCT | 293 | GTATCTCCCTTCCCTGATTAC | 388 |
| AGCCAGGAACGTACTG | 294 | TGGTCCCTGGTGTCA | 389 |
| AAGGGATTGTGATTGTTCAT | 295 | AGGCGTTCTCCTTTCTC | 390 |
| CCTGATCTCCTTAGACAACT | 296 | GCAGTGAGTGGGTACCTC | 391 |
| ATACCCTCTCAGCGTAC | 297 | CCGGACATGGTCTAAGAG | 392 |
| GGGGATGAGCTACCTG | 298 | CCATCTGCATGGTACTCT | 393 |
| TTGGCCAGCAAGAATG | 299 | GTGCTCTCATTTTAAAGATGG | 394 |
| CAGTGCAAGGTTTACACA | 300 | GCTTGTTTGCTGAATGTTAAC | 395 |
| GAAAGGAGAGCAGGATAATAA | 301 | GTGTGCAGAACAATGTGA | 396 |
| CACTGATATTTAAATGCCTTAGAG | 302 | GGACTTCAAGAACTTGGATTA | 397 |
| CAGCAGCTTGGTTTCTTC | 303 | ACTATGGGACTTGAAAACGG | 398 |
| TGCAACGTGTGTAGACA | 304 | ACAGGCCAGTGTTTACAT | 399 |
| TCCCAACCATGACAAGA | 305 | AACATCATCATTAGTGGATCTAC | 400 |
| GCTACTTGCAATGATATACAC | 306 | TGTGATCACATGCTTACAGT | 401 |
| CACCCAATGAAGAATGTAATTG | 307 | GAGAAATTGCTTGCTTTAGATG | 402 |
| AGCCCAGCCATTTCTAA | 308 | GTGTCAGAGATGGAGATGAT | 403 |
| CTGGCTGCTGAAGTCT | 309 | AGCGCCTGGAAGAGA | 404 |
| CACTGTGGAGGCATTTG | 310 | GGCATGAGGTCACTGAC | 405 |
| CAGTGGCTCAAGCAC | 311 | GCTCCAACCCCTAGAC | 406 |
| GAGGAGCCCGTGTC | 312 | ACACCAGGTCCTTGAAG | 407 |
| CTGCAGCTGGTCCTT | 313 | GGGATGCCACTCACAG | 408 |
| GCAGGAGCTGACAGTA | 314 | GGAAGCTGGCAATCTCTA | 409 |
| CGGTAGTTGCCCTTCTC | 315 | CCCGTTCTACGAGAAGAATAA | 410 |
| CGCTGTGTCCTTTCAG | 316 | GCCCACCTCGTTGT | 411 |
| GACATTTTCAAAGCAGTGTATC | 317 | CCCTAAGTTTGTAAGTAGTGC | 412 |
| CCAGTCCCTCTGGAATAA | 318 | AGAAGCAAAGCGTTCTTTAC | 413 |
| CTCTATAGTGGGGTCGTAT | 319 | AGACCCTGTAGGAGGAC | 414 |
| ACATTATTGCCAACATGACT | 320 | TGGCACCATACGAAATATTC | 415 |

TABLE 2-continued

Primer Pair Mix Pool 2

| Forward Primer Sequence | SEQ ID NO: | Reverse Primer Sequence | SEQ ID NO: |
|---|---|---|---|
| CATACTCAACACGATTCTGT | 321 | CCGGATCAGTGCATAACA | 416 |
| GGCACGGTTGAATGTAA | 322 | ATCATGACTGATATGGTAGACA | 417 |
| CCACATTTCTCTTCCATTGTA | 323 | TCTGGAGAGAGAACAAATAAATG | 418 |
| AGACAATAATTATTAAAAGGTGATCTATT | 324 | ACTCAGCCTGTTTCTGG | 419 |
| TTAGCGAGTGCCCATT | 325 | CCTGACAGACAATAAAAGGC | 420 |
| TGTCCCACTTGATTCAGT | 326 | GCTTGATAGGTAGGTACTCA | 421 |
| CGTGAGTACCCATTCTCT | 327 | CATGCAAATTTTGCTGAAGT | 422 |
| CCAAAGACAACTTCATTAGACT | 328 | CCTTCCTTGATCATCTTGTAGA | 423 |
| GTATTTATTTCAGTGTTACTTACCTG | 329 | AGTTAAGGACTCTGAAGATGT | 424 |
| GGATCATATTCGTCCACAAA | 330 | GTGTGACATGTTCTAATATAGTCA | 425 |
| CTTTCTCCAGCTAATTCATCT | 331 | GCTCCATGCAGATACTGA | 426 |
| CTGCAGCCAGAAAGACT | 332 | CCTGGCACCCAAACAT | 427 |
| TCCTCTCGTTTCCTTACAT | 333 | GCTTCCCAAACACTTAGAC | 428 |
| CAAAGCAAGCCAGATTCT | 334 | AAGCAGTGCTCATGATTG | 429 |
| GCACTGGGTCAAAGTCT | 335 | TTGGGCTTACACTTCGG | 430 |
| CAGTGCTAACCAAGTTCTT | 336 | AACCACAAAAGTATACTCCATG | 431 |
| CGCTCCTGGGAATCT | 337 | GGATGGCTGGCTTACA | 432 |
| CAGTCAAGGTTGCTGATT | 338 | CATCTGACTTGGTGGTAAAC | 433 |
| GGCGTCAGGAACTG | 339 | CGGAGCTTCCTGAGTG | 434 |
| CGGCCTCGATCTTGTA | 340 | GCCCCTCTCTGATTGTC | 435 |
| CAGCTCCTCCTCGC | 341 | GGTGGTGGTGCTGATG | 436 |
| GGTGGGATCATATTCATCTAC | 342 | CGCCAATTAACCCTGATTA | 437 |
| GTCTGAACTGAAGATAATGACT | 343 | GGATTTAAGCCTGATTGAACA | 438 |
| TGTCCACCGTGATCTG | 344 | ACCAGTGAGGGAAGTGA | 439 |
| GTAAGTGTTACTCAAGAAGC | 19 | ATAGGATATTGTATCATACCAATTTCT | 20 |
| TCCACAGCTACACCATATAT | 21 | AGCATCAGCATTTGACTTTA | 22 |
| TACACAGACACTCTAGTATCTG | 23 | GAAGGTTTGACTGCCATAAA | 24 |
| ATGACAAAGAACAGCTCAAA | 25 | GAGATCAGCCAAATTCAGTT | 26 |
| GATGTGTTACAAGGCTTATCTA | 27 | GCCTCTTGCTCAGTTTTATC | 28 |
| GAGGCTTTGGAGTATTTCA | 29 | CTGCTGAGAGTTATTAACAGT | 30 |
| GCTTTTGGAGTCCTATTGT | 31 | CACAAACTAGAGTCACACAC | 32 |
| GGGTTTTGGGCTGATATTA | 33 | CCACAGAACTGAAGGTTAAT | 34 |
| TTATCCATTGAATTTATTTAATCTTTCTAG | 35 | GGGATGTGCGGGTATATT | 36 |
| GTCTTGCAGTAAGAGATTGT | 37 | TCTTTGCTGTACCGCT | 38 |
| GTTTCTTTTGCCTGCA | 39 | TGGATAAGGTCTGGTTTAATG | 40 |
| GCTACAATTCAGGATGAGTTA | 41 | TCTTCTGCTATCACCATCTTT | 42 |
| CCATCATGATGAGAAGACAT | 43 | TTGCTGGAGATACATACACT | 44 |
| TCGTCTGGGAACTATACTC | 345 | GGTAAATGGACAAGAACACT | 440 |

TABLE 2-continued

Primer Pair Mix Pool 2

| Forward Primer Sequence | SEQ ID NO: | Reverse Primer Sequence | SEQ ID NO: |
|---|---|---|---|
| TGTACTGCTCCCAGAAGA | 346 | GCCCAGTTCCCTTTCTAC | 441 |
| TGCACCAGGAGTTTGTA | 347 | TCTGGCTGCGAGTTATAAT | 442 |
| GAGGGTGTCCTGTGT | 348 | CAGCTTTGCCCATGAAAC | 443 |
| GCCACAGCAGTCTGAAA | 349 | CCAGGCAGCGGTAGTA | 444 |
| AGGTTCGCTGCTTTTAATC | 350 | GCTACTGGCCGGAAAG | 445 |
| CAGCTTCTGCCATCTCT | 55 | AGCAGCCGCAGAAAT | 56 |
| GTGGCTTTTTGTTTGTTTG | 57 | CACTCTAACAAGCAGATAACT | 58 |
| TACTTGTTAATTAAAAATTCAAGAGTTTT | 59 | CTTAGCCATTGGTCAAGATC | 60 |
| ACAATCATGTTGCAGCA | 61 | AAAAACATCAAAAAATAACTTACCTTTT | 62 |
| AGAGGCGCTATGTGTATTA | 63 | CATGGAAGGATGAGAATTTCA | 64 |
| GGAAGACAAGTTCATGTACT | 65 | CTGTCCTTATTTTGGATATTTCTC | 66 |
| ATTAATTAAATATGTCATTTCATTTCTTTTC | 67 | GCTATCGATTTCTTGATCACA | 68 |
| TGAGTCATATTTGTGGGTTTTC | 69 | TGATCAGGTTCATTGTCACTAA | 70 |
| CCCGGGGATTAAAGC | 351 | TCAGATGTGCTGTTGAGAC | 446 |
| GGTCAGCTACTCCTCTTC | 352 | AGGATGGCCTCTGTCT | 447 |
| CCCCTCCTTCCTAGAGA | 353 | GAGCAACACCCACACTTA | 448 |
| GTGCTGCATTTCAGAGAA | 354 | CAGCTGGCCTTACCAT | 449 |
| GTGCAGAACATCAAGTTCA | 355 | GTAGCTGTGCATGTCCT | 450 |
| TGGCTTTGTGCTCATTAC | 356 | GGAGGTGGGTGTCTTTAT | 451 |
| CTGCTCTCAGGTTGACT | 357 | GTCGTGGGACACAGTG | 452 |
| GAGCTGGGGACTCTT | 358 | GGTGCGGGAGTGAATAG | 453 |
| CAGGAGTCATGACTCTGTT | 359 | GGAGGGTGCAGTGTTG | 454 |
| TGGCCTTTGACCTCAAT | 360 | CTCCAGAAGCTTGAACTCT | 455 |
| GCCCGCAGGTACTT | 361 | CTAGCACGTGCCTACC | 456 |
| ATCCTCCGGCTGAAG | 362 | CCTGAGTGTAGATGATGTCA | 457 |
| CTGGAGTGAGCCCTG | 363 | ACTCAGGTACTGTGTATATACTT | 458 |
| GCAGTGCTAGGAAAGAG | 364 | GAAGAGAATCTCCGCAAG | 459 |
| TGCAGGGTGGCAA | 365 | GCACTGGCCTCATCTTG | 460 |
| CGTCATGTGCTGTGAC | 366 | GCCCTGACTTTCAACTCT | 461 |
| GTGTTTCTGTCATCCAAATAC | 367 | AGCGCTGCTCAGATAG | 462 |
| TGCCCTGGTAGGTTTTC | 368 | ACCCAGGTCCAGATGAA | 463 |
| CAAGGGGACTGTAGAT | 369 | ACTGACTTTCTGCTCTTGT | 464 |

Another aspect of the methods of the present techonology is that the 231 amplicons generated by their respective forward and reverse primer pairs shown in Tables 1 and 2 map to genes or gene regions not typically tested in a given tumor type. For example, typically tested genes or gene regions include EGFR exons 18-21, KRAS exons 1-2, and ALK translocations for lung cancer; KRAS/NRAS exons 1-2, and PIK3CA exons 9 and 20 for colorectal cancer; BRAF exon 15, and KIT for melanoma; and KIT and PDGFRa for gastrointestinal stromal tumors.

In some embodiments, a single primer or one or both primers of a primer pair comprise a specific adapter sequence (also referred to as a sequencing adapter) ligated to the 5' end of the target specific sequence portion of the primer. This sequencing adapter is a short oligonucleotide of known sequence that can provide a priming site for both amplification and sequencing of the adjoining, unknown target nucleic acid. As such, adapters allow binding of a fragment to a flow cell for next generation sequencing. Any adapter sequence may be included in a primer used in the present technology. In certain embodiments, amplicons corresponding to specific regions of AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STKl1, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN are amplified using primers that contain an oligonucleotide sequencing adapter to produce adapter tagged amplicons.

In other embodiments, the employed primers do not contain adapter sequences and the amplicons produced are subsequently (i.e. after amplification) ligated to an oligonucleotide sequencing adapter on one or both ends of the amplicons. In some embodiments, all forward amplicons (i.e., amplicons extended from forward primers that hybridized with antisense strands of a target nucleic acid) contain the same adapter sequence. In some embodiments when double stranded sequencing is performed, all forward amplicons contain the same adapter sequence and all reverse amplicons (i.e., amplicons extended from reverse primers that hybridized with sense strands of a target segment) contain an adapter sequence that is different from the adapter sequence of the forward amplicons. In some embodiments, the adapter sequences further comprise an index sequence (also referred to as an index tag, a "barcode" or a multiplex identifier (MID)).

In some embodiments, the adapter sequences are P5 and/or P7 adapter sequences that are recommended for Illumina sequencers (MiSeq and HiSeq). See, e.g., Williams-Carrier et al., *Plant J.*, 63(1):167-77 (2010). In some embodiments, the adapter sequences are P1, A, or Ion Xpress™ barcode adapter sequences that are recommended for Life Technologies sequencers. Other adapter sequences are known in the art. Some manufacturers recommend specific adapter sequences for use with the particular sequencing technology and machinery that they offer.

Additionally or alternatively, in some embodiments of the above methods, amplicons corresponding to specific regions of AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STKl1, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN from more than one sample are sequenced. In some embodiments, all samples are sequenced simultaneously in parallel.

In some embodiments of the above methods, amplicons corresponding to specific regions of AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STKl1, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN from at least 1, 5, 10, 20, 30 or up to 35, 40, 45, 48 or 50 different samples are amplified and sequenced using the methods described herein.

Additionally or alternatively, in some embodiments of the method, amplicons derived from a single sample may further comprise an identical index sequence that indicates the source from which the amplicon is generated, the index sequence for each sample being different from the index sequences from all other samples. As such, the use of index sequences permits multiple samples to be pooled per sequencing run and the sample source subsequently ascertained based on the index sequence. In some embodiments, the Access Array™ System (Fluidigm Corp., San Francisco, Calif.) or the Apollo 324 System (Wafergen Biosystems, Fremont, Calif.) is used to generate a barcoded (indexed) amplicon library by simultaneously amplifying the nucleic acids from the samples in one set up.

In some embodiments, indexed amplicons are generated using primers (for example, forward primers and/or reverse primers) containing the index sequence. Such indexed primers may be included during library preparation as a "barcoding" tool to identify specific amplicons as originating from a particular sample source. When adapter-ligated and/or indexed primers are employed, the adapter sequence and/or index sequence gets incorporated into the amplicon (along with the target-specific primer sequence) during amplification. Therefore, the resulting amplicons are sequencing-competent and do not require the traditional library preparation protocol. Moreover, the presence of the index tag permits the differentiation of sequences from multiple sample sources.

In some embodiments, the amplicons may be amplified with non-adapter-ligated and/or non-indexed primers and a sequencing adapter and/or an index sequence may be subsequently ligated to one or both ends of each of the resulting amplicons. In some embodiments, the amplicon library is generated using a multiplexed PCR approach.

Indexed amplicons from more than one sample source are quantified individually and then pooled prior to high throughput sequencing. As such, the use of index sequences permits multiple samples (i.e., samples from more than one sample source) to be pooled per sequencing run and the sample source subsequently ascertained based on the index sequence. "Multiplexing" is the pooling of multiple adapter-tagged and indexed libraries into a single sequencing run. When indexed primer sets are used, this capability can be exploited for comparative studies. In some embodiments, amplicon libraries from up to 48 separate sources are pooled prior to sequencing.

Following the production of an adapter tagged and, optionally indexed, amplicon library, the amplicons are sequenced using high throughput, massively parallel sequencing (i.e., next generation sequencing). Methods for performing high throughput, massively parallel sequencing are known in the art. In some embodiments of the method, the high throughput massive parallel sequencing is performed using 454TM GS FLX™ pyrosequencing, reversible dye-terminator sequencing, SOLiD sequencing, Ion semiconductor sequencing, Helioscope single molecule sequencing, sequencing by synthesis, sequencing by ligation, or SMRT™ sequencing. In some embodiments, high throughput massively parallel sequencing may be performed using a read depth approach.

In some embodiments, the methods of the present technology are useful in detecting at least one mutation in amplicons corresponding to specific regions of AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN in a FFPE tumor sample comprising a heterogeneous tumor. In certain embodiments, 5% of the cells of the heterogeneous tumor harbor at least one mutation in at least one of the plurality of amplicons. In some embodiments, about 10% of the cells of the heterogeneous tumor harbor at least one mutation in at least one of the plurality of amplicons. In some embodiments, about 25% of the cells of the heterogeneous tumor harbor at least one mutation in at least one of the plurality of amplicons. In some embodiments, about 50% of the cells of the heterogeneous tumor harbor at least one mutation in at least one of the plurality of amplicons. In other embodiments, at least 5% of the cells of the heterogeneous tumor harbor at least one mutation in at least one of the plurality of amplicons. In other embodiments, at least 10% of the cells of the heterogeneous tumor harbor at least one mutation in at least one of the plurality of amplicons. In other embodiments, at least 25% of the cells of the heterogeneous tumor harbor at least one mutation in at least one of the plurality of amplicons.

Treatment of Solid Tumors

Disclosed herein are methods for determining whether a patient diagnosed with breast cancer, colorectal cancer, melanoma or lung cancer will benefit from or is predicted to be responsive to treatment with an individual therapeutic agent or a specific combination of therapeutic agents.

In some embodiments, the therapeutic agent(s) comprise one or more of anti-HER-2 therapies, anti-EGFR therapies, PI3K/AKT/mTor pathway inhibitors, kinase inhibitors, Notch pathway inhibitors, BRAF inhibitors, SMO antagonists, ALK/MET inhibitors, ERBB2 antagonists, FGFR3 antagonists, and RAF/MEK/ERK inhibitors.

In certain embodiments, the EGFR tyrosine kinase inhibitor is gefitinib or erlotinib. In certain embodiments, the anti-EGFR therapy is cetuximab.

In some embodiments of the method, the anti-HER-2 therapy is trastuzumab or lapatinib.

Examples of kinase inhibitors include but are not limited to crizotinib, afatinib, Axitinib, bevacizumab, Bosutinib, Cetuximab, Dasatinib, Erlotinib, Fostamatinib, Gefitinib, Imatinib, Lapatinib, Lenvatinib, Nilotinib, Panitumumab, Pazopanib, Pegaptanib, Ranibizumab, Ruxolitinib, Sorafenib, Sunitinib, Trastuzumab, and Vemurafenib.

Examples of BRAF inhibitors include, but are not limited to GDC-0879, SB590885, Encorafenib, RAF265, TAK-632, PLX4720, CEP-32496, AZ628, Sorafenib Tosylate, Sorafenib, Vemurafenib (Zelboraf) and Dabrafenib (GSK2118436).

Examples of RAF/MEK/ERK inhibitors include, but are not limited to Vemurafenib (Zelboraf) and Dabrafenib (GSK2118436), Encorafenib, TAK-632, PLX4720, MLN2480, Cobimetinib (GDC-0973), MEK 162, RO5126766, GDC-0623, VTXIle, Selumetinib (AZD6244), PD0325901, Trametinib (GSK1120212), U0126-EtOH, PD184352 (CI-1040), Refametinib, PD98059, BIX02189, Binimetinib, Pimasertib (AS-703026), SL327, BIX02188, AZD8330, TAK-733, PD318088, SCH772984, and FR 180204.

Examples of PI3K/AKT/mTor pathway inhibitors include, but are not limited to BKM120, BEZ235, Pictilisib (GDC-0941), LY294002, CAL-101 (Idelalisib), GNE-317, PI-3065, HS-173, PI-103, NU7441, GSK2636771, VS-5584, CZC24832, Duvelisib, TG100-115, A66, YM201636, CAY10505, GSK1059615, PF-04691502, PIK-75, PIK-93, AS-605240, BGT226, AZD6482, Voxtalisib, Alpelisib, CUDC-907, IC-87114, Omipalisib, TG100713, Gedatolisib, CH5132799, PKI-402, BAY 80-6946, TGX-221, XL147, PIK-90, PIK-293, PIK-294, 3-Methyladenine, Quercetin, Wortmannin, ZSTK474, AS-252424, AS-604850, everolimus, and Apitolisib.

Examples of Notch pathway inhibitors include, but are not limited to FLI-06, LY411575, Dibenzazepine, RO4929097, Compound E, Z-Leu-Leu-Nle-CHO, SAHM1, TR4 and Semagacestat.

Examples of SMO antagonists include, but are not limited to Purmorphamine, Taladegib (LY2940680), Cyclopamine, Vismodegib (GDC-0449), LDE225, Glasdegib (PF-04449913), PF-5274857, TAK-441, SANT-1, BMS-833923, GANT61 and IPI-926.

Examples of ERBB2 antagonists include, but are not limited to Lapatinib, Canertinib, CP-724,714, AZD8931, AEE788, Tyrphostin AG 879, Mubritinib, and Pertuzumab.

Examples of FGFR3 antagonists include, but are not limited to BGJ398 (NVP-BGJ398), AZD4547, LY2874455, Dovitinib Dilactic acid, Dovitinib, Dovitinib Lactate, CH5183284, and Nintedanib.

Examples of ALK inhibitors include, but are not limited to Crizotinib, TAE684, Alectinib, Ceritinib, AP26113, AZD3463, and ASP3026.

Examples of MET inhibitors include, but are not limited to Crizotinib, PHA-665752, SU 1274, SGX-523, BMS-777607, JNJ-38877605, Tivantinib, PF-04217903, MGCD-265, Capmatinib, AMG 208, MK-2461, AMG 458, NVP-BVU972, and Tepotinib.

The BRAF inhibitor vemurafenib is the most common targeted therapy for melanoma and is used treat BRAF V600 mutation-positive tumors. In addition, sequencing for KIT mutations may also be performed to assess the likely effectiveness of treatment with imatinib mesylate. Thus, in some embodiments, the present disclosure provides methods for determining whether a melanoma patient is likely to respond to treatment with vemurafenib or MEK inhibitors. Also provided herein are methods for determining whether a melanoma patient is likely to respond to treatment with a drug that inhibits PIK3CA or MET activity.

Colorectal cancer specimens are generally submitted for detection of mutations in genes downstream of EGFR to identify tumors with a low likelihood of response to anti-EGFR therapies such as cetuximab. NCCN guidelines identify mutations in the KRAS, NRAS, or BRAF as indicators of lack of responsiveness to such therapies, and clinical evidence suggests that PIK3CA and PTEN mutations are also indicators of resistance. See Er T. et al., BioMed Research International 2014:1-8 (2014); Bokemeyer et al., Ann Oncol. 22(7): 1535-46 (2011). Thus, in some embodiments, the present disclosure provides methods for determining whether a colorectal cancer patient is likely to respond to treatment with anti-EGFR therapy (e.g., cetuximab).

For lung cancer specimens, the current guideline-recommended testing (CAP, IASL, AMP) is to prioritize testing for EGFR mutations, which directly identifies EGFR TKI responders. These guidelines also state that EGFR mutation-negative specimens should be followed up with ALK rearrangement testing to identify likely responders to the ALK c-MET inhibitor crizotinib. KRAS mutation testing may be used as a means to identify non-responders to EGFR tyrosine kinase inhibitors such as gefitinib and erlotinib. However, this does not rule-in a TKI responder, as EGFR tyrosine kinase inhibition by these drugs is specific to tumors harboring tyrosine kinase domain mutations in EGFR. In some embodiments, the present disclosure provides methods for determining whether a lung cancer patient is likely to respond to treatment with an EGFR TKI. In certain embodiments, the EGFR tyrosine kinase inhibitor is gefitinib or erlotinib. Also provided herein are methods for determining whether a lung cancer patient is likely to respond to treatment with crizotinib. The present disclosure also provides methods for determining whether a lung cancer patient is likely to respond to treatment with vemurafenib, dabrafenib, dasatinib or a MEK inhibitor such as selumetinib.

The primary routine clinical biomarkers for targeted treatment in breast cancer are HER-2 gene amplification/expression (FISH and/or IHC) for anti-HER-2 therapy (e.g., trastuzumab) and ER/PR overexpression for endocrine therapy. In some embodiments, the present disclosure provides methods for determining whether a HER-2 positive patient diagnosed with breast cancer is likely to respond to treatment with anti-HER-2 therapies or trastuzumab emtansine. In some embodiments of the method, the anti-HER-2 therapy is trastuzumab or lapatinib. Also provided herein are methods for determining whether a patient diagnosed with breast cancer is likely to respond to treatment with PI3K/AKT/mTor pathway inhibitors.

In another aspect, the present disclosure provides a method for selecting a subject for treatment with a PI3K/AKT/mTor pathway inhibitor and at least one additional agent comprising (a) extracting genomic DNA from a formalin fixed paraffin-embedded specimen obtained from the subject; (b) generating a library comprising amplicons corresponding to each of a plurality of cancer-related genes, said plurality of cancer-related genes comprising AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN, wherein (i) generating said library proceeds independently of using a bait set comprising nucleic acid sequences that are complementary to at least one of the plurality of amplicons, and (ii) the quality of the genomic DNA extracted from the formalin fixed paraffin-embedded specimen is not assessed using quantitative PCR prior to generating the library; (c) detecting at least one mutation in at least one of the plurality of amplicons; and (d) selecting the subject for treatment with a PI3K/AKT/mTor pathway inhibitor and at least one additional agent, if a mutation in at least one of the amplicons corresponding to PIK3CA, PIK3R1 and PTEN, and a mutation in at least one of the amplicons corresponding to NOTCH1, ERBB2, BRAF, PTCH1, SMO, EGFR, KRAS, DDR2, MAP2K1, FGFR3, NRAS, MET, and FBXW7 are detected.

In some embodiments of the method, the at least one additional agent is selected from Notch pathway inhibitors, BRAF inhibitors, SMO antagonists, MET inhibitors, ERBB2 antagonists, or any combination thereof. In some embodiments of the method, the at least one additional agent is selected from Notch pathway inhibitors, FGFR3 antagonists, RAF/MEK/ERK inhibitors, or any combination thereof. In some embodiments, the at least one additional agent is RAF/MEK/ERK inhibitors, FGFR3 antagonists, SMO antagonists or any combination thereof.

In another aspect, the present disclosure provides a method for selecting a subject for treatment with a EGFR tyrosine kinase inhibitor and at least one additional agent comprising: (a) extracting genomic DNA from a formalin fixed paraffin-embedded specimen obtained from the subject; (b) generating a library comprising amplicons corresponding to each of a plurality of cancer-related genes, said plurality of cancer-related genes comprising AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN, wherein (i) generating said library proceeds independently of using a bait set comprising nucleic acid sequences that are complementary to at least one of the plurality of amplicons, and (ii) the quality of the genomic DNA extracted from the formalin fixed paraffin-embedded specimen is not assessed using quantitative PCR prior to generating the library; (c) detecting at least one mutation in at least one of the plurality of amplicons; and (d) selecting the subject for treatment with a EGFR tyrosine kinase inhibitor and at least one additional agent, if a mutation in at least one of the amplicons corresponding to EGFR, and a mutation in at least one of the amplicons corresponding to KRAS, PIK3R1 and BRAF are detected.

In some embodiments of the method, the at least one additional agent is selected from BRAF inhibitors, RAF/MEK/ERK inhibitors, PI3K/AKT/mTor pathway inhibitors or any combination thereof.

Kits

The present disclosure also provides kits for detecting alterations in target nucleic acid sequences corresponding to the preselected set of cancer-related genes described herein.

Kits of the present technology comprise one or more primer pairs that selectively hybridize and are useful in amplifying one or more of the genes selected from the group consisting of AKT1, ERBB2, FOXL2, IDH2, NRAS, RET, ALK, ERBB4, GNA11, KIT, PDGFRA, SMO, BRAF, FBXW7, GNAQ, KRAS, PIK3CA, SIK11, C1NNB1, FGFR2, GNAS, MAP2K1, PIK3R1, TP53, DDR2, FGFR3, HRAS, MET, PTCH1, EGFR, FGFR4, IDH1, NOTCH1, and PTEN.

In some embodiments, the kits of the present technology comprise a single primer pair that hybridizes to a region or exon of a single gene selected from the group consisting of AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN. In other embodiments, the kits of the present technology comprise multiple primer pairs that hybridize to one or more regions or exons of a single gene selected from the group consisting of AKT1, ERBB2, FOXL2, IDH2, NRAS, RET, ALK, ERBB4, GNA11, KIT, PDGFRA, SMO, BRAF FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN. In certain embodiments, the kits of the present technology comprise multiple primer pairs comprising a single primer pair that specifically hybridizes to a region or exon of a single gene for each of AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and P7EN. In certain embodiments, the kits of the present technology comprise multiple primer pairs comprising more than one primer pair that hybridizes to one or more regions or exons for each of AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN.

Thus, it is contemplated herein that the kits of the present technology can comprise primer pairs that recognize and specifically hybridize to one or more regions or exons of one or more genes selected from the group consisting AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN. Alternatively, the kit can comprise primer pairs that will detect one or more mutations selected from the group consisting of BRAF V600E, BRAF V600K, BRAF K483Q, BRAF G466V, BRAF G464V, BRAF E501V, BRAF E501K, EGFR ΔE746_A750, EGFR R680Q, EGFR G598E, KRAS A146T, KRAS R68M, KRAS L19F, KRAS G12V, KRAS G12D, KRAS G12C, KRAS G13D, KRAS G13C, KRAS G12A, KRAS G12S, KRAS Q22K, NRAS Q61K, NRAS Q61R, NRAS G12R, NRAS G12D, PIK3CA C420R, PIK3CA G106R, PIK3CA R38H, PIK3CA E453K, PIK3CA H1044R, PIK3CA N1044K, PIK3CA E545K, PIK3CA Q546H, PIK3CA H1047R, PIK3CA H1043L, PIK3CA M1043V, PIK3CA E542K, PIK3CA E542Q, PIK3CA T1053A, PIK3CA I121V, PIK3CA H1047L, ERBB2 L755S, ERBB2 S310Y, ERBB2 D769Y, ERBB2 S255R, DDR2 H92Y, DDR2 R31L, DDR2 L34P, DDR2 P381R and DDR2 K392N.

In some embodiments, the kits comprise one or more primer pairs disclosed in Table 1. In some embodiments, the kits comprise one or more primer pairs disclosed in Table 2. In some embodiments, the kits comprise two or more primer pairs disclosed in Table 1 and/or Table 2.

In some embodiments, the kits further comprise buffers, enzymes having polymerase activity, enzymes having polymerase activity and lacking 5'-3' exonuclease activity or both 5'→3' and 3'→5' exonuclease activity, enzyme cofactors such as magnesium or manganese, salts, chain extension nucleotides such as deoxynucleoside triphosphates (dNTPs), modified dNTPs, nuclease-resistant dNTPs or labeled dNTPs, necessary to carry out an assay or reaction, such as amplification and/or detection of alterations in target nucleic acid sequences corresponding to the specific set of cancer-related genes disclosed herein.

In one embodiment, the kits of the present technology further comprise a positive control nucleic acid sequence and a negative control nucleic acid sequence to ensure the integrity of the assay during experimental runs. A kit may further contain a means for comparing the levels and/or activity of one or more of the preselected set of cancer-related genes described herein in a tumor sample with a reference nucleic acid sample (e.g., a non-tumor sample). The kit may also comprise instructions for use, software for automated analysis, containers, packages such as packaging intended for commercial sale and the like.

The kits of the present technology can also include other necessary reagents to perform any of the NGS techniques disclosed herein. For example, the kit may further comprise one or more of: adapter sequences, barcode sequences, reaction tubes, ligases, ligase buffers, wash buffers and/or reagents, hybridization buffers and/or reagents, labeling buffers and/or reagents, and detection means. The buffers and/or reagents are usually optimized for the particular amplification/detection technique for which the kit is intended. Protocols for using these buffers and reagents for performing different steps of the procedure may also be included in the kit.

The kits of the present technology may include components that are used to prepare nucleic acids from a solid tumor test sample for the subsequent amplification and/or detection of alterations in target nucleic acid sequences corresponding to the specific set of cancer-related genes disclosed herein. Such sample preparation components can be used to produce nucleic acid extracts from tissue samples. The test samples used in the above-described methods will vary based on factors such as the assay format, nature of the detection method, and the specific tissues, cells or extracts used as the test sample to be assayed. Methods of extracting nucleic acids from samples are well known in the art and can be readily adapted to obtain a sample that is compatible with the system utilized. Automated sample preparation systems for extracting nucleic acids from a test sample are commercially available, e.g., Roche Molecular Systems' COBAS AmpliPrep System, Qiagen's BioRobot 9600, and Applied Biosystems' PRISM™ 6700 sample preparation system.

EXAMPLES

Example 1: Design of the Solid Tumor Screening NGS Assay of the Present Technology Initial experimentation efforts were directed towards designing a more focused, highly sensitive solid tumor screening assay that could provide a general overview of the clinically relevant mutations in multiple solid tumor types while using extremely small amounts of DNA derived from FFPE tissue samples (~10 ng). A set of 34 cancer-related genes was carefully selected on the basis of NCCN guideline recommendations, prevalence of somatic mutations in solid tumors, and potential for informing treatment selection in solid tumor patients (Table 3).

TABLE 3

Solid Tumor Screening Panel

AKT1
ALK
BRAF
CTNNB1
DDR2
EGFR
ERBB2
ERBB4
FBXW7
FGFR2
FGFR3
FGFR4
FOXL2
GNA11
GNAQ
GNAS
HRAS
IDH1
IDH2
KIT
KRAS
MAP2K1
MET
NOTCH1
NRAS
PDGFRA
PIK3CA
PIK3R1
PTCH1
PTEN
RET
SMO
STK11
TP53

Of the 34 genes selected, many have mutations with known or potential clinical significance in at least 2 (65%) or 3 (40%) solid tumor types (COSMIC, mycancergenome.org, clinicaltrials.gov). Moreover, nearly 80% of these 34 genes are mutated in at least 1% of melanoma, lung cancer, and colorectal cancer (colorectal cancer) cases. The solid tumor screening panel was designed to assay for mutations in target nucleic acid sequences corresponding to specific regions of the 34 genes listed in Table 3 (instead of every exon of the entire gene). The selection of these particular target nucleic acid sequences (or amplicons) was based on the potential for informing treatment decisions, reported mutation frequency, known hot spots etc.

The use of bait sets to enrich for target nucleic sequences corresponding to specific regions of AKT1, ERBB2, FOXL2, IDH2, NRAS, RET, ALK, ERBB4, GNA11, KIT PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN from FFPE samples is significantly inefficient because capture experiments yield about half the number of reads for the interrogated target nucleic sequences compared to that observed with PCR amplification, thereby compromising the overall sensitivity of the screening assay.

As such, subsequent attempts focused on the development of an NGS screening assay that was wholly based on PCR (i.e., amplicon-based library preparation followed by NGS) in order to detect genetic alterations in amplicons corresponding to specific regions of AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN. One of the technical challenges that arose while developing the multiplex PCR method described herein was the optimal selection of over one hundred primer pairs that simultaneously hybridize and amplify target nucleic acid sequences corresponding to specific regions of the 34 cancer-related genes disclosed herein in a single reaction. Achieving the proper balance of primer pairs was a significant concern because differences in annealing efficiency of different primer pairs result in a strong bias in the amplification of the different amplicons, leading to insufficient coverage of some amplicons in a sample and strongly reducing the sensitivity of the assay. In order to maximize the sequencing capacity, the amplification levels should be similar among all amplicons. Furthermore the presence of a large number of different primers results in a strongly increased risk of primer dimer formation diminishing the possibility of reproducible amplifying small amounts of target nucleic acids. To account for the fragmentation observed with FFPE DNA, amplicons were designed to be 126-183 bp. The optimized set of PCR primer pairs useful in the methods of the present technology are disclosed in Tables 1 and 2.

Example 2: Reproducibility and Analytical Sensitivity of the Solid Tumor Screening Assay of the Present Technology Reproducibility. Inter-assay precision of sequencing performance was assessed by testing three clinical FFPE specimens containing known variants (BRAF G466Y, TP53 R175H, DDR2 L34P, EGFR E865G, EGFR E866V, TP53 R248W, Notch Q2406A, TP53 A159_M160insRA) with mutation frequencies ranging between 4.6% and 62.3% over three different runs. See FIG. 2. For intra-assay precision, three FFPE specimens made from cell lines harboring known variants (2 SNV and 1 DEL) with mutation frequencies ranging between 4.8% and 43% were assayed within a single run. See FIG. 3.

As shown in FIG. 2 and FIG. 3, all expected low-frequency variants were detected in inter- and intra-assay replicates. The SD of variant frequency from inter- and intra-assays for all variants tested ranged from 0.11% to 4.5% and 0.6% to 1.9%, respectively, indicating that the solid tumor screening assay of the present technology is highly reproducible.

Analytical Sensitivity. To demonstrate the assay's analytical sensitivity, clinical FFPE specimens with known mutation frequencies ranging between 14% to 78% were mixed with DNA from FFPE tissue that did not contain mutations in the regions of interest at different ratios. The clinical FFPE specimens were mixed at percentages ranging from 2.5% to 78.0%. See Table 4.

TABLE 4

Tumor Sensitivity Assay

| Cell Line Mix | Known Variants | Frequency | | Total Cov | F/R Ref | F/R Var |
|---|---|---|---|---|---|---|
| | | Expected | Observed | | | |
| CRL-2324D | | | | | | |
| 100% | TP53 R175H | 100% | 99.00 | 1991 | 16/4 | 1189/782 |
| 25% | TP53 R175H | 25% | 36.38 | 1971 | 776/478 | 452/265 |
| 10% | TP53 R175H | 10% | 15.55 | 2000 | 1014/675 | 182/129 |
| 5% | TP53 R175H | 5% | 6.80 | 2000 | 1115/749 | 88/48 |
| 2% | TP53 R175H | 2% | 2.00 | 1998 | 1186/772 | 23/17 |
| 0% | TP53 R175H | 0% | Not detected | | | |
| HTB-126 | | | | | | |
| 100% | PIK3R1 N453_T454insN | 100% | 98.64 | 1984 | 20/7 | 1115/842 |
| 25% | PIK3R1 N453_T454insN | 25% | 8.86 | 1986 | 1020/790 | 94/82 |
| 10% | PIK3R1 N453_T454insN | 10% | 4.97 | 1992 | 1116/777 | 58/41 |
| 5% | PIK3R1 N453_T454insN | 5% | 2.31* | 11891 | 7282/4332 | 275 |
| 2% | PIK3R1 N453_T454insN | 2% | Not detected | | | |
| 0% | PIK3R1 N453_T454insN | 0% | Not detected | | | |
| HTB-126 | | | | | | |
| 100% | TP53 V157F | 100% | 100.00 | 1985 | 0/0 | 1148/837 |
| 25% | TP53 V157F | 25% | 11.18 | 1995 | 1369/403 | 168/55 |
| 10% | TP53 V157F | 10% | 5.71 | 1998 | 1157/727 | 68/46 |
| 5% | TP53 V157F | 5% | 2.86 | 1996 | 1129/810 | 32/25 |
| 2% | TP53 V157F | 2% | Not detected | | | |
| 0% | TP53 V157F | 0% | Not detected | | | |

TABLE 4-continued

Tumor Sensitivity Assay

| Cell Line Mix | Known Variants | Frequency | | Total Cov | F/R Ref | F/R Var |
|---|---|---|---|---|---|---|
| | | Expected | Observed | | | |
| HTB-126 | | | | | | |
| 100% | HRAS G12D | 50% | 55.21 | 1391 | 347/276 | 425/343 |
| 25% | HRAS G12D | 12.5% | 3.13 | 1053 | 637/383 | 21/12 |
| 10% | HRAS G12D | 5% | 1.47* | 1157 | 8/9 | 610/530 |
| 5% | HRAS G12D | 2.5% | Not detected | | | |
| 2% | HRAS G12D | 1% | Not detected | | | |
| 0% | HRAS G12D | 0% | Not detected | | | |

*Not detected by variant caller, but visibly present in BAM files and raw read numbers provided (insertion does not break down for/rev reads in IGV.
Not detected, indicates variant present at <2% or completely absent.

Variants in nine target regions were detected, seven of which (2 INDELs and 5 SNPs) were detected in the mixed sample at or near 5% (5%-7%). Variants were not detected in the mixed sample at <2.5%. Although INDELs were detectable in the mixed sample at or near 5%, the observed frequencies of some deletions tended to be lower than expected (2.5-5%). Therefore, based on these data, analytical sensitivity of this assay was defined as 5% for SNPs and 10% for INDELs.

Example 3: Methods for Validating the Efficacy of the Solid Tumor Screening Assay of the Present Technology with FFPE Samples This Example demonstrates that the solid tumor screening assay of the present technology has improved breadth of coverage and sensitivity over Sanger sequencing methods and can effectively profile actionable mutations in clinically relevant genes in several major solid tumor types.

Patients and Specimens. This study included de-identified FFPE samples submitted to Quest Diagnostics Nichols Institute, San Juan Capistrano, Calif. for tumor marker analysis. The diagnosis of each cancer was confirmed by pathology review. A total of 133 FFPE samples were initially collected. Twelve specimens were excluded because of insufficient DNA yield (<10 ng) and 121 tumor specimens (33 colorectal cancer, 27 lung cancer, 31 melanoma and 30 breast cancer) were included in this study.

The clinical characteristics of the 121 patients that provided the usable tumor specimens are shown in FIG. 1. The median patient ages for each cancer type ranged between 57 and 68 years. The most common tissue source for melanoma, lung cancer, and colorectal cancer specimens was resection, while most breast cancer specimens originated from biopsies. Stage IV patients accounted for 35.5% and 27.3% of melanoma, and colorectal cancer specimens respectively. Stage I patients accounted for 57% of breast cancer specimens. The most frequent tumor grade designations were "poorly differentiated" in lung cancer (37%) and breast cancer (40%), and "moderately differentiated" in colorectal cancer (39.4%); there was no grading information available for most melanoma specimens (83.9%). See FIG. 1.

DNA Extraction. Hematoxylin and eosin-stained slides for each sample were analyzed by a pathologist to identify tumor-rich areas and estimate tumor fraction. FFPE samples containing >25% tumor cells (based on morphology) in a selected area were included in the study. Sections were subjected to manual macrodissection, and total DNA was extracted from one to five 10-μm unstained sections depending on the tumor area using Roche DNA extraction kit (Roche Molecular Diagnostics, Indianapolis, Ind.). DNA quantification was performed using a Qubit DNA HS assay kit (Life Technologies, Carlsbad, Calif.). Samples with at least 10 ng of DNA were selected for NGS analysis. No further evaluation of the quality of the extracted genomic DNA was conducted prior to generating the amplicon-based library (i.e., the quality of the extracted genomic DNA was not assessed using quantitative PCR). This is because earlier comparison studies revealed that there was no significant improvement in using qPCR-based quality control methods prior to performing the NGS-based methods of the present technology compared to Qubit quantitation (data not shown).

Ion Torrent PGM Library Preparation. A PCR amplicon library was generated from the extracted genomic DNA of each sample. Targeted regions within the 34 genes were amplified using 231 primer pairs (listed in Tables 1 and 2) in two primer pools.

Briefly, PCR was performed in 2×10-μL volumes, each containing 5 to 20 ng of genomic DNA; forward and reverse primers listed in either Table 1 or 2 (primer concentrations optimized for balanced amplification); 440 μM (each) dATP, dCTP, dGTP, and dTTP; 5 mM $MgCl_2$; 57 mM KCl; and 0.6 units of Gold Polymerase (Celera, Alameda, Calif.). PCR amplification on was carried out on a ABI9700 thermal cycler under the following conditions:

| Temperature | Time | Cycle |
|---|---|---|
| 95° C. | 12 min | 1 cycle |
| 95° C. | 15 sec | 23 cycles |
| 62° C. | 2 min | |
| 62° C. | 7 min | 1 |
| 99° C. | 10 min | 1 |

Sequencing adaptors with short stretches of index sequences (Ion Xpress™ Barcode Adapters 1-16 Kit, Life Technologies, Carlsbad, Calif.) that enabled sample multiplexing were ligated to the amplicons using the PrepX PGM DNA library kit on the Apollo 324 system (Wafergen Biosystems, Fremont, Calif.). The amplicon library was then nick-translated using Platinum PCR SuperMix High Fidelity under the following conditions: 1 cycle at 72° C. for 20 minutes and 1 cycle at 95° C. for 5 minutes. The library was quantified using the Qubit DNA HS assay kit (Life Technologies, Carlsbad, Calif.).

Sequencing Template Preparation. Pooled libraries were created by diluting four patient samples (each with distinct barcoding as described above) to balance the concentrations and generate a final working library concentration of 10 pmol/L. Each library pool contained a positive control DNA sample, harboring 8 variants with known frequencies (Horizon Diagnostics, Waterbeach, Cambridge, UK). Each library pool was subjected to emulsion PCR (E-PCR) using an Ion OneTouch 2 template kit on an Ion One-Touch 2 system (Life Technologies, Carlsbad, Calif.), according to the manufacturer's protocol. The Qubit Ion Sphere quality control kit (Life Technologies, Carlsbad, Calif.) was used to estimate the percentage of the Ion Sphere particles (ISPs) with amplified template DNA. Enrichment of ISPs was achieved using the Ion OneTouch kit on the IT OneTouch ES (Life Technologies, Carlsbad, Calif.) according to the manufacturer's protocol.

Sequencing. Enriched ISPs were subjected to sequencing on an Ion 318 Chip using the Ion PGM sequencing kit (Life Technologies, Carlsbad, Calif.) according to the manufacturer's instructions.

Data Analysis. The sequence reads from the Ion Torrent PGM library were aligned using the Ion Torrent Suite software version 3.4 (Life Technologies, Carlsbad, Calif.). The variations were called using the Ion Torrent variant caller using a customized parameter set. Metrics were calculated from the BAM files including coverage for the regions of interest (ROI). Read coverage was calculated as the number of reads across the ROI, where the average Q-score for bases in the read exceeded Q20. Samples with at least 95% of amplicons having 2300 reads with an average quality score of Q20 or better were considered successfully sequenced. For a sequence variant to be considered authentic, sequencing coverage of at least 300 Q20 reads or 10 variant reads and a reported variant frequency of at least 4% was required. Additional metrics recorded included whether the variation was within or adjacent to homopolymer regions, the number of bases at the variation, and the read strand bias. The metrics for the variations were integrated into a custom software application, CLS-Mutation-Review, which can also directly access the Integrated Genome Viewer (IGV) for focused visualization of the aligned reads and identified variation. Manual review of all the variations was performed using the CLS-Mutation Review application. Population variations and positions with known technical issues that had been identified from assay validation studies were tagged within the application to aid the review.

Amplicon Coverage. All 121 specimens were sequenced. On average, 98.6% (range 95-100%, 2.63 SD) of all amplicons met the minimum per-amplicon criteria of >300 reads, indicating adequate amplicon coverage for all 121 specimens.

Sanger Sequencing. Sanger sequencing assays were performed by standard methods. The specific genes and exons tested depended on the cancer type, but included EGFR, KRAS, HRAS, NRAS, BRAF, PIK3CA, TP53, and KIT.

Immunohistochemistry. Estrogen receptor (ER), progesterone receptor (PR), and HER-2 immunohistochemistry (IHC) testing was performed using standard assays. The stained slides were reviewed and classified as ER and PR positive when >1% of tumor cells showed positive nuclear staining. For the HER-2 assay, slides were classified as negative, equivocal, or positive based on CAP guidelines.

FISH. Commercial kits were used to assess HER-2 gene amplification (Vysis PathVysion™ HER-2 DNA Probe Kit; Abbott Laboratories, Des Plaines, Ill.), ALK translocation (Vysis LSI ALK Break Apart Rearrangement Probe Kit; Abbott Laboratories), and ROS1 translocation (Cytocell ROS1 Breakapart kit; CytoCell, Compiegne, France).

Figure 5:
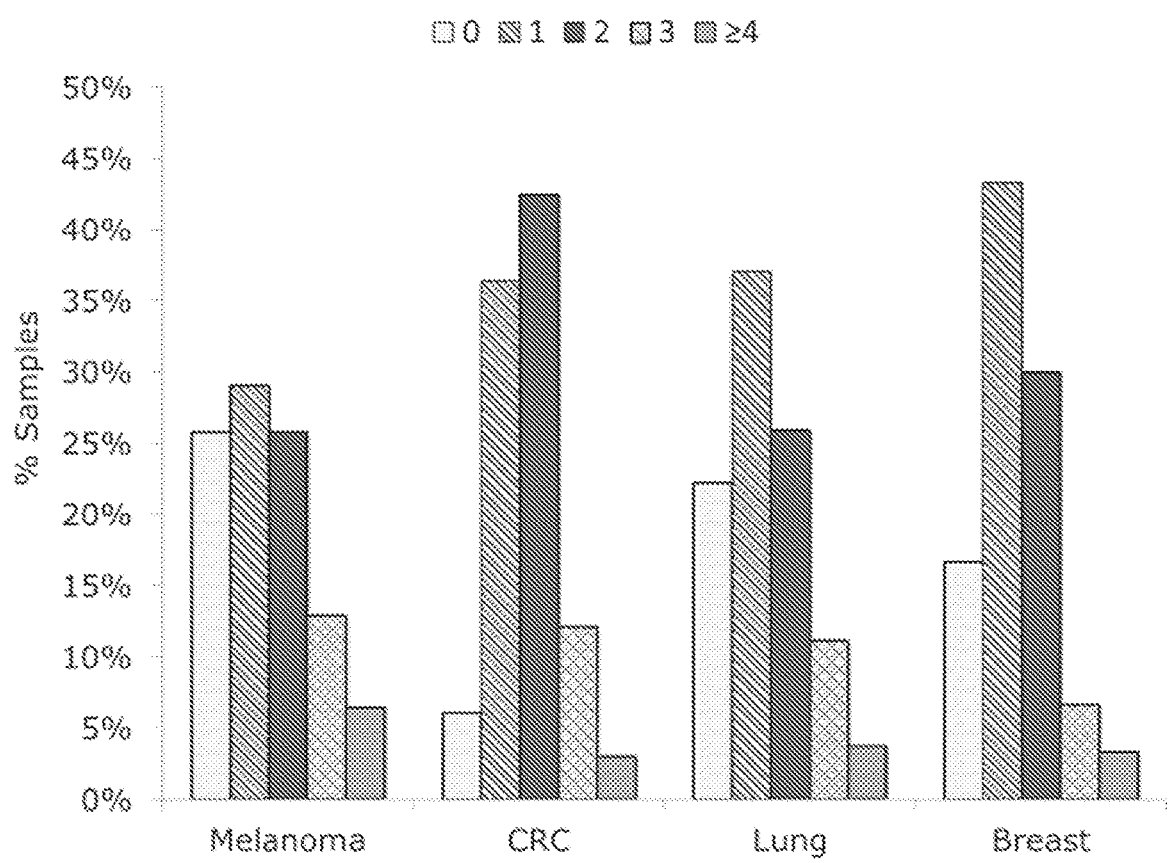
FIG. 5 shows the percentage of FFPE samples by tumor type that harbor multiple co-occurring mutations (as detected by the solid tumor screening panel of the present technology). No tumor sample harbored ≥5 co-occurring mutations.

Example 4: Frequency and Breadth of Mutations Detected by the Solid Tumor Screening Assay of the Present Technology Results. Overall, 83% (100/121) of all FFPE specimens tested harbored at least one mutation, as determined by the solid tumor screening assay of the present technology: 74% (23/31) of melanoma samples; 94% (31/33) of colorectal cancer; 78% (21/27) of lung cancer; and 83% (25/30) in breast cancer (FIG. 5). A single gene mutation was observed in most tumor types i.e., melanoma, lung cancer, and breast cancer. Colorectal cancer was the exception, with a higher frequency of FFPE specimens harboring mutations in two or more genes. FFPE specimens harboring mutations in four or more genes were rarely observed in all tumor types.

Mutations in 62% (21/34) of the genes assayed by the solid tumor screening panel of the present technology were detected. These observations support the selection of the plurality of amplicons that are interrogated in the solid tumor screening assay of the present technology. Of those 21 genes, BRAF, PIK3CA, PIK3RJ, PTEN, and TP53 were mutated in all 4 tumor types; 11 genes were mutated in at least three tumor types; and 17 genes were mutated in at least two tumor types (FIG. 4). Moreover, 53% of all tumors (64/121) harbored mutations in TP53.

The only genes that were found to be mutated in a specific tumor type were STK11 in lung cancer; RET in colorectal cancer, and ERBB2, and ERBB4 in breast cancer. While the vast majority of specimens tested had only one gene mutation, at least 40% of each tumor type had mutations in ≥2 genes per specimen and 10% to 20% of each tumor type had mutations in ≥3 genes per specimen. Furthermore, six specimens harbored two different mutations within the same gene. These findings support the use of a single molecular profiling assay for multiple solid tumor types.

Figure 6A:
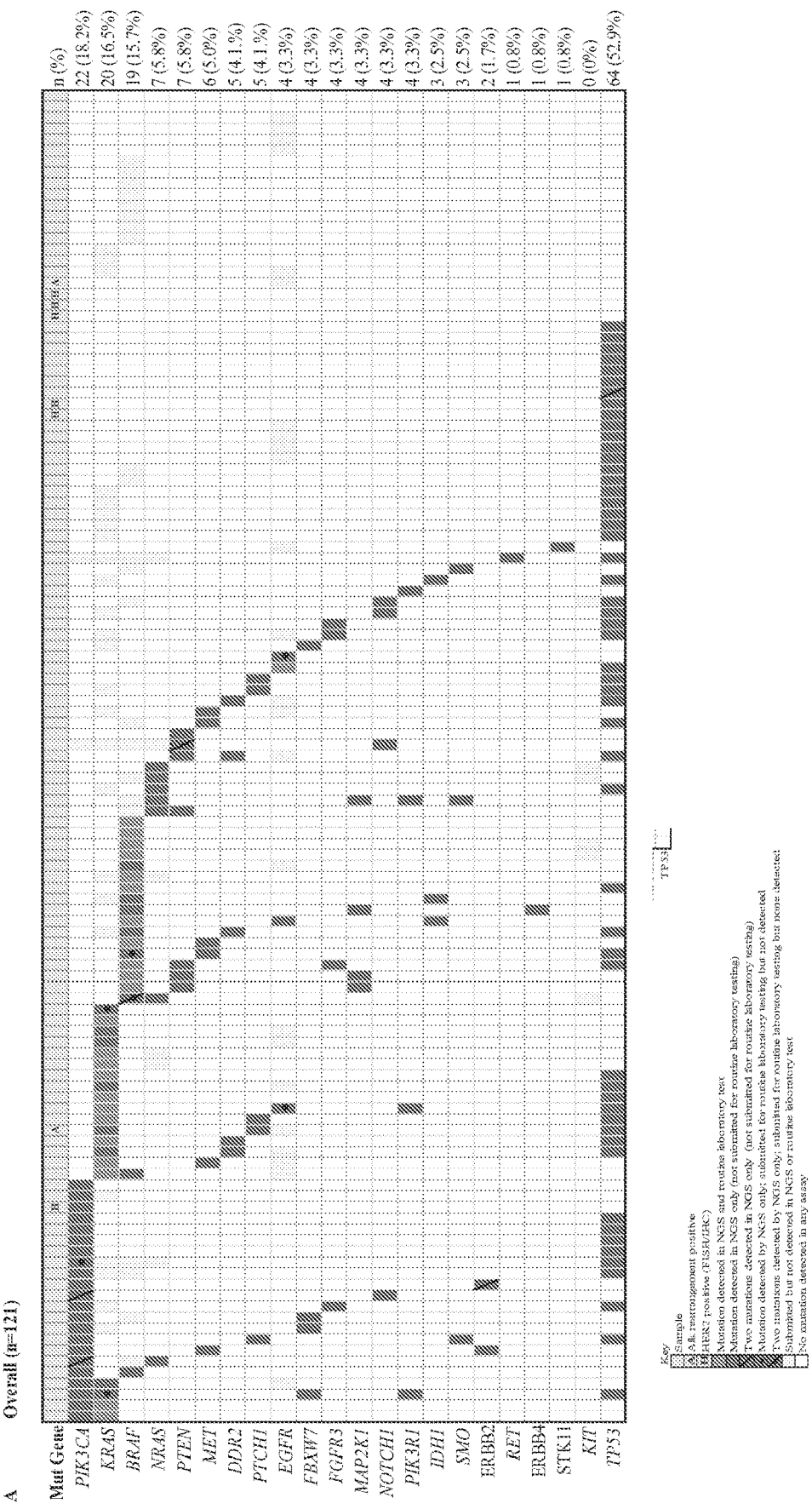
FIG. 6 shows the mutations detected by the solid tumor screening panel of the present technology for each individual specimen (columns) for (A) all tumor types, (B) melanoma, (C) colorectal cancer, (D) lung cancer, and (E) breast cancer. The total number of specimens tested for a given tumor type is also shown. The number of specimens harboring mutations in the gene represented by a given row is provided for each panel (labeled on the right axes for all panels). Specimens harboring 2 mutations within the same gene are also shown. Clinical laboratory results for each specimen are indicated by the figure legend.
Figure 6B:
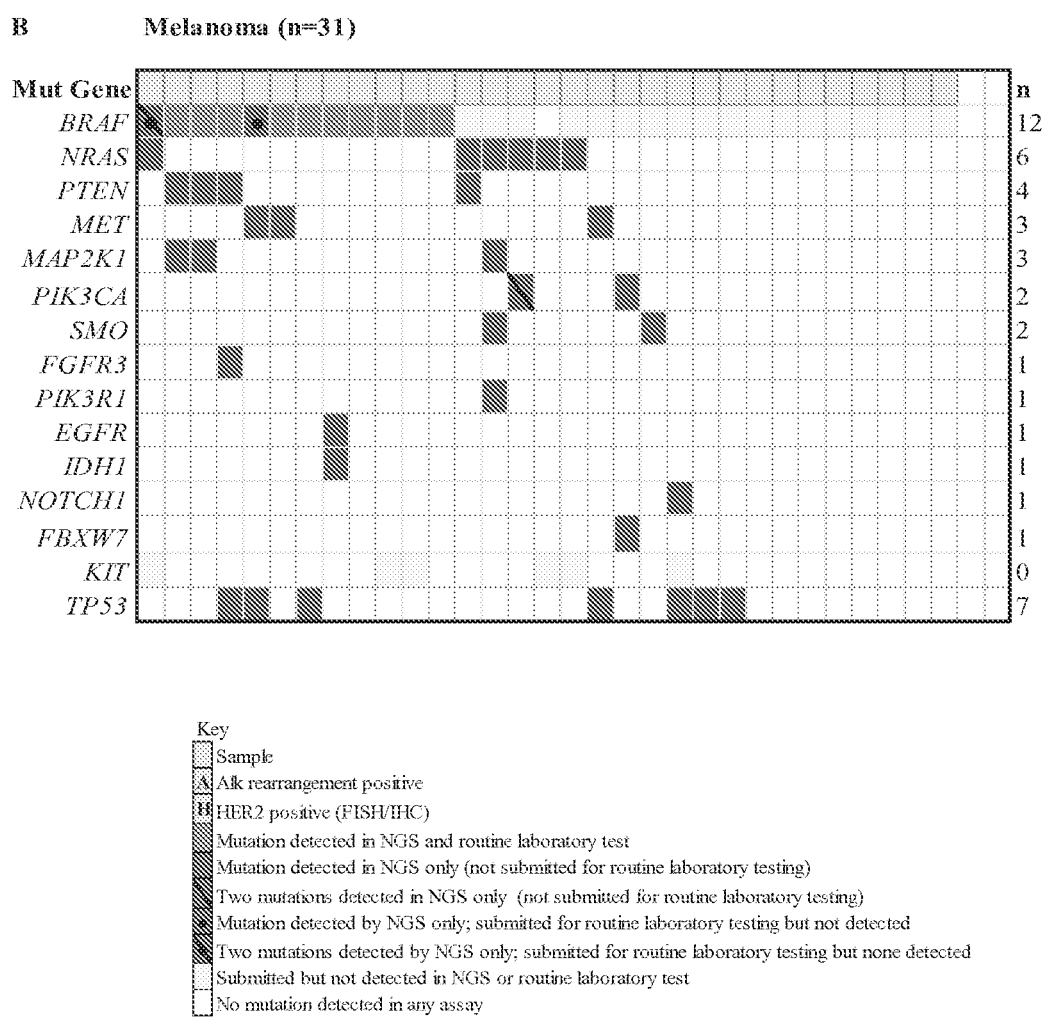

FIG. 6A shows the mutations detected by the solid tumor screening panel of the present technology for each individual specimen for all tumor types. As shown in FIG. 6B, BRAF was the most frequently mutated gene in melanoma samples (12/31; 39%) and included eight specimens with single-nucleotide substitutions (7 at V600E [GTG>GAG] and 1 at K483Q) and 5 with dinucleotide substitutions (V600E, GTG>GAA [n=4]; V600K, GTG>AAG [n=1]). Further, 19% (6/31) of the melanoma specimens had single-nucleotide NRAS substitutions (Q61K [n=2]; Q61R [n=3]; and G12R [n=1]), one of which also had two co-occurring BRAF mutations. Examples of additional mutated genes in the melanoma specimens included PTEN (13%), MET and MAP2K1 (10%), PIK3CA and SMO (6%), and single instances of FGFR3, PIK3R1, EGFR, IDH1, NOTCH1, and FBXW7 (3%). TP53 mutations were also found in 7 (23%) samples (FIG. 6B).

Figure 6C:
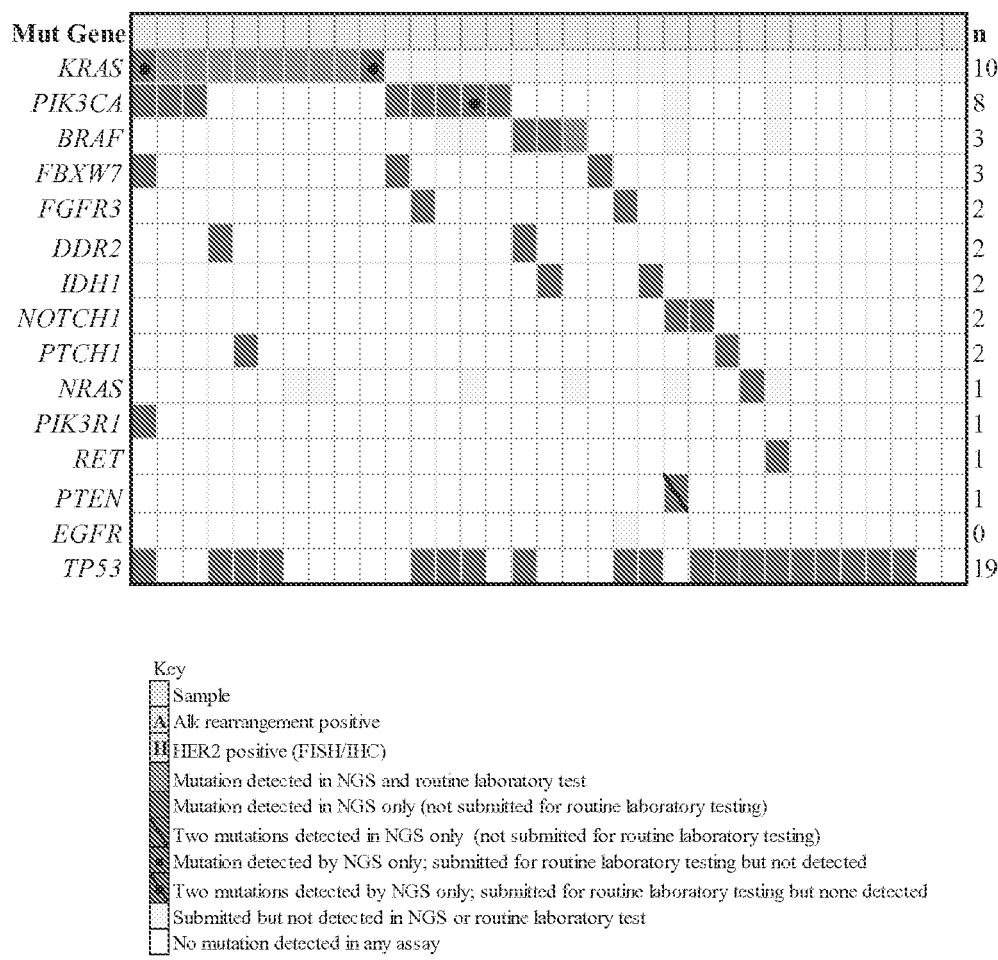

As shown in FIG. 6C, KRAS was the most frequently mutated gene in colorectal cancer samples (10/33 samples; 30%). All KRAS mutations in this group were single-nucleotide substitutions (G12V [n=2], G12D [n=2], G12C [n=1], G13D [n=3], L19F [n=1], and A146T [n=1]). Further, 24% (8/33) of colorectal cancer samples harbored single-nucleotide PIK3CA substitutions (1 each of G106R, R38H, E453K, H1044R, N1044K, E545K, Q546H, and C420R). BRAF mutations were detected in two (6%) of the 33 colorectal cancer samples (V600E [n=1] and G466V [n=1]). Examples of additional mutated genes in the colorectal cancer specimens included DDR2, IDH1, NOTCH1, PTCH1, NRAS, PIK3R1, RET, and PTEN. TP53 was also mutated in 19 (58%) of the samples (FIG. 6C).

As shown in FIG. 6D, 37% (10/27) of the lung cancer specimens harbored single-nucleotide KRAS substitutions. These included G12V (n=4), G12C (n=1), G13C (n=1), G12A (n=1), G12S (n=1), Q22K (n=1), and A146T (n=1). Further, 3 (11.1%) of the lung cancer specimens harbored EGFR mutations (ΔE746_A750 [n=2] and R680Q [n=1]) and 3 (11%) contained DDR2 mutations. Two (7%) of the 27 lung cancer samples had BRAF mutations (G464V and E501V). Some specimens with KRAS mutations had co-occurring mutations in at least one of EGFR, DDR2, BRAF, MET, PIK3CA, PIK3R1, PTCH1, and TP53 (FIG. 6D). A PTEN mutation was detected in one lung cancer specimen along with a co-occurring mutation in DDR2. Only 1 lung cancer specimen harbored an STK11 mutation. TP53 was also mutated in 12 (44%) of the lung cancer specimens (FIG. 6D).

Figure 6E:
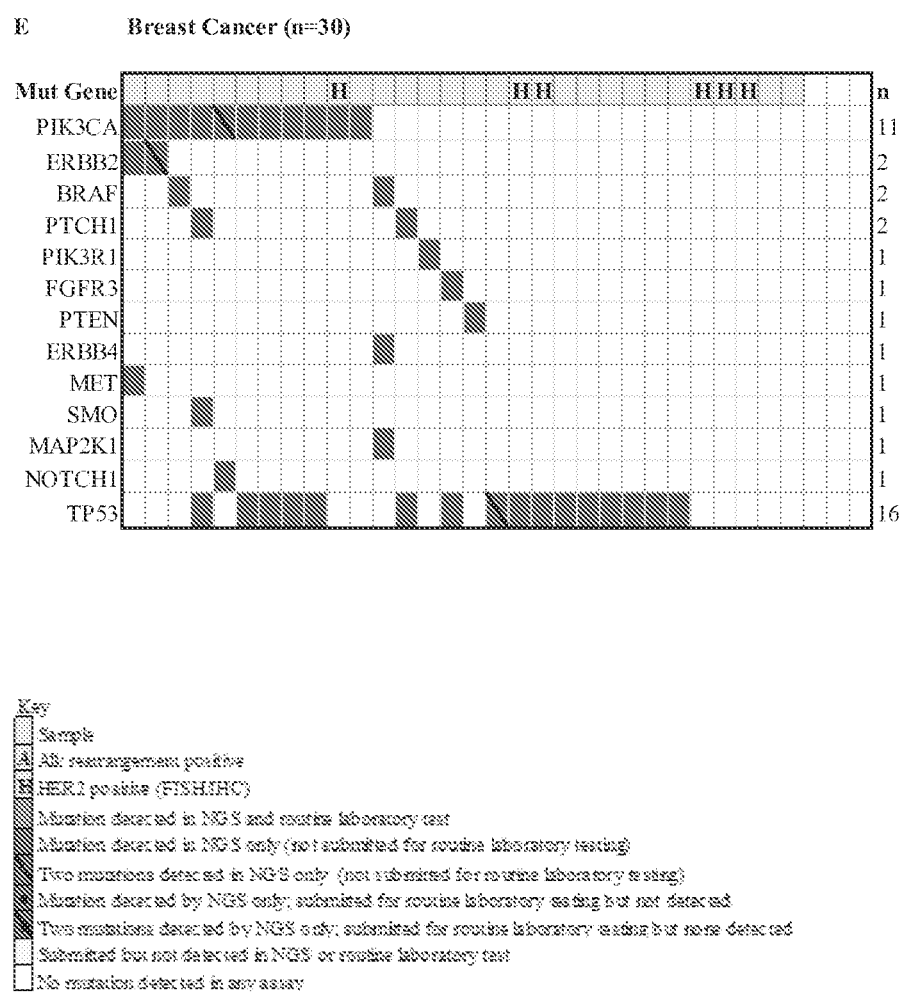

As shown in FIG. 6E, ~37% of the breast cancer specimens harbored PIK3CA mutations. One of the breast cancer samples had two co-occurring PIK3CA mutations (E542Q and H1047R) and a co-occurring mutation in NOTCH1. Two breast cancer specimens (7%) harbored ERBB2 mutations along with co-occurring PIK3CA mutations, one of which had two co-occurring ERBB2 point mutations (L755S and S310Y). Examples of additional mutated genes in breast cancer specimens included PTCH1 (7%) and single instances of PIK3R1, FGFR3, PTEN, ERBB4, MET, SMO, MAP2K1, and NOTCH1 (3%). TP53 was also mutated in 53% (16/30) of the breast cancer specimens (FIG. 6E).

These results demonstrate that the solid tumor screening assay of the present technology is useful in detecting a broad range of mutations in specifically targeted exons or gene regions of AKT1, ERBB2, FOXL2, IDH2, NRAS, RET, ALK, ERBB4, GNA11, KIT PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN in FFPE tissue samples. Therefore, DNA degradation and partial DNA denaturation during embedding of the tissues, long term storage of FFPE tissue samples and the presence of potential PCR inhibitors in tumor samples do not appear to influence the integrity of the solid tumor screening assay of the present technology.

Further, these results demonstrate that the solid tumor screening assay of the present technology is useful in methods for detecting at least one mutation in the plurality of cancer-related genes disclosed herein in a subject diagnosed with breast cancer, lung cancer, colorectal cancer, or melanoma.

Example 5: The Solid Tumor Screening Assay of the Present Technology has Improved Sensitivity and Breadth of Coverage Compared to Sanger Sequencing Single-Analyte Concordance of Mutation Detection Between the Solid Tumor Screening Assay of the Present Technology and Sanger sequencing. The Sanger sequencing tests ordered for each specimen are listed in Table 5.

TABLE 5

Sanger Sequencing Tests Initially Ordered for the 121 FFPE Specimens

| Tumor type | Gene Tested | Number of case (%) |
|---|---|---|
| Melanoma | BRAF | 30 (96.8) |
|  | KIT | 6 (19.4) |
|  | Total | 31 |
| Lung cancer | EGFR | 26 (96.3) |
|  | KRAS | 11 (40.7) |
|  | ALK | 16 (59.3) |
|  | ROS1 | 1 (3.7) |
|  | Total | 27 |
| Colorectal cancer | KRAS | 33 (100) |
|  | NRAS | 6 (18.2) |
|  | BRAF | 5 (15.2) |
|  | PIK3CA | 2 (6.1) |
|  | Total | 33 |
| Breast cancer | ER | 30 (100) |
|  | PR | 30 (100) |
|  | HER-2 | 18 (60.0) |
|  | Total | 30 |

The results of the initially ordered Sanger sequencing tests were compared with the solid tumor screening assay of the present technology for lung cancer, colorectal cancer, and melanoma samples (91 total FFPE specimens). Breast cancer specimens were not included in this analysis because no Sanger sequencing tests are routinely offered for breast cancer.

Some FFPE specimens had multiple tests ordered, yielding 121 Sanger sequencing assay results. 24 of the 121 Sanger sequencing assays were mutation positive (20%) and 97 were negative (80%). In contrast, the solid tumor screening assay of the present technology detected 34 mutations in the 91 FFPE specimens (28%), i.e., 10 more positive results compared to that observed with the initially ordered Sanger sequencing assays. Further, the solid tumor screening assay of the present technology detected every mutation identified by Sanger sequencing.

Discrepancies between the Sanger sequencing tests and the solid tumor screening assay of the present technology were discovered for all 3 tumor types. See Table 6.

TABLE 6

Discrepancies Between the Sanger Sequencing Tests and the Solid Tumor Screening Assay of the Present Technology

| Tumor type | Sample Number | Gene | Mutation | Allele Frequency (%) |
|---|---|---|---|---|
| Melanoma | 1 | BRAF | V600E[a] | 56.1 |
|  | 2 | BRAF | V600E[a] | 59.2 |
|  | 3 | BRAF | K483Q[b] | 61.3 |
| Lung Cancer | 1 | EGFR | ΔE746-A750 | 6 |
|  | 2 | EGFR | R680Q | 10.1 |
|  | 3 | KRAS | A146T[b] | 53.6 |
|  | 4 | KRAS | R68M[b] | 19.9 |
| Colorectal Cancer | 1 | KRAS | A146T[b] | 34.1 |
|  | 2 | KRAS | L19F[b] | 15.7 |
|  | 3 | PIK3CA | C420R[b] | 15.4 |

[a]dinucleotide mutation, not covered by cobas test
[b]not covered (routinely sequenced) by Sanger sequencing test Three FFPE melanoma samples were negative for BRAF mutations according to the initial cobas BRAF test and positive according to the solid tumor screening NGS assay of the present technology (Table 6). Two of the three mutations were BRAF V600E dinucleotide mutations (GTG to GAA) and the remaining one was a BRAF K483Q mutation.

Among the three discrepant colorectal cancer specimens, two had non-codon 12/13/61 KRAS mutations and one had an exon 7 PIK3CA mutation; none of these mutations were covered in the initial Sanger sequencing assays. See Table 6.

Of the four discrepant lung cancer specimens, two had EGFR mutations and two had non-codon 12/13/61 KRAS mutations; the KRAS mutations were not covered in the initial laboratory Sanger sequencing assays. See Table 6. Further, detection of the EGFR exon 19 deletion (ΔE746-A750) demonstrates that the solid tumor screening NGS assay of the present technology can detect mutations at a lower allelic fraction than Sanger sequencing, and is thus more sensitive than Sanger sequencing.

An analysis of the results indicates that the solid tumor screening NGS assay of the present technology has improved breadth of coverage and sensitivity over Sanger sequencing methods.

Example 6: Additional Genes not Tested in the Initial Sanger Sequencing Assays

Melanoma: As shown in FIG. 6B, the solid tumor screening NGS assay of the present technology detected an additional 22 non-BRAF mutations in 12 of the 20 initially BRAF negative samples (60%)—FBXW7 (1), MAP2K1 (1), MET (2), NRAS (6), NOTCH1 (1), PIK3CA (2), PIK3R1 (1), SMO (2), PTEN(1) and TP53 (5). Moreover, seven of the 10 initially BRAF positive specimens harbored non-BRAF mutations—EGFR (1), FGFR3(1), IDH1(1), MAP2KJ(2), MET(1), PTEN (3), and TP53 (2).

Colorectal Cancer. As shown in FIG. 6C, the solid tumor screening NGS assay of the present technology detected mutations in 22 (91%) of the 24 specimens that were either not submitted for or tested negative according to the initial Sanger sequencing assays. These included mutations in non-codon 12/13/61 KRAS (2), BRAF (3), PIK3CA (5), NRAS (1), RET(1), PTEN (1), and FGFR3 (1). Of the 8 specimens that tested positive for KRAS according to the initial Sanger sequencing tests, two harbored co-occurring PIK3CA mutations and one harbored a co-occurring DDR2 mutation (FIG. 6C).

Lung Cancer: As shown in FIG. 6D, the solid tumor screening NGS assay of the present technology detected at least one mutation in 10 (50%) of the 20 specimens that tested negative according to the initial Sanger sequencing assays. These included mutations in KRAS, BRAF, NRAS, DDR2, MET, and EGFR. Furthermore, four (57%) of the seven specimens that were positive according to the initial Sanger sequencing assay also harbored at least one additional mutation in EGFR, KRAS, BRAF, PIK3CA, or MET. Notably, an ALK rearrangement-positive specimen also harbored a codon 22 activating KRAS mutation (FIG. 6D).

Breast cancer. The solid tumor screening NGS assay of the present technology was used to interrogate the 30 breast cancer specimens submitted for HER-2, ER and PR testing. See FIG. 6E. The HER-2 status of twenty-eight of the 30 breast cancer FFPE specimens was assayed by IHC and/or FISH. Of the 22 HER-2-negative specimens, 11 (50%) harbored mutations in RTK or PI3K pathway genes: 9 mutations in PIK3CA; 2 in ERBB2; 1 in PIK3RJ; 1 in PTEN; and 1 in BRAF (FIG. 7). Notably, all HER-2-negative samples harboring ERBB2 or BRAF mutations also had co-occurring PIK3CA mutations (FIG. 7). One of the six HER-2 positive specimens also harbored a PIK3CA mutation. The detailed mutation profile of the different combinations of HER-2, ER and PR status is shown in FIG. 7.

Example 7: Implications on Treatment Selection

This Example demonstrates that the broader mutation profiling by the solid tumor screening NGS assay of the present technology provides additional information relevant to treatment selection beyond routine Sanger sequencing. This additional information was elucidated as a result of sequencing genes or gene regions not typically tested in a given tumor type, identifying co-occurring gene mutations, and the elevated sensitivity of the methods disclosed herein over standard Sanger sequencing.

As shown in FIGS. 6 (A)-(E) and FIG. 7, the solid tumor screening NGS assay of the present technology can provide a more complete molecular profile for a significant proportion of FFPE specimens submitted for molecular testing. For example, 76% (92/121) of the tested FFPE specimens yielded at least one additional gene mutation that was not identified by routine Sanger sequencing. Further, the methods of the present technology led to the identification of 16 actionable mutations (3 BRAF in melanoma, 2 KRAS, 2 BRAF and 1 NRAS in colorectal cancer, 2 EGFR and 6 KRAS in lung cancer) that were not detected by routine Sanger sequencing, which would most likely impact the chosen treatment strategy.

Moreover, the various co-occurring mutations identified by the methods of the present technology are useful in altering or designing a customized treatment regimen. These include consideration of alternative anti-HER-2 therapies (e.g., trastuzumab emtansine), EGFR TKIs (e.g., gefitinib), BRAF inhibitors (e.g., vemurifenab or dabrafenib), Src-family tyrosine kinase inhibitors (e.g., dasatinib), MEK inhibitors (e.g., selumetinib), and/or replacement or removal of classic anti-HER-2 therapies (e.g., trastuzumab), ALK/c-MET inhibitors (e.g., crizotinib), or anti-EGFR therapies (e.g., cetuximab).

Melanoma. The BRAF inhibitor vemurafenib is the most common targeted therapy for melanoma and is used treat BRAF V600 mutation-positive tumors. As shown in Table 5, the majority of melanoma specimens (30/31) were submitted for routine BRAF testing. 21 (68%) of the 31 melanoma samples tested negative according to the initial cobas BRAF test. However, two of the negative specimens were identified as harboring dual-nucleotide variants of BRAF V600E using the methods of the present technology, and are likely to benefit from treatment with vemurafenib.

Additionally, four BRAF mutation-negative specimens were identified as harboring mutations in NRAS (FIG. 6B). Clinical studies have shown that NRAS mutations may indicate a lack of responsiveness to vemurafenib. Su et al., *N Engl J Med* 366:207-215 (2012). However, these mutations may be responsive to MEK inhibitors. Ascierto et al., *Lancet Oncol.* 14(3):249-56 (2013).

Accordingly, the solid tumor screening NGS assay of the present technology is useful in determining whether a melanoma patient is likely to respond to treatment with vemurafenib or MEK inhibitors.

Also notable was the high proportion of BRAF-positive specimens with co-occurring mutations in EGFR, MET, FGFR3, IDH1, and/or PTEN. FIG. 6B. It is predicted that such co-occurring mutations will affect responses to targeted treatments. In addition, one PIK3CA and one MET mutation were detected in BRAF mutation-negative specimens. FIG. 6B. Accordingly, the solid tumor screening NGS assay of the present technology is useful in determining whether a melanoma patient is likely to respond to treatment with a drug that modulates PIK3CA or MET activity.

Colorectal Cancer. Of the 33 colorectal cancer specimens initially tested by Sanger sequencing for KRAS, BRAF, NRAS, and/or PIK3CA mutations, 24 (73%) tested negative, thus suggesting a favorable response to anti-EGFR therapy. Strikingly, 11 (46%) of the specimens that tested negative according to Sanger sequencing were identified as positive for mutations in at least one of the EGFR downstream genes: non-codon 12/13/61 KRAS (2), BRAF (2), NRAS (1), PIK3CA (5), or PTEN (1). Thus, the solid tumor screening NGS assay of the present technology suggested a lack of responsiveness to anti-EGFR therapy in 61% of the colorectal cancer samples, in contrast to the 27% predicted by routine Sanger sequencing.

Accordingly, the solid tumor screening NGS assay of the present technology is useful in determining whether a colorectal cancer patient is likely to respond to treatment with anti-EGFR therapy (e.g., cetuximab).

Lung Cancer. In total, at least 37% (10/27) of the lung cancer FFPE specimens harbored mutations that suggested targeted treatment responses beyond what routine Sanger sequencing provided. As shown in FIG. 6D, initial Sanger sequencing of the 27 lung cancer FFPE specimens detected an EGFR mutation in one specimen, KRAS mutations in four, and an ALK rearrangement in two. The remaining 20 specimens were negative for all mutations initially tested. However, the solid tumor screening NGS assay of the present technology identified one specimen (that tested negative according to routine Sanger sequencing) as harboring an activating EGFR ΔE746_A750 mutation that had a low variant frequency of 6%.

Accordingly, the solid tumor screening NGS assay of the present technology is useful in determining whether a lung cancer patient is likely to respond to treatment with an EGFR TKI. In some embodiments, the patient has a low tumor cell burden.

Further, one lung cancer FFPE specimen tested positive for an ALK rearrangement according to routine Sanger sequencing, thereby suggesting a favorable response to crizotinib. However, the solid tumor screening NGS assay of the present technology identified an activating mutation in KRAS (codon 22), which has been associated with a lack of responsiveness to crizotinib.

Accordingly, the solid tumor screening NGS assay of the present technology is useful in determining whether a lung cancer patient is likely to respond to treatment with crizotinib.

Notably, the methods of the present technology identified an additional 9 (45%) out of the 20 lung cancer specimens that tested negative according to Sanger sequencing, as being positive for alterations in KRAS, BRAF, MET and DDR2. BRAF inhibitors vemurafenib and dabrafenib have been added to the NCCN Guidelines list of "Available Targeted Agents with Activity against Driver Event in Lung Cancer" for specimens harboring BRAF mutations. Sinchez-Torres et al., *Transl Lung Cancer Res* 2(3):244-250 (2013). Additionally, dasatinib is currently being studied for treatment of tumors harboring DDR2 mutations. Bail et al., *Cancer Res.* 2014 Oct. 27 (epub ahead of print).

Accordingly, the solid tumor screening NGS assay of the present technology is useful in determining whether a lung cancer patient is likely to respond to treatment with vemurafenib, dabrafenib, dasatinib or the MEK inhibitor selumetinib.

Breast Cancer. 28 of the 30 breast cancer specimens were submitted for HER-2, ER, and PR testing. Of these, six (21%) were HER-2 positive and therefore likely candidates for trastuzumab treatment (FIG. 7). Although five of the six HER-2-positive cases showed no additional mutations in ERBB or PI3K pathway genes, the solid tumor screening NGS assay of the present technology detected a PIK3CA mutation in one sample. This is significant because PIK3CA mutations in HER-2 positive tumors have been associated with lack of responsiveness to conventional anti-HER-2 therapies (e.g. trastuzumab and lapatinib). Berns et al., *Cancer Cell* 12:395-402 (2007). However, trastuzumab emtansine (Kadcyla, Genentech) may be efficacious in treatment of such tumors, since concurrent PIK3CA mutations do not appear to alter outcome with this alternate therapy (American Association for Cancer Research [AACR] 104th Annual Meeting: Abstract LB-63. Presented Apr. 8, 2013).

Accordingly, the solid tumor screening NGS assay of the present technology is useful in determining whether a HER-2 positive patient diagnosed with breast cancer is likely to respond to treatment with anti-HER-2 therapies or trastuzumab emtansine.

Half (11/22) of the HER-2-negative breast cancer specimens harbored mutations in ERBB and/or PI3K pathway genes. Mutations in PIK3CA were observed in the majority, including a subset that harbored co-occurring ERBB2 or BRAF mutations (FIG. 7). A mutation in PTEN was also observed. Overall observed frequencies of PIK3CA and PTEN mutations (37% and 3%, respectively) are consistent with TCGA data (doi: 10.1038/nature11412).

Importantly, breast cancers harboring PIK3CA kinase domain mutations or PTEN loss of function mutations (with no co-occurring BRAF or KRAS mutations) have been demonstrated to respond to treatment with PI3K/AKT/mTOR pathway inhibitors such as everolimus. Sanchez-Torres et al., *Transl Lung Cancer Res* 2(3):244-250 (2013). It is anticipated that these mutations will serve as biomarkers for guiding therapeutic strategies involving anti-HER-2 therapies and PI3K/AKT/mTOR pathway inhibitors.

Accordingly, the solid tumor screening NGS assay of the present technology is useful in determining whether a patient diagnosed with breast cancer is likely to respond to treatment with PI3K/AKT/mTOR pathway inhibitors.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for detecting at least one mutation in a plurality of cancer-related genes in a subject comprising
    (a) extracting genomic DNA from a formalin fixed paraffin-embedded tumor sample obtained from the subject;
    (b) generating a library comprising amplicons corresponding to each of the plurality of cancer-related genes, said plurality of cancer-related genes comprising AKT1, ERBB2, FOXL2, IDH2, NRAS, RET, ALK, ERBB4, GNA11, KIT, PDGFRA, SMO, BRAF, FBXW7, GNAQ, KRAS, PIK3CA, STK11, CTNNB1, FGFR2, GNAS, MAP2K1, PIK3R1, TP53, DDR2, FGFR3, HRAS, MET, PTCH1, EGFR, FGFR4, IDH1, NOTCH1, and PTEN, wherein the amplicons are generated in a multiplex amplification reaction using primer pairs specific for each of the cancer-related genes and wherein at least two of the primer pairs are selected from the group consisting of the primers of SEQ ID NOS: 1-18, 45-54, and 71-274 or the group consisting of the primers of SEQ ID NOS: 19-44, 55-70, and 275-464, wherein:
        (i) generating said library proceeds independently of using a bait set comprising nucleic acid sequences that are complementary to at least one of the plurality of amplicons; and
        (ii) the quality of the genomic DNA extracted from the formalin fixed paraffin-embedded tumor sample is not assessed using quantitative PCR prior to generating the library;
    (c) ligating an adapter sequence to the ends of the plurality of amplicons; and
    (d) detecting at least one mutation in at least one of the plurality of amplicons using high throughput massive parallel sequencing.

2. The method of claim 1, wherein the library comprising amplicons corresponding to each of the plurality of cancer-related genes is generated using no more than 10 ng of extracted genomic DNA from the formalin fixed paraffin-embedded tumor sample.

3. The method of claim 1, wherein the library comprising amplicons corresponding to each of the plurality of cancer-related genes is generated using 11-25 ng of extracted genomic DNA from the formalin fixed paraffin-embedded tumor sample.

4. The method of claim 1, wherein the high throughput massive parallel sequencing is performed using pyrosequencing, reversible dye-terminator sequencing, SOLiD sequencing, Ion semiconductor sequencing, Helioscope single molecule sequencing, sequencing by synthesis, or sequencing by ligation.

5. The method of claim 1, wherein the adapter sequence is a P5 adapter, P7 adapter, P1 adapter, A adapter, or barcode adapter.

6. The method of claim 1, wherein the plurality of amplicons further comprise a unique index sequence.

7. The method of claim 1, wherein the formalin fixed paraffin-embedded tumor sample is a heterogeneous tumor.

8. The method of claim 7, wherein 5% of the cells of the heterogeneous tumor harbor at least one mutation in at least one of the plurality of amplicons.

9. The method of claim 1, wherein the subject is diagnosed with breast cancer, melanoma, colorectal cancer or lung cancer.

10. The method of claim 1, wherein the formalin fixed paraffin-embedded specimen is a heterogeneous tumor.

11. The method of claim 10, wherein 5%-10% of the cells of the heterogeneous tumor harbor at least one mutation in at least one of the plurality of amplicons.

12. The method of claim 1, wherein the subject is diagnosed as having HER-2 negative breast cancer.

13. The method of claim 1, wherein the subject is diagnosed as having colorectal cancer.

14. The method of claim 1, wherein subject is diagnosed as having melanoma.

* * * * *